(12) United States Patent
Kanz et al.

(10) Patent No.: US 11,740,138 B2
(45) Date of Patent: Aug. 29, 2023

(54) ULTRASOUND CATHETER

(71) Applicant: EKOS CORPORATION, Bothell, WA (US)

(72) Inventors: William Russell Kanz, Woodinville, WA (US); Brent Twain Nistal, Seattle, WA (US); Eric Charles Whittaker, Mountlake Terrace, WA (US); Raymond M. Wolniewicz, III, Redmond, WA (US); Randall James Beyreis, Corcoran, MN (US); Michael Kuehn, Maple Grove, MN (US); Laura Elyn Ortega, Fridley, MN (US); Garrett Prahl, Brooklyn Park, MN (US); Travis Richard White, Rockford, MN (US)

(73) Assignee: EKOS CORPORATION, Bothell, WA (US)

( * ) Notice: Subject to any disclaimer, the term of this patent is extended or adjusted under 35 U.S.C. 154(b) by 782 days.

(21) Appl. No.: 16/702,520

(22) Filed: Dec. 3, 2019

(65) Prior Publication Data

US 2020/0109994 A1 Apr. 9, 2020

Related U.S. Application Data

(63) Continuation of application No. 15/178,398, filed on Jun. 9, 2016, now Pat. No. 10,656,025.
(Continued)

(51) Int. Cl.
*A61M 25/00* (2006.01)
*G01K 7/00* (2006.01)
(Continued)

(52) U.S. Cl.
CPC ............ *G01K 7/02* (2013.01); *A61B 17/2202* (2013.01); *A61M 25/0009* (2013.01);
(Continued)

(58) Field of Classification Search
CPC .................................................. A61M 25/0009
See application file for complete search history.

(56) References Cited

U.S. PATENT DOCUMENTS 2,961,382 A 11/1960 Singher et al.
3,352,303 A 11/1967 Delaney
(Continued)

FOREIGN PATENT DOCUMENTS

AU 634470 B2 2/1993
CA 1083040 A 8/1980
(Continued)

OTHER PUBLICATIONS

Abbas, "Development of a Low Cost Shock Pressure Sensor", Thesis, Ohio University, College of Engineering and Technology, Mar. 1988, pp. 149.
(Continued)

*Primary Examiner* — Cachet I Proctor
(74) *Attorney, Agent, or Firm* — Seager, Tufte & Wickhem LLP

(57) ABSTRACT

A first tubular body having a first longitudinal axis extending centrally through the tubular body includes at least one delivery port extending through a wall of the first tubular body. A second tubular body having a second longitudinal axis extends through the second tubular body, the first and second longitudinal axes being displaced from each other such that an asymmetrical longitudinally extending gap is formed between an outer surface of the second tubular body and an interior surface of the first tubular body. A temperature sensor forming a thermocouple extending longitudi-
(Continued)

nally within the gap between the first tubular body and the second tubular body. An inner core is positioned within the second tubular body. The inner core includes least one ultrasound element.

12 Claims, 41 Drawing Sheets

Related U.S. Application Data

(60) Provisional application No. 62/173,863, filed on Jun. 10, 2015.

(51) Int. Cl.
  *G01K 7/02* (2021.01)
  *A61B 17/22* (2006.01)
  *A61N 7/02* (2006.01)
  *A61B 18/00* (2006.01)

(52) U.S. Cl.
  CPC .... *A61N 7/022* (2013.01); *A61B 2018/00797* (2013.01); *A61B 2018/00821* (2013.01); *A61M 2205/3368* (2013.01)

(56) References Cited

U.S. PATENT DOCUMENTS

| | | |
|---|---|---|
| 3,430,625 A | 3/1969 | McLeod, Jr. |
| 3,433,226 A | 3/1969 | Boyd |
| 3,437,851 A | 4/1969 | Cady |
| 3,443,226 A | 5/1969 | Knight |
| 3,565,062 A | 2/1971 | Kuris |
| 3,635,213 A | 1/1972 | Lahay |
| 3,794,910 A | 2/1974 | Ninked et al. |
| 3,827,115 A | 8/1974 | Bom |
| 3,861,391 A | 1/1975 | Antonevich et al. |
| 3,902,083 A | 8/1975 | Zoltan |
| D238,905 S | 2/1976 | Sokol et al. |
| 3,938,502 A | 2/1976 | Bom |
| 3,941,122 A | 3/1976 | Jones |
| 3,976,987 A | 8/1976 | Anger |
| 4,006,743 A | 2/1977 | Kowarski |
| 4,027,659 A | 6/1977 | Slingluff |
| 4,040,414 A | 8/1977 | Suroff |
| D247,251 S | 2/1978 | Napoli |
| 4,192,294 A | 3/1980 | Vasilevsky et al. |
| 4,265,251 A | 5/1981 | Tickner |
| 4,309,989 A | 1/1982 | Fahim |
| 4,312,361 A | 1/1982 | Nicholson et al. |
| 4,319,580 A | 3/1982 | Colley et al. |
| D264,128 S | 4/1982 | Barnes et al. |
| 4,354,502 A | 10/1982 | Colley et al. |
| 4,381,004 A | 4/1983 | Babb |
| 4,457,748 A | 7/1984 | Lallin et al. |
| 4,466,442 A | 8/1984 | Hilmann et al. |
| 4,512,762 A | 4/1985 | Spears |
| 4,531,943 A | 7/1985 | Van Tassel et al. |
| 4,549,533 A | 10/1985 | Cain et al. |
| 4,557,723 A | 12/1985 | Sibalis |
| 4,573,470 A | 3/1986 | Samson et al. |
| 4,582,067 A | 4/1986 | Silverstein et al. |
| 4,587,975 A | 5/1986 | Salo et al. |
| 4,605,399 A | 8/1986 | Weston et al. |
| 4,639,735 A | 1/1987 | Yamamoto et al. |
| 4,640,689 A | 2/1987 | Slibalis |
| 4,646,754 A | 3/1987 | Seale |
| 4,657,543 A | 4/1987 | Langer et al. |
| 4,657,756 A | 4/1987 | Rasor et al. |
| 4,682,596 A | 7/1987 | Bales et al. |
| 4,692,139 A | 9/1987 | Stiles |
| 4,697,595 A | 10/1987 | Breyer et al. |
| 4,698,058 A | 10/1987 | Greenfeld et al. |
| 4,699,150 A | 10/1987 | Kawabuchi et al. |
| 4,702,732 A | 10/1987 | Powers et al. |
| 4,708,716 A | 11/1987 | Sibalis |
| 4,709,698 A | 12/1987 | Johnston et al. |
| 4,710,192 A | 12/1987 | Liotta et al. |
| 4,717,379 A | 1/1988 | Ekholmer |
| 4,729,384 A | 3/1988 | Bazenet |
| 4,739,768 A | 4/1988 | Engelson |
| D296,240 S | 6/1988 | Albright et al. |
| 4,750,902 A | 6/1988 | Wuchinich et al. |
| 4,754,752 A | 7/1988 | Ginsburg et al. |
| 4,762,915 A | 8/1988 | Kung et al. |
| 4,767,402 A | 8/1988 | Kost et al. |
| 4,769,017 A | 9/1988 | Fath et al. |
| 4,770,185 A | 9/1988 | Silverstein et al. |
| 4,772,594 A | 9/1988 | Hashimoto et al. |
| 4,774,958 A | 10/1988 | Feinstein |
| 4,780,212 A | 10/1988 | Kost et al. |
| 4,781,677 A | 11/1988 | Wilcox |
| 4,787,883 A | 11/1988 | Kroyer |
| 4,795,439 A | 1/1989 | Guest |
| 4,797,285 A | 1/1989 | Barenholz et al. |
| 4,808,153 A | 2/1989 | Parisi |
| 4,820,260 A | 4/1989 | Hayden |
| 4,821,740 A | 4/1989 | Tachibana et al. |
| 4,841,977 A | 6/1989 | Griffith et al. |
| 4,844,882 A | 7/1989 | Widder et al. |
| 4,855,064 A | 8/1989 | Schlein |
| 4,870,953 A | 10/1989 | Don Micheal et al. |
| 4,877,031 A | 10/1989 | Conway et al. |
| 4,883,457 A | 11/1989 | Sibalis |
| 4,900,540 A | 2/1990 | Ryan et al. |
| 4,917,088 A | 4/1990 | Crittenden |
| 4,917,102 A | 4/1990 | Miller et al. |
| 4,920,954 A | 5/1990 | Alliger et al. |
| 4,921,478 A | 5/1990 | Solano et al. |
| 4,924,863 A | 5/1990 | Sterzer |
| 4,933,843 A | 6/1990 | Scheller et al. |
| 4,936,281 A | 6/1990 | Stasz |
| 4,947,852 A | 8/1990 | Nassi et al. |
| 4,948,587 A | 8/1990 | Kost et al. |
| 4,951,677 A | 8/1990 | Crowley et al. |
| 4,953,565 A | 9/1990 | Tachibana et al. |
| 4,955,863 A | 9/1990 | Walker et al. |
| 4,960,109 A | 10/1990 | Lele |
| 4,969,470 A | 11/1990 | Mohl et al. |
| 4,971,991 A | 11/1990 | Umemura et al. |
| 4,992,257 A | 2/1991 | Bonnett et al. |
| 4,995,865 A | 2/1991 | Gahara et al. |
| 5,007,438 A | 4/1991 | Tachibana et al. |
| 5,007,898 A | 4/1991 | Rosenbluth et al. |
| 5,021,044 A | 6/1991 | Sharkawy |
| 5,026,387 A | 6/1991 | Thomas |
| 5,040,537 A | 8/1991 | Katakura |
| 5,053,008 A | 10/1991 | Bajaj |
| 5,053,044 A | 10/1991 | Mueller et al. |
| 5,058,570 A | 10/1991 | Idemoto et al. |
| 5,059,851 A | 10/1991 | Corl et al. |
| 5,069,664 A | 12/1991 | Guess et al. |
| 5,076,276 A | 12/1991 | Sakurai et al. |
| 5,081,993 A | 1/1992 | Kitney et al. |
| 5,085,662 A | 2/1992 | Willard |
| 5,088,499 A | 2/1992 | Unger |
| 5,095,910 A | 3/1992 | Powers |
| 5,108,369 A | 4/1992 | Ganguly et al. |
| 5,115,805 A | 5/1992 | Bommannan et al. |
| 5,117,831 A | 6/1992 | Jang et al. |
| 5,121,749 A | 6/1992 | Nassi et al. |
| 5,125,410 A | 6/1992 | Misono et al. |
| 5,129,883 A | 7/1992 | Black |
| 5,149,319 A | 9/1992 | Unger |
| 5,150,705 A | 9/1992 | Stinson |
| D330,424 S | 10/1992 | Davis et al. |
| 5,156,050 A | 10/1992 | Schmid |
| 5,158,071 A | 10/1992 | Umemura et al. |
| 5,163,421 A | 11/1992 | Bernstein et al. |
| 5,163,436 A | 11/1992 | Saitoh et al. |
| 5,178,620 A | 1/1993 | Eggers et al. |
| 5,181,920 A | 1/1993 | Mueller et al. |
| 5,185,071 A | 2/1993 | Serwer et al. |
| 5,190,766 A | 3/1993 | Ishihara |

(56) References Cited

U.S. PATENT DOCUMENTS

| | | |
|---|---|---|
| 5,195,520 A | 3/1993 | Schlief et al. |
| 5,197,946 A | 3/1993 | Tachibana |
| 5,203,337 A | 4/1993 | Feldman |
| 5,207,214 A | 5/1993 | Romano |
| 5,209,720 A | 5/1993 | Unger |
| 5,215,680 A | 6/1993 | D'arrigo |
| 5,216,130 A | 6/1993 | Line et al. |
| 5,226,421 A | 7/1993 | Frisbie et al. |
| 5,250,034 A | 10/1993 | Appling et al. |
| 5,261,291 A | 11/1993 | Schoch et al. |
| 5,267,954 A | 12/1993 | Nita |
| 5,267,985 A | 12/1993 | Shimada et al. |
| 5,269,291 A | 12/1993 | Carter |
| 5,269,297 A | 12/1993 | Weng et al. |
| 5,271,406 A | 12/1993 | Ganguly et al. |
| 5,277,913 A | 1/1994 | Thompson et al. |
| 5,279,543 A | 1/1994 | Glikfeld et al. |
| 5,279,546 A | 1/1994 | Mische et al. |
| 5,282,785 A | 2/1994 | Shapland et al. |
| 5,286,254 A | 2/1994 | Shapland et al. |
| 5,289,831 A | 3/1994 | Bosley |
| 5,291,887 A | 3/1994 | Stanley et al. |
| 5,295,484 A | 3/1994 | Marcus et al. |
| 5,295,958 A | 3/1994 | Shturman |
| 5,304,115 A | 4/1994 | Pflueger et al. |
| 5,307,816 A | 5/1994 | Hashimoto et al. |
| 5,312,328 A | 5/1994 | Nita et al. |
| 5,313,949 A | 5/1994 | Yock |
| 5,315,998 A | 5/1994 | Tachibana et al. |
| 5,318,014 A | 6/1994 | Carter |
| 5,323,769 A | 6/1994 | Bommannan et al. |
| 5,324,225 A | 6/1994 | Satoh et al. |
| 5,324,255 A | 6/1994 | Passafaro et al. |
| 5,326,342 A | 7/1994 | Pflueger et al. |
| 5,327,891 A | 7/1994 | Rammler |
| 5,328,470 A | 7/1994 | Nabel et al. |
| 5,342,292 A | 8/1994 | Nita et al. |
| 5,342,608 A | 8/1994 | Moriya et al. |
| 5,344,395 A | 9/1994 | Whalen et al. |
| 5,344,435 A | 9/1994 | Turner et al. |
| 5,345,940 A | 9/1994 | Seward et al. |
| 5,348,481 A | 9/1994 | Ortiz |
| 5,351,693 A | 10/1994 | Taimisto et al. |
| 5,353,798 A | 10/1994 | Sieben |
| 5,354,279 A | 10/1994 | Hoefung |
| 5,362,309 A | 11/1994 | Carter |
| 5,363,853 A | 11/1994 | Lieber et al. |
| 5,364,344 A | 11/1994 | Beattie et al. |
| 5,368,036 A | 11/1994 | Tanaka et al. |
| 5,368,557 A | 11/1994 | Nita et al. |
| 5,368,558 A | 11/1994 | Nita |
| 5,370,675 A | 12/1994 | Edwards et al. |
| 5,372,138 A | 12/1994 | Crowley et al. |
| 5,378,230 A | 1/1995 | Mahurkar |
| 5,380,273 A | 1/1995 | Dubrul et al. |
| 5,385,148 A | 1/1995 | Lesh et al. |
| 5,390,678 A | 2/1995 | Gesswein et al. |
| 5,397,293 A | 3/1995 | Alliger et al. |
| 5,397,301 A | 3/1995 | Pflueger et al. |
| 5,399,158 A | 3/1995 | Lauer et al. |
| 5,401,237 A | 3/1995 | Tachibana et al. |
| 5,403,323 A | 4/1995 | Smith |
| 5,405,322 A | 4/1995 | Lennox et al. |
| 5,409,458 A | 4/1995 | Khairkhahan et al. |
| 5,415,636 A | 5/1995 | Forman |
| 5,419,763 A | 5/1995 | Hildabrand |
| 5,421,338 A | 6/1995 | Crowley et al. |
| 5,423,797 A | 6/1995 | Adrian et al. |
| 5,431,663 A | 7/1995 | Carter |
| 5,440,914 A | 8/1995 | Tachibana et al. |
| 5,445,155 A | 8/1995 | Sieben |
| 5,447,509 A | 9/1995 | Mills et al. |
| 5,447,510 A | 9/1995 | Jensen |
| 5,453,575 A | 9/1995 | O'donnell et al. |
| 5,454,782 A | 10/1995 | Perkins |
| 5,454,795 A | 10/1995 | Samson |
| 5,456,259 A | 10/1995 | Barlow et al. |
| 5,456,726 A | 10/1995 | Kawabata et al. |
| 5,458,568 A | 10/1995 | Racchini et al. |
| 5,461,708 A | 10/1995 | Kahn |
| 5,462,523 A | 10/1995 | Samson et al. |
| 5,465,726 A | 11/1995 | Dickinson et al. |
| 5,474,530 A | 12/1995 | Passafaro et al. |
| 5,474,531 A | 12/1995 | Carter |
| 5,489,279 A | 2/1996 | Meserol |
| 5,496,294 A | 3/1996 | Hergenrother et al. |
| 5,498,236 A | 3/1996 | Dubrul et al. |
| 5,498,238 A | 3/1996 | Shapland et al. |
| 5,509,896 A | 4/1996 | Carter |
| 5,514,092 A | 5/1996 | Forman et al. |
| 5,520,189 A | 5/1996 | Malinowski et al. |
| 5,523,058 A | 6/1996 | Umemura et al. |
| 5,524,624 A | 6/1996 | Tepper et al. |
| 5,531,715 A | 7/1996 | Engelson et al. |
| 5,533,986 A | 7/1996 | Mottola et al. |
| 5,542,917 A | 8/1996 | Nita et al. |
| 5,542,935 A | 8/1996 | Unger et al. |
| 5,558,092 A | 9/1996 | Unger et al. |
| 5,558,642 A | 9/1996 | Schweich, Jr. et al. |
| 5,560,362 A | 10/1996 | Sliwa et al. |
| 5,562,608 A | 10/1996 | Sekins et al. |
| 5,567,687 A | 10/1996 | Magda et al. |
| 5,569,197 A | 10/1996 | Helmus et al. |
| 5,569,198 A | 10/1996 | Racchini |
| 5,580,575 A | 12/1996 | Unger et al. |
| 5,582,586 A | 12/1996 | Tachibana et al. |
| 5,585,112 A | 12/1996 | Unger et al. |
| 5,586,982 A | 12/1996 | Abela |
| 5,588,432 A | 12/1996 | Crowley |
| 5,588,962 A | 12/1996 | Nicholas et al. |
| 5,594,136 A | 1/1997 | Sessler et al. |
| 5,599,326 A | 2/1997 | Carter |
| 5,599,923 A | 2/1997 | Sessler et al. |
| 5,603,327 A | 2/1997 | Eberle et al. |
| 5,603,694 A | 2/1997 | Brown et al. |
| 5,606,974 A | 3/1997 | Castellano et al. |
| 5,609,574 A | 3/1997 | Kaplan et al. |
| 5,616,342 A | 4/1997 | Lyons |
| 5,617,851 A | 4/1997 | Lipkovker |
| 5,618,275 A | 4/1997 | Bock |
| 5,620,409 A | 4/1997 | Venuto et al. |
| 5,620,479 A | 4/1997 | Diederich |
| 5,624,382 A | 4/1997 | Oppelt et al. |
| 5,628,728 A | 5/1997 | Tachibana et al. |
| 5,628,730 A | 5/1997 | Shapland et al. |
| 5,630,837 A | 5/1997 | Crowley |
| 5,632,970 A | 5/1997 | Sessler et al. |
| D380,543 S | 7/1997 | Piontek et al. |
| 5,648,098 A | 7/1997 | Porter |
| 5,656,016 A | 8/1997 | Ogden |
| 5,660,180 A | 8/1997 | Malinowski et al. |
| 5,660,909 A | 8/1997 | Tachibana et al. |
| 5,663,327 A | 9/1997 | Tambo et al. |
| 5,665,076 A | 9/1997 | Roth et al. |
| 5,681,296 A | 10/1997 | Ishida |
| 5,688,364 A | 11/1997 | Sato |
| 5,694,936 A | 12/1997 | Fujimoto et al. |
| 5,695,460 A | 12/1997 | Siegel et al. |
| 5,697,897 A | 12/1997 | Buchholtz et al. |
| 5,707,608 A | 1/1998 | Liu |
| 5,713,831 A | 2/1998 | Olsson |
| 5,713,848 A | 2/1998 | Dubrul et al. |
| 5,715,825 A | 2/1998 | Crowley |
| 5,718,921 A | 2/1998 | Mathiowitz et al. |
| 5,720,710 A | 2/1998 | Tachibana et al. |
| 5,724,976 A | 3/1998 | Mine et al. |
| 5,725,494 A | 3/1998 | Brisken |
| 5,728,062 A | 3/1998 | Brisken |
| 5,733,315 A | 3/1998 | Burdette et al. |
| 5,733,572 A | 3/1998 | Unger et al. |
| 5,735,811 A | 4/1998 | Brisken |
| 5,752,930 A | 5/1998 | Rise et al. |
| 5,766,902 A | 6/1998 | Craig et al. |
| 5,770,222 A | 6/1998 | Unger et al. |

(56) References Cited

U.S. PATENT DOCUMENTS

| | | |
|---|---|---|
| 5,772,627 A | 6/1998 | Acosta et al. |
| 5,772,632 A | 6/1998 | Forman |
| 5,775,338 A | 7/1998 | Hastings |
| 5,776,429 A | 7/1998 | Unger et al. |
| 5,779,644 A | 7/1998 | Eberle et al. |
| 5,779,673 A | 7/1998 | Roth et al. |
| 5,782,811 A | 7/1998 | Samson et al. |
| 5,800,421 A | 9/1998 | Lemelson |
| 5,807,395 A | 9/1998 | Mulier et al. |
| 5,817,021 A | 10/1998 | Reichenberger |
| 5,817,048 A | 10/1998 | Lawandy |
| 5,823,962 A | 10/1998 | Schaetzle et al. |
| 5,824,005 A | 10/1998 | Motamed et al. |
| 5,827,203 A | 10/1998 | Nita |
| 5,827,313 A | 10/1998 | Ream |
| 5,827,529 A | 10/1998 | Ono et al. |
| 5,834,880 A | 11/1998 | Venkataramani et al. |
| 5,836,440 A | 11/1998 | Mindich |
| 5,836,896 A | 11/1998 | Rosenschein |
| 5,836,940 A | 11/1998 | Gregory |
| 5,840,031 A | 11/1998 | Crowley |
| 5,842,994 A | 12/1998 | Fenhoff et al. |
| 5,843,109 A | 12/1998 | Mehta et al. |
| 5,846,218 A | 12/1998 | Brisken et al. |
| 5,846,517 A | 12/1998 | Unger |
| 5,849,727 A | 12/1998 | Porter et al. |
| 5,876,345 A | 3/1999 | Eaton et al. |
| 5,876,989 A | 3/1999 | Berg et al. |
| 5,895,356 A | 4/1999 | Andrus et al. |
| 5,895,358 A | 4/1999 | Becker et al. |
| 5,895,398 A | 4/1999 | Wensel et al. |
| 5,897,503 A | 4/1999 | Lyon et al. |
| 5,908,445 A | 6/1999 | Whayne et al. |
| 5,916,192 A | 6/1999 | Nita et al. |
| 5,922,687 A | 7/1999 | Mann et al. |
| 5,925,016 A | 7/1999 | Chornenky et al. |
| 5,928,186 A | 7/1999 | Homsma et al. |
| 5,931,805 A | 8/1999 | Brisken |
| 5,934,284 A | 8/1999 | Plaia et al. |
| 5,935,124 A | 8/1999 | Klumb et al. |
| 5,938,595 A | 8/1999 | Glass et al. |
| 5,941,068 A | 8/1999 | Brown et al. |
| 5,941,868 A | 8/1999 | Kaplan et al. |
| 5,941,896 A | 8/1999 | Kerr |
| 5,951,494 A | 9/1999 | Wang et al. |
| 5,957,851 A | 9/1999 | Hossack |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,984,882 A | 11/1999 | Rosenschein et al. |
| 5,997,497 A | 12/1999 | Nita et al. |
| 6,001,069 A | 12/1999 | Tachibana et al. |
| 6,004,069 A | 12/1999 | Sudbury |
| 6,004,269 A | 12/1999 | Crowley et al. |
| 6,007,514 A | 12/1999 | Nita |
| 6,024,703 A | 2/2000 | Zanelli et al. |
| 6,024,718 A | 2/2000 | Chen et al. |
| 6,027,515 A | 2/2000 | Cimino |
| 6,030,374 A | 2/2000 | McDaniel |
| 6,033,397 A | 3/2000 | Laufer et al. |
| 6,044,845 A | 4/2000 | Lewis |
| 6,053,868 A | 4/2000 | Geistert et al. |
| 6,059,731 A | 5/2000 | Seward et al. |
| 6,063,069 A | 5/2000 | Cragg et al. |
| 6,066,123 A | 5/2000 | Li et al. |
| 6,068,857 A | 5/2000 | Weitschies et al. |
| 6,078,830 A | 6/2000 | Levin et al. |
| D427,574 S | 7/2000 | Sawada et al. |
| 6,086,573 A | 7/2000 | Siegel et al. |
| 6,088,613 A | 7/2000 | Unger |
| 6,089,573 A | 7/2000 | Udagawa |
| 6,096,000 A | 8/2000 | Tachibana et al. |
| 6,096,070 A | 8/2000 | Ragheb et al. |
| 6,110,098 A | 8/2000 | Renirie et al. |
| 6,110,314 A | 8/2000 | Nix et al. |
| 6,113,546 A | 9/2000 | Suorsa et al. |
| 6,113,558 A | 9/2000 | Rosenschein et al. |
| 6,113,570 A | 9/2000 | Siegel et al. |
| 6,117,101 A | 9/2000 | Diederich et al. |
| 6,117,858 A | 9/2000 | Porter et al. |
| 6,120,454 A | 9/2000 | Suorsa et al. |
| RE36,939 E | 10/2000 | Tachibana et al. |
| 6,135,971 A | 10/2000 | Hutchinson et al. |
| 6,135,976 A | 10/2000 | Tachibana et al. |
| 6,136,792 A | 10/2000 | Henderson |
| 6,143,013 A | 11/2000 | Samson et al. |
| 6,144,869 A | 11/2000 | Berner et al. |
| 6,149,596 A | 11/2000 | Bancroft |
| 6,149,599 A | 11/2000 | Schlesinger et al. |
| 6,176,842 B1 | 1/2001 | Tachibana et al. |
| 6,190,315 B1 | 2/2001 | Kost et al. |
| 6,190,355 B1 | 2/2001 | Hastings |
| 6,196,973 B1 | 3/2001 | Lazenby et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,241,703 B1 | 6/2001 | Levin et al. |
| 6,245,747 B1 | 6/2001 | Porter et al. |
| 6,261,246 B1 | 7/2001 | Pantages et al. |
| 6,270,460 B1 | 8/2001 | McCartan et al. |
| 6,277,077 B1 | 8/2001 | Brisken et al. |
| 6,283,920 B1 | 9/2001 | Eberle et al. |
| 6,287,271 B1 | 9/2001 | Dubrul et al. |
| 6,295,990 B1 | 10/2001 | Lewis et al. |
| 6,296,610 B1 | 10/2001 | Schneider et al. |
| 6,296,619 B1 | 10/2001 | Brisken et al. |
| 6,298,264 B1 | 10/2001 | Zhong et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,312,425 B1 | 11/2001 | Simpson et al. |
| 6,319,220 B1 | 11/2001 | Bylsma |
| 6,322,513 B1 | 11/2001 | Schregel |
| 6,346,098 B1 | 2/2002 | Yock et al. |
| 6,356,776 B1 | 3/2002 | Berner et al. |
| 6,361,500 B1 | 3/2002 | Masters |
| 6,361,554 B1 | 3/2002 | Brisken |
| 6,366,719 B1 | 4/2002 | Heath et al. |
| 6,368,315 B1 | 4/2002 | Gillis et al. |
| 6,372,498 B2 | 4/2002 | Newman et al. |
| 6,379,320 B1 | 4/2002 | Lafon et al. |
| 6,387,035 B1 | 5/2002 | Jung et al. |
| 6,387,052 B1 | 5/2002 | Quinn et al. |
| 6,391,042 B1 | 5/2002 | Cimino |
| 6,394,956 B1 | 5/2002 | Chandrasekaran et al. |
| 6,394,997 B1 | 5/2002 | Lemelson |
| 6,398,772 B1 | 6/2002 | Bond et al. |
| 6,398,792 B1 | 6/2002 | O'Connor |
| 6,416,740 B1 | 7/2002 | Unger |
| 6,423,026 B1 | 7/2002 | Gesswein et al. |
| 6,425,853 B1 | 7/2002 | Edwards |
| 6,433,464 B2 | 8/2002 | Jones |
| 6,435,189 B1 | 8/2002 | Lewis et al. |
| 6,437,487 B1 | 8/2002 | Mohr et al. |
| 6,454,737 B1 | 9/2002 | Nita et al. |
| 6,454,757 B1 | 9/2002 | Nita et al. |
| 6,456,863 B1 | 9/2002 | Levin et al. |
| 6,461,296 B1 | 10/2002 | Desai |
| 6,461,314 B1 | 10/2002 | Pant et al. |
| 6,461,383 B1 | 10/2002 | Gesswein et al. |
| 6,461,586 B1 | 10/2002 | Unger |
| 6,464,680 B1 | 10/2002 | Brisken et al. |
| 6,471,683 B2 | 10/2002 | Drasler et al. |
| 6,478,765 B2 | 11/2002 | Siegel et al. |
| 6,485,430 B1 | 11/2002 | Quinn et al. |
| 6,485,853 B1 | 11/2002 | Pettit et al. |
| 6,493,731 B1 | 12/2002 | Jones et al. |
| 6,494,891 B1 | 12/2002 | Cornish et al. |

(56) References Cited

U.S. PATENT DOCUMENTS

| | | |
|---|---|---|
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,508,816 B2 | 1/2003 | Shadduck |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,527,759 B1 | 3/2003 | Tachibana et al. |
| 6,527,761 B1 | 3/2003 | Soltesz et al. |
| 6,537,224 B2 | 3/2003 | Mauchamp et al. |
| 6,537,306 B1 | 3/2003 | Burdette et al. |
| 6,542,767 B1 | 4/2003 | McNichols et al. |
| 6,544,259 B1 | 4/2003 | Tsaliovich |
| 6,548,047 B1 | 4/2003 | Unger |
| 6,551,337 B1 | 4/2003 | Rabiner et al. |
| 6,558,366 B1 | 5/2003 | Drasler et al. |
| 6,560,837 B1 | 5/2003 | Hodjat et al. |
| 6,561,998 B1 | 5/2003 | Roth et al. |
| 6,562,021 B1 | 5/2003 | Derbin et al. |
| 6,565,552 B1 | 5/2003 | Barbut |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner et al. |
| 6,582,392 B1 | 6/2003 | Bennett et al. |
| 6,585,678 B1 | 7/2003 | Tachibana et al. |
| 6,585,763 B1 | 7/2003 | Keilman et al. |
| 6,589,182 B1 | 7/2003 | Loftman et al. |
| 6,589,253 B1 | 7/2003 | Cornish et al. |
| 6,594,514 B2 | 7/2003 | Berner et al. |
| 6,599,288 B2 | 7/2003 | Maguire et al. |
| 6,605,084 B2 | 8/2003 | Acker et al. |
| 6,607,502 B1 | 8/2003 | Maguire et al. |
| 6,623,444 B2 | 9/2003 | Babaev |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,536 B2 | 11/2003 | Mathews et al. |
| 6,652,547 B2 | 11/2003 | Rabiner et al. |
| 6,652,581 B1 | 11/2003 | Ding |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,680,301 B2 | 1/2004 | Berg et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,699,269 B2 | 3/2004 | Khanna |
| 6,711,953 B2 | 3/2004 | Hayashi et al. |
| 6,723,063 B1 | 4/2004 | Zhang et al. |
| 6,723,064 B2 | 4/2004 | Babaev |
| 6,726,698 B2 | 4/2004 | Cimino |
| 6,730,048 B1 | 5/2004 | Hare et al. |
| 6,733,450 B1 | 5/2004 | Alexandrov et al. |
| 6,733,451 B2 | 5/2004 | Rabiner et al. |
| 6,733,515 B1 | 5/2004 | Edwards et al. |
| 6,740,040 B1 | 5/2004 | Mandrusov et al. |
| 6,758,857 B2 | 7/2004 | Cioanta et al. |
| 6,764,860 B2 | 7/2004 | Lee |
| 6,767,345 B2 | 7/2004 | St. Germain et al. |
| 6,794,369 B2 | 9/2004 | Newman et al. |
| 6,796,992 B2 | 9/2004 | Barbut |
| 6,797,293 B2 | 9/2004 | Shin et al. |
| 6,824,515 B2 | 11/2004 | Suorsa et al. |
| 6,824,575 B1 | 11/2004 | Otomo et al. |
| 6,830,577 B2 | 12/2004 | Nash et al. |
| 6,849,062 B2 | 2/2005 | Kantor |
| 6,850,790 B2 | 2/2005 | Berner et al. |
| 6,855,123 B2 | 2/2005 | Nita |
| 6,866,670 B2 | 3/2005 | Rabiner et al. |
| 6,896,659 B2 | 5/2005 | Conston et al. |
| 6,905,505 B2 | 6/2005 | Nash et al. |
| 6,908,448 B2 | 6/2005 | Redding |
| 6,913,581 B2 | 7/2005 | Corl et al. |
| 6,921,371 B2 | 7/2005 | Wilson |
| 6,929,632 B2 | 8/2005 | Nita et al. |
| 6,929,633 B2 | 8/2005 | Evans et al. |
| 6,942,620 B2 | 9/2005 | Nita et al. |
| 6,942,677 B2 | 9/2005 | Nita et al. |
| 6,945,937 B2 | 9/2005 | Culp et al. |
| 6,958,040 B2 | 10/2005 | Oliver et al. |
| 6,958,059 B2 | 10/2005 | Zadno-Azizi |
| 6,979,293 B2 | 12/2005 | Hansmann et al. |
| 6,985,771 B2 | 1/2006 | Fischell et al. |
| 7,025,425 B2 | 4/2006 | Kovatchev et al. |
| 7,077,820 B1 | 7/2006 | Kadziauskas et al. |
| D526,655 S | 8/2006 | McDougall et al. |
| 7,084,118 B2 | 8/2006 | Armstrong et al. |
| 7,089,063 B2 | 8/2006 | Lesh et al. |
| 7,137,963 B2 | 11/2006 | Nita et al. |
| 7,141,044 B2 | 11/2006 | Gentsler |
| D534,654 S | 1/2007 | Hayamizu |
| 7,166,098 B1 | 1/2007 | Steward et al. |
| 7,174,199 B2 | 2/2007 | Berner et al. |
| 7,178,109 B2 | 2/2007 | Hewson et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,235,063 B2 | 6/2007 | D'Antonio et al. |
| 7,264,597 B2 | 9/2007 | Cathignol |
| D555,165 S | 11/2007 | Myers et al. |
| 7,300,414 B1 | 11/2007 | Holland et al. |
| 7,308,303 B2 | 12/2007 | Whitehurst et al. |
| 7,309,334 B2 | 12/2007 | von Hoffmann |
| 7,335,180 B2 | 2/2008 | Nita et al. |
| D564,094 S | 3/2008 | Hayashi |
| D564,661 S | 3/2008 | Hayashi |
| 7,341,569 B2 | 3/2008 | Soltani et al. |
| 7,344,509 B2 | 3/2008 | Hynynen et al. |
| 7,384,407 B2 | 6/2008 | Rodriguez et al. |
| D574,961 S | 8/2008 | Kitahara et al. |
| 7,413,556 B2 | 8/2008 | Zhang et al. |
| 7,416,535 B1 | 8/2008 | Kenny |
| D578,543 S | 10/2008 | Ulm et al. |
| 7,440,798 B2 | 10/2008 | Redding, Jr. |
| 7,503,895 B2 | 3/2009 | Rabiner et al. |
| D592,754 S | 5/2009 | Koike et al. |
| D593,117 S | 5/2009 | Lettau |
| 7,540,852 B2 | 6/2009 | Nita et al. |
| 7,567,016 B2 | 7/2009 | Lu et al. |
| 7,604,608 B2 | 10/2009 | Nita et al. |
| 7,613,516 B2 | 11/2009 | Cohen et al. |
| 7,613,664 B2 | 11/2009 | Riezler et al. |
| 7,615,030 B2 | 11/2009 | Murphy et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,715,908 B2 | 5/2010 | Moran et al. |
| 7,717,853 B2 | 5/2010 | Nita |
| D617,332 S | 6/2010 | Loken et al. |
| 7,727,178 B2 | 6/2010 | Wilson et al. |
| 7,758,509 B2 | 7/2010 | Angelsen et al. |
| D622,841 S | 8/2010 | Bierman |
| 7,771,372 B2 | 8/2010 | Wilson |
| 7,774,933 B2 | 8/2010 | Wilson et al. |
| 7,789,830 B2 | 9/2010 | Ishida et al. |
| 7,818,854 B2 | 10/2010 | Wilson |
| 7,828,754 B2 | 11/2010 | Furuhata et al. |
| 7,828,762 B2 | 11/2010 | Wilson et al. |
| D630,727 S | 1/2011 | Petrovic et al. |
| 7,862,576 B2 | 1/2011 | Gurm |
| 7,874,985 B2 | 1/2011 | Kovatchev et al. |
| 7,901,359 B2 | 3/2011 | Mandrusov et al. |
| 7,914,509 B2 | 3/2011 | Bennett et al. |
| D637,287 S | 5/2011 | Mudd et al. |
| 7,976,483 B2 | 7/2011 | Bennett et al. |
| D643,117 S | 8/2011 | Onuma |
| D644,649 S | 9/2011 | Fullington et al. |
| 8,012,092 B2 | 9/2011 | Powers et al. |
| 8,062,566 B2 | 11/2011 | Nita et al. |

(56) References Cited

U.S. PATENT DOCUMENTS

| | | |
|---|---|---|
| D651,212 S | 12/2011 | Bakhreiba et al. |
| 8,123,789 B2 | 2/2012 | Khanna |
| 8,152,753 B2 | 4/2012 | Nita et al. |
| D658,667 S | 5/2012 | Cho et al. |
| D659,151 S | 5/2012 | Loken et al. |
| 8,167,831 B2 | 5/2012 | Wilson et al. |
| 8,192,363 B2 | 6/2012 | Soltani et al. |
| 8,192,391 B2 | 6/2012 | Soltani et al. |
| D664,257 S | 7/2012 | Patil |
| 8,226,629 B1 | 7/2012 | Keilman et al. |
| D664,985 S | 8/2012 | Tanghe et al. |
| 8,298,147 B2 | 10/2012 | Huennekens et al. |
| D670,714 S | 11/2012 | Majeed et al. |
| D670,716 S | 11/2012 | Majeed et al. |
| D670,725 S | 11/2012 | Mori et al. |
| D671,552 S | 11/2012 | Mori et al. |
| D676,562 S | 2/2013 | Marzynski |
| 8,366,620 B2 | 2/2013 | Nita |
| D685,815 S | 7/2013 | Bork et al. |
| D692,907 S | 11/2013 | Schuller et al. |
| D694,774 S | 12/2013 | Schuller et al. |
| D698,925 S | 2/2014 | Marzynski |
| D700,343 S | 2/2014 | Liu |
| 8,690,818 B2 | 4/2014 | Bennett et al. |
| 8,696,612 B2 | 4/2014 | Wilson et al. |
| 8,740,835 B2 | 6/2014 | Soltani et al. |
| 8,762,880 B2 | 6/2014 | Dukhon et al. |
| D709,515 S | 7/2014 | Elston et al. |
| 8,764,700 B2 | 7/2014 | Zhang et al. |
| 8,771,186 B2 | 7/2014 | Kinsley et al. |
| D711,001 S | 8/2014 | Boudier |
| D714,339 S | 9/2014 | Hendrickson et al. |
| 8,819,928 B2 | 9/2014 | Nix et al. |
| D714,948 S | 10/2014 | Vaccarella |
| 8,852,166 B1 | 10/2014 | Keilman et al. |
| D725,784 S | 3/2015 | Xia et al. |
| D733,178 S | 6/2015 | Omiya |
| 9,044,568 B2 | 6/2015 | Wilcox et al. |
| 9,050,123 B2 | 6/2015 | Krause et al. |
| D733,720 S | 7/2015 | Mueller et al. |
| D733,738 S | 7/2015 | Omiya |
| D734,475 S | 7/2015 | Ross |
| 9,107,590 B2 | 8/2015 | Hansmann et al. |
| D741,351 S | 10/2015 | Kito et al. |
| D741,871 S | 10/2015 | Chung et al. |
| 9,192,566 B2 | 11/2015 | Soltani et al. |
| D748,124 S | 1/2016 | Jeon |
| D755,818 S | 5/2016 | Seo et al. |
| D758,397 S | 6/2016 | Lee |
| D763,298 S | 8/2016 | Hoang et al. |
| 9,415,242 B2 | 8/2016 | Wilson et al. |
| D767,583 S | 9/2016 | Xiong |
| D767,584 S | 9/2016 | Xiong |
| D772,252 S | 11/2016 | Myers et al. |
| D773,491 S | 12/2016 | Ahdrilz et al. |
| D776,688 S | 1/2017 | Gamel |
| D779,539 S | 2/2017 | Lee et al. |
| 9,579,494 B2 | 2/2017 | Kersten et al. |
| D782,496 S | 3/2017 | Contreras et al. |
| D783,028 S | 4/2017 | Lee et al. |
| D788,145 S | 5/2017 | Sullivan et al. |
| D794,662 S | 8/2017 | Genstler et al. |
| D797,918 S | 9/2017 | Genstler et al. |
| 9,849,273 B2 | 12/2017 | Soltani et al. |
| D812,075 S | 3/2018 | Fukagawa |
| 9,943,675 B1 | 4/2018 | Keilman et al. |
| D819,807 S | 6/2018 | Genstler et al. |
| 10,080,878 B2 | 9/2018 | Wilson et al. |
| D831,058 S | 10/2018 | Genstler et al. |
| 10,092,742 B2 | 10/2018 | Genstler et al. |
| 10,182,833 B2 | 1/2019 | Soltani et al. |
| 10,188,410 B2 | 1/2019 | Soltani et al. |
| 10,232,196 B2 | 3/2019 | Soltani et al. |
| 2001/0000791 A1 | 5/2001 | Suorsa et al. |
| 2001/0003790 A1 | 6/2001 | Ben-haim et al. |
| 2001/0007666 A1 | 7/2001 | Hoffman et al. |
| 2001/0007861 A1 | 7/2001 | Newman et al. |
| 2001/0007940 A1 | 7/2001 | Tu et al. |
| 2001/0014775 A1 | 8/2001 | Koger et al. |
| 2001/0025190 A1 | 9/2001 | Weber et al. |
| 2001/0037106 A1 | 11/2001 | Shadduck |
| 2001/0039419 A1 | 11/2001 | Francischelli et al. |
| 2001/0041842 A1 | 11/2001 | Eberle et al. |
| 2001/0041880 A1 | 11/2001 | Brisken et al. |
| 2001/0053384 A1 | 12/2001 | Greenleaf et al. |
| 2002/0000763 A1 | 1/2002 | Jones |
| 2002/0018472 A1 | 2/2002 | Rinne et al. |
| 2002/0019644 A1 | 2/2002 | Hastings et al. |
| 2002/0022833 A1 | 2/2002 | Maguire et al. |
| 2002/0032394 A1 | 3/2002 | Brisken et al. |
| 2002/0040184 A1 | 4/2002 | Brown et al. |
| 2002/0041898 A1 | 4/2002 | Unger et al. |
| 2002/0045890 A1 | 4/2002 | Celliers et al. |
| 2002/0052620 A1 | 5/2002 | Barbut |
| 2002/0055731 A1 | 5/2002 | Atala et al. |
| 2002/0068717 A1 | 6/2002 | Borrelli |
| 2002/0068869 A1 | 6/2002 | Brisken et al. |
| 2002/0077550 A1 | 6/2002 | Rabiner et al. |
| 2002/0082238 A1 | 6/2002 | Newman et al. |
| 2002/0087083 A1 | 7/2002 | Nix et al. |
| 2002/0099292 A1 | 7/2002 | Brisken et al. |
| 2002/0123787 A1 | 9/2002 | Weiss |
| 2002/0133081 A1 | 9/2002 | Ackerman et al. |
| 2002/0133111 A1 | 9/2002 | Shadduck |
| 2002/0150901 A1 | 10/2002 | Murphy et al. |
| 2002/0151792 A1 | 10/2002 | Conston et al. |
| 2002/0173028 A1 | 11/2002 | Kapeller-Libermann et al. |
| 2002/0188276 A1 | 12/2002 | Evans et al. |
| 2002/0193708 A1 | 12/2002 | Thompson et al. |
| 2002/0198526 A1 | 12/2002 | Shaolian et al. |
| 2003/0013986 A1 | 1/2003 | Saadat |
| 2003/0023261 A1 | 1/2003 | Tomaschko et al. |
| 2003/0028173 A1 | 2/2003 | Forsberg |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0082649 A1 | 5/2003 | Weich et al. |
| 2003/0083608 A1 | 5/2003 | Evans et al. |
| 2003/0083698 A1 | 5/2003 | Whitehurst et al. |
| 2003/0088187 A1 | 5/2003 | Saadat et al. |
| 2003/0092667 A1 | 5/2003 | Tachibana et al. |
| 2003/0109812 A1 | 6/2003 | Corl et al. |
| 2003/0114761 A1 | 6/2003 | Brown |
| 2003/0135262 A1 | 7/2003 | Dretler et al. |
| 2003/0139774 A1 | 7/2003 | Epstein et al. |
| 2003/0153833 A1 | 8/2003 | Bennett et al. |
| 2003/0157024 A1 | 8/2003 | Tachibana et al. |
| 2003/0163147 A1 | 8/2003 | Rabiner et al. |
| 2003/0167023 A1 | 9/2003 | Bennett et al. |
| 2003/0187320 A1 | 10/2003 | Freyman |
| 2003/0191446 A1 | 10/2003 | Tachibana et al. |
| 2003/0199831 A1 | 10/2003 | Morris et al. |
| 2003/0216681 A1 | 11/2003 | Zhang et al. |
| 2003/0220568 A1 | 11/2003 | Hansmann et al. |
| 2003/0229307 A1 | 12/2003 | Muni et al. |
| 2003/0233085 A1 | 12/2003 | Giammarusti |
| 2003/0236539 A1 | 12/2003 | Rabiner et al. |
| 2004/0001809 A1 | 1/2004 | Brisken et al. |
| 2004/0010290 A1 | 1/2004 | Schroeppel et al. |
| 2004/0015061 A1 | 1/2004 | Currier et al. |
| 2004/0015122 A1 | 1/2004 | Zhang et al. |
| 2004/0015138 A1 | 1/2004 | Currier et al. |
| 2004/0019318 A1 | 1/2004 | Wilson et al. |
| 2004/0024347 A1* | 2/2004 | Wilson ............ A61M 37/0092 604/22 |
| 2004/0024393 A1 | 2/2004 | Nita et al. |
| 2004/0039311 A1 | 2/2004 | Nita et al. |
| 2004/0039329 A1 | 2/2004 | Ueberle |
| 2004/0049148 A1 | 3/2004 | Rodriguez et al. |
| 2004/0054351 A1 | 3/2004 | Deniega et al. |
| 2004/0059313 A1 | 3/2004 | Tachibana et al. |
| 2004/0068189 A1 | 4/2004 | Wilson et al. |

(56) References Cited

U.S. PATENT DOCUMENTS

| | | |
|---|---|---|
| 2004/0077976 A1 | 4/2004 | Wilson |
| 2004/0082857 A1 | 4/2004 | Schonenberger et al. |
| 2004/0097996 A1 | 5/2004 | Rabiner et al. |
| 2004/0106847 A1 | 6/2004 | Benderev |
| 2004/0111195 A1 | 6/2004 | Vries et al. |
| 2004/0122354 A1 | 6/2004 | Semba |
| 2004/0133232 A1 | 7/2004 | Rosenbluth et al. |
| 2004/0138570 A1 | 7/2004 | Nita et al. |
| 2004/0162571 A1 | 8/2004 | Rabiner et al. |
| 2004/0171970 A1 | 9/2004 | Schleuniger et al. |
| 2004/0171981 A1 | 9/2004 | Rabiner et al. |
| 2004/0199228 A1 | 10/2004 | Wilson |
| 2004/0210134 A1 | 10/2004 | Hynynen et al. |
| 2004/0220514 A1 | 11/2004 | Cafferata |
| 2004/0220544 A1 | 11/2004 | Heruth et al. |
| 2004/0225318 A1 | 11/2004 | Eidenschink et al. |
| 2004/0229830 A1 | 11/2004 | Tachibana et al. |
| 2004/0230116 A1 | 11/2004 | Cowan et al. |
| 2004/0236350 A1 | 11/2004 | Lewis et al. |
| 2004/0243062 A1 | 12/2004 | Henry |
| 2004/0254506 A1 | 12/2004 | Cathignol |
| 2004/0255957 A1 | 12/2004 | Cafferata |
| 2004/0265393 A1 | 12/2004 | Unger et al. |
| 2005/0010112 A1 | 1/2005 | Bennett et al. |
| 2005/0021063 A1 | 1/2005 | Hall et al. |
| 2005/0027247 A1 | 2/2005 | Garrison et al. |
| 2005/0038340 A1 | 2/2005 | Vaezy et al. |
| 2005/0043629 A1 | 2/2005 | Rabiner et al. |
| 2005/0043726 A1 | 2/2005 | McHale et al. |
| 2005/0043753 A1 | 2/2005 | Rabiner et al. |
| 2005/0054971 A1 | 3/2005 | Steen et al. |
| 2005/0065461 A1 | 3/2005 | Redding |
| 2005/0090818 A1 | 4/2005 | Pike et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0177212 A1 | 8/2005 | Njemanze |
| 2005/0187513 A1 | 8/2005 | Rabiner et al. |
| 2005/0187514 A1 | 8/2005 | Rabiner et al. |
| 2005/0192556 A1 | 9/2005 | Soltani et al. |
| 2005/0192558 A1 | 9/2005 | Bernard et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0249667 A1 | 11/2005 | Tuszynski et al. |
| 2005/0256410 A1 | 11/2005 | Rabiner et al. |
| 2005/0277869 A1 | 12/2005 | Boukhny |
| 2005/0278633 A1 | 12/2005 | Kemp |
| 2005/0288695 A1 | 12/2005 | Jenson et al. |
| 2006/0069303 A1 | 3/2006 | Couvillon |
| 2006/0078555 A1 | 4/2006 | Hanley et al. |
| 2006/0094947 A1 | 5/2006 | Kovatchev et al. |
| 2006/0106308 A1 | 5/2006 | Hansmann et al. |
| 2006/0106375 A1 | 5/2006 | Werneth et al. |
| 2006/0116610 A1 | 6/2006 | Hare et al. |
| 2006/0142783 A1 | 6/2006 | Lewis et al. |
| 2006/0173387 A1 | 8/2006 | Hansmann et al. |
| 2006/0184070 A1 | 8/2006 | Hansmann et al. |
| 2006/0241462 A1 | 10/2006 | Chou et al. |
| 2006/0241524 A1 | 10/2006 | Lee et al. |
| 2006/0264758 A1 | 11/2006 | Hossack et al. |
| 2006/0264809 A1 | 11/2006 | Hansmann et al. |
| 2007/0005051 A1 | 1/2007 | Kampa |
| 2007/0005121 A1 | 1/2007 | Khanna |
| 2007/0016040 A1 | 1/2007 | Nita |
| 2007/0016041 A1 | 1/2007 | Nita |
| 2007/0037119 A1 | 2/2007 | Pal et al. |
| 2007/0038100 A1 | 2/2007 | Nita |
| 2007/0038158 A1 | 2/2007 | Nita et al. |
| 2007/0066900 A1 | 3/2007 | O'keeffe |
| 2007/0066978 A1 | 3/2007 | Schafer et al. |
| 2007/0083100 A1 | 4/2007 | Schulz-Stubner |
| 2007/0083120 A1 | 4/2007 | Cain et al. |
| 2007/0106203 A1* | 5/2007 | Wilson ............... A61N 7/00 604/22 |
| 2007/0112268 A1 | 5/2007 | Zhang et al. |
| 2007/0112296 A1 | 5/2007 | Wilson et al. |
| 2007/0123652 A1 | 5/2007 | Chu et al. |
| 2007/0129652 A1 | 6/2007 | Nita |
| 2007/0129761 A1 | 6/2007 | Demarais et al. |
| 2007/0142721 A1 | 6/2007 | Berner et al. |
| 2007/0149917 A1 | 6/2007 | Bennett et al. |
| 2007/0207194 A1 | 9/2007 | Grayburn et al. |
| 2007/0225619 A1 | 9/2007 | Rabiner et al. |
| 2007/0239027 A1 | 10/2007 | Nita |
| 2007/0249969 A1 | 10/2007 | Shields |
| 2007/0255252 A1 | 11/2007 | Mehta |
| 2007/0265560 A1 | 11/2007 | Soltani et al. |
| 2008/0045865 A1 | 2/2008 | Kislev |
| 2008/0065014 A1 | 3/2008 | Von Oepen et al. |
| 2008/0103417 A1 | 5/2008 | Soltani et al. |
| 2008/0109029 A1 | 5/2008 | Gurm |
| 2008/0115064 A1 | 5/2008 | Roach et al. |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Unger et al. |
| 2008/0208109 A1 | 8/2008 | Soltani et al. |
| 2008/0221506 A1 | 9/2008 | Rodriguez et al. |
| 2008/0228526 A1 | 9/2008 | Locke et al. |
| 2008/0235872 A1 | 10/2008 | Newkirk et al. |
| 2008/0249501 A1 | 10/2008 | Yamasaki |
| 2008/0262350 A1 | 10/2008 | Unger |
| 2008/0274097 A1 | 11/2008 | Tachibana et al. |
| 2008/0290114 A1 | 11/2008 | Cabuz et al. |
| 2008/0306499 A1 | 12/2008 | Katoh et al. |
| 2008/0312536 A1 | 12/2008 | Dala-Krishna |
| 2008/0315720 A1 | 12/2008 | Ma et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0073455 A1 | 3/2009 | Onimura |
| 2009/0079415 A1 | 3/2009 | Amada |
| 2009/0099482 A1 | 4/2009 | Furuhata et al. |
| 2009/0105597 A1 | 4/2009 | Abraham |
| 2009/0105633 A1 | 4/2009 | Tachibana et al. |
| 2009/0112150 A1 | 4/2009 | Unger et al. |
| 2009/0187137 A1 | 7/2009 | Volz et al. |
| 2009/0209900 A1 | 8/2009 | Carmeli et al. |
| 2009/0216246 A1 | 8/2009 | Nita et al. |
| 2009/0221902 A1 | 9/2009 | Myhr |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Soltani et al. |
| 2010/0125193 A1 | 5/2010 | Zadicario |
| 2010/0143325 A1 | 6/2010 | Gurewich |
| 2010/0160779 A1 | 6/2010 | Browning et al. |
| 2010/0160780 A1 | 6/2010 | Swan et al. |
| 2010/0196348 A1 | 8/2010 | Armstrong et al. |
| 2010/0204582 A1 | 8/2010 | Lu |
| 2010/0204642 A1 | 8/2010 | Wilson et al. |
| 2010/0210940 A1 | 8/2010 | Bradley et al. |
| 2010/0217276 A1 | 8/2010 | Garrison et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0280505 A1 | 11/2010 | Mattiuzzi et al. |
| 2010/0292685 A1 | 11/2010 | Katoh et al. |
| 2010/0317952 A1 | 12/2010 | Budiman et al. |
| 2010/0331645 A1 | 12/2010 | Simpson et al. |
| 2010/0332142 A1 | 12/2010 | Shadforth et al. |
| 2011/0004105 A1 | 1/2011 | Soltani et al. |

(56) References Cited

U.S. PATENT DOCUMENTS

| | | |
|---|---|---|
| 2011/0009720 A1 | 1/2011 | Kunjan et al. |
| 2011/0009739 A1 | 1/2011 | Phillips et al. |
| 2011/0034791 A1 | 2/2011 | Moerman |
| 2011/0112476 A1 | 5/2011 | Kauphusman et al. |
| 2011/0160621 A1 | 6/2011 | Nita |
| 2011/0200578 A1 | 8/2011 | Hanley et al. |
| 2011/0201974 A1 | 8/2011 | Soltani et al. |
| 2011/0264031 A1 | 10/2011 | Soltani et al. |
| 2011/0288449 A1 | 11/2011 | Schenkengel |
| 2011/0300078 A1 | 12/2011 | Borden et al. |
| 2011/0301506 A1 | 12/2011 | Volz |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0069285 A1 | 3/2012 | Koma et al. |
| 2012/0078140 A1 | 3/2012 | Nita |
| 2012/0089082 A1 | 4/2012 | Zhang et al. |
| 2012/0095389 A1 | 4/2012 | Bennett et al. |
| 2012/0123273 A1 | 5/2012 | Okuno et al. |
| 2012/0172795 A1 | 7/2012 | Sandhu et al. |
| 2012/0172858 A1 | 7/2012 | Harrison et al. |
| 2012/0179073 A1 | 7/2012 | Nita |
| 2012/0197277 A1 | 8/2012 | Stinis |
| 2012/0203201 A1 | 8/2012 | Ginsburg et al. |
| 2012/0209116 A1 | 8/2012 | Hossack et al. |
| 2012/0253237 A1 | 10/2012 | Wilson et al. |
| 2012/0265123 A1 | 10/2012 | Khanna |
| 2012/0271203 A1 | 10/2012 | Soltani et al. |
| 2012/0271223 A1 | 10/2012 | Khanna |
| 2012/0289889 A1 | 11/2012 | Genstler et al. |
| 2012/0330141 A1 | 12/2012 | Brown et al. |
| 2012/0330144 A1 | 12/2012 | Brown et al. |
| 2012/0330196 A1 | 12/2012 | Nita |
| 2013/0073306 A1 | 3/2013 | Shlain et al. |
| 2013/0204166 A1 | 8/2013 | Villanueva et al. |
| 2013/0211316 A1 | 8/2013 | Wilcox et al. |
| 2013/0216593 A1 | 8/2013 | Borden et al. |
| 2013/0289398 A1 | 10/2013 | Borden et al. |
| 2013/0331738 A1 | 12/2013 | Borrelli |
| 2014/0046313 A1* | 2/2014 | Pederson ............ A61B 17/2202 606/28 |
| 2014/0128734 A1 | 5/2014 | Genstler et al. |
| 2014/0155814 A1 | 6/2014 | Bennett et al. |
| 2014/0210631 A1 | 7/2014 | Zavis |
| 2014/0226901 A1 | 8/2014 | Spracklen et al. |
| 2014/0236005 A1 | 8/2014 | Chen et al. |
| 2014/0236118 A1 | 8/2014 | Unser et al. |
| 2014/0249453 A1 | 9/2014 | Wilson et al. |
| 2014/0276367 A1 | 9/2014 | Kersten et al. |
| 2014/0316329 A1 | 10/2014 | Soltani et al. |
| 2014/0343483 A1 | 11/2014 | Zhang et al. |
| 2015/0095807 A1 | 4/2015 | Duncker et al. |
| 2015/0173673 A1* | 6/2015 | Toth ................... A61B 18/1492 600/300 |
| 2015/0178044 A1 | 6/2015 | Ehlen et al. |
| 2016/0030725 A1 | 2/2016 | Kersten et al. |
| 2016/0082243 A1 | 3/2016 | Genstler et al. |
| 2016/0262777 A1* | 9/2016 | Stigall ..................... A61N 7/00 |
| 2016/0361528 A1 | 12/2016 | Kanz et al. |
| 2017/0007815 A1 | 1/2017 | Wilson et al. |
| 2017/0182302 A1 | 6/2017 | Kersten et al. |
| 2018/0206867 A1 | 7/2018 | Allen |
| 2019/0054274 A1* | 2/2019 | King ....................... A61B 5/062 |
| 2019/0091458 A1 | 3/2019 | Wilson et al. |
| 2019/0099591 A1 | 4/2019 | Genstler et al. |
| 2019/0216477 A1 | 7/2019 | Soltani et al. |
| 2019/0223894 A1 | 7/2019 | Soltani et al. |
| 2019/0223895 A1 | 7/2019 | Volz |
| 2019/0269944 A1 | 9/2019 | Soltani et al. |

FOREIGN PATENT DOCUMENTS

| | | |
|---|---|---|
| CN | 1193267 A | 9/1998 |
| CN | 1309331 A | 8/2001 |
| CN | 1358988 A | 7/2002 |
| CN | 1720874 A | 1/2006 |
| CN | 301040544 S | 10/2009 |
| CN | 301877182 S | 4/2012 |
| CN | 102548603 A | 7/2012 |
| DE | 3919592 A1 | 2/1990 |
| DE | 4005743 A1 | 8/1991 |
| EP | 108658 A1 | 5/1984 |
| EP | 122624 A2 | 10/1984 |
| EP | 189329 A2 | 7/1986 |
| EP | 224934 A2 | 6/1987 |
| EP | 278074 A2 | 8/1988 |
| EP | 327490 A1 | 8/1989 |
| EP | 0338971 A1 | 10/1989 |
| EP | 495531 A1 | 7/1992 |
| EP | 504881 A2 | 9/1992 |
| EP | 520486 A2 | 12/1992 |
| EP | 0529675 A2 | 3/1993 |
| EP | 0586875 A1 | 3/1994 |
| EP | 617913 A1 | 10/1994 |
| EP | 625360 A1 | 11/1994 |
| EP | 629382 A1 | 12/1994 |
| EP | 634189 A2 | 1/1995 |
| EP | 668052 A2 | 8/1995 |
| EP | 670147 A1 | 9/1995 |
| EP | 732106 A2 | 9/1996 |
| EP | 744189 A1 | 11/1996 |
| EP | 0746245 A2 | 12/1996 |
| EP | 788774 A1 | 8/1997 |
| EP | 1090658 A1 | 4/2001 |
| EP | 1103281 A2 | 5/2001 |
| EP | 1145731 A2 | 10/2001 |
| EP | 1252885 A2 | 10/2002 |
| EP | 1453425 A2 | 9/2004 |
| EP | 1463454 A1 | 10/2004 |
| EP | 1595576 A1 | 11/2005 |
| EP | 1647232 A2 | 4/2006 |
| EP | 2015846 A2 | 1/2009 |
| EP | 2170181 A1 | 4/2010 |
| EP | 2231024 A1 | 9/2010 |
| EP | 2448636 A1 | 5/2012 |
| EP | 2494932 A2 | 9/2012 |
| EP | 2608730 A2 | 7/2013 |
| EP | 2727544 A1 | 5/2014 |
| GB | 1577551 A | 10/1980 |
| JP | 5211591 A | 9/1977 |
| JP | 5856869 A | 4/1983 |
| JP | 5963783 A | 4/1984 |
| JP | 59108378 A | 6/1984 |
| JP | 61244079 A | 10/1986 |
| JP | 02180275 A | 7/1990 |
| JP | 03063041 A | 3/1991 |
| JP | 03170172 A | 7/1991 |
| JP | 03176077 A | 7/1991 |
| JP | 03221421 A | 9/1991 |
| JP | 06233779 A | 8/1994 |
| JP | 08243168 A | 9/1996 |
| JP | 2001228601 A | 8/2001 |
| JP | 2001340336 A | 12/2001 |
| JP | 2002501402 A | 1/2002 |
| JP | 2002136537 A | 5/2002 |
| JP | 2002519095 A | 7/2002 |
| JP | 2003509152 A | 3/2003 |
| JP | 2005512630 A | 5/2005 |
| JP | 2006055649 A | 3/2006 |
| JP | 2006510449 A | 3/2006 |
| JP | 2007520281 A | 7/2007 |
| JP | 2009508630 A | 3/2009 |
| JP | D1456367 S | 11/2012 |
| SU | 614788 A1 | 7/1978 |
| SU | 654254 A2 | 3/1979 |
| SU | 931191 A1 | 5/1982 |
| SU | 1003853 A1 | 3/1983 |
| SU | 1103863 A1 | 7/1984 |
| SU | 1146059 A1 | 3/1985 |

(56) References Cited

FOREIGN PATENT DOCUMENTS

| | | |
|---|---|---|
| SU | 1648497 A1 | 5/1991 |
| WO | 80001365 A1 | 7/1980 |
| WO | 08002365 A1 | 11/1980 |
| WO | 89004142 A1 | 5/1989 |
| WO | 89005159 A1 | 6/1989 |
| WO | 89005160 A1 | 6/1989 |
| WO | 89006978 A1 | 8/1989 |
| WO | 90001300 A1 | 2/1990 |
| WO | 90001971 A1 | 3/1990 |
| WO | 91003264 A1 | 3/1991 |
| WO | 91009629 A1 | 7/1991 |
| WO | 91012772 A1 | 9/1991 |
| WO | 91019529 A1 | 12/1991 |
| WO | 92000113 A1 | 1/1992 |
| WO | 92007622 A1 | 5/1992 |
| WO | 93008738 A1 | 5/1993 |
| WO | 94005361 A1 | 3/1994 |
| WO | 94005368 A1 | 3/1994 |
| WO | 94017734 A1 | 8/1994 |
| WO | 94028873 A1 | 12/1994 |
| WO | 95001751 A1 | 1/1995 |
| WO | 95005866 A1 | 3/1995 |
| WO | 95009572 A1 | 4/1995 |
| WO | 95010233 A1 | 4/1995 |
| WO | 95015118 A1 | 6/1995 |
| WO | 9526777 A1 | 10/1995 |
| WO | 9527443 A1 | 10/1995 |
| WO | 9604955 A2 | 2/1996 |
| WO | 9607432 A1 | 3/1996 |
| WO | 9615815 A1 | 5/1996 |
| WO | 9627341 A1 | 9/1996 |
| WO | 9629935 A1 | 10/1996 |
| WO | 9635469 A1 | 11/1996 |
| WO | 9636286 A1 | 11/1996 |
| WO | 9639079 A1 | 12/1996 |
| WO | 9707735 A1 | 3/1997 |
| WO | 9719644 A1 | 6/1997 |
| WO | 9719645 A1 | 6/1997 |
| WO | 9721462 A1 | 6/1997 |
| WO | 9727808 A1 | 8/1997 |
| WO | 9740679 A1 | 11/1997 |
| WO | 9809571 A1 | 3/1998 |
| WO | 9811826 A1 | 3/1998 |
| WO | 9818391 A1 | 5/1998 |
| WO | 9829055 A2 | 7/1998 |
| WO | 9840016 A2 | 9/1998 |
| WO | 9848711 A1 | 11/1998 |
| WO | 9856462 A1 | 12/1998 |
| WO | 9858699 A1 | 12/1998 |
| WO | 9916360 A1 | 4/1999 |
| WO | 9925385 A1 | 5/1999 |
| WO | 9932184 A1 | 7/1999 |
| WO | 9933500 A2 | 7/1999 |
| WO | 9933550 A1 | 7/1999 |
| WO | 9934858 A1 | 7/1999 |
| WO | 9939647 A1 | 8/1999 |
| WO | 9939738 A1 | 8/1999 |
| WO | 9942039 A1 | 8/1999 |
| WO | 9944512 A1 | 9/1999 |
| WO | 00000095 A1 | 1/2000 |
| WO | 00012004 A1 | 3/2000 |
| WO | 00018468 A1 | 4/2000 |
| WO | 00038580 A1 | 7/2000 |
| WO | 00069341 A1 | 11/2000 |
| WO | 01013357 A1 | 2/2001 |
| WO | 0121081 A1 | 3/2001 |
| WO | 01054754 A1 | 8/2001 |
| WO | 01074255 A1 | 10/2001 |
| WO | 01087174 A1 | 11/2001 |
| WO | 01095788 A2 | 12/2001 |
| WO | 0213678 A2 | 2/2002 |
| WO | 0215803 A1 | 2/2002 |
| WO | 0215804 A1 | 2/2002 |
| WO | 03007649 A2 | 1/2003 |
| WO | 03051208 A1 | 6/2003 |
| WO | 03099382 A1 | 12/2003 |
| WO | 2004058045 A2 | 7/2004 |
| WO | 2005027756 A1 | 3/2005 |
| WO | 2005072391 A2 | 8/2005 |
| WO | 2005072409 A2 | 8/2005 |
| WO | 2005079415 A2 | 9/2005 |
| WO | 2005084552 A1 | 9/2005 |
| WO | 2005084553 A1 | 9/2005 |
| WO | 2006110773 A2 | 10/2006 |
| WO | 2007127176 A2 | 11/2007 |
| WO | 2008052186 A2 | 5/2008 |
| WO | 2008086372 A1 | 7/2008 |
| WO | 2009002881 A1 | 12/2008 |
| WO | 2009018472 A1 | 2/2009 |
| WO | 2009079415 A1 | 6/2009 |
| WO | 2010003130 A2 | 1/2010 |
| WO | 2011003031 A1 | 1/2011 |
| WO | 2011011539 A1 | 1/2011 |
| WO | 2011056311 A1 | 5/2011 |
| WO | 2012027722 A2 | 3/2012 |
| WO | 2014159274 A1 | 10/2014 |
| WO | 2015074036 A2 | 5/2015 |
| WO | WO-2015074036 A2 * | 5/2015 ......... A61B 17/2202 |
| WO | 2016201136 A1 | 12/2016 |

OTHER PUBLICATIONS

Akdemir et al., "Treatment of Severe Intraventricular Hemorrhage by Intraventricular Infusion of Urokinase", Neurosurgical Review, 1995, vol. 18, No. 2, pp. 95-100.
Akhtar, "Anti-HIV Therapy With Antisense Oligonucleotides and Ribozymes: Realistic Approaches or Expensive Myths?" Antimicrob Chemother, 1996, vol. 2, pp. 159-165.
Anderson, "Human Gene Therapy," Nature, 1998, vol. 392, pp. 25-30.
Butler, "Production of Microbubbles for Use as Echo Contrast Agents", Journal of Clinical Ultrasound, Jun. 1986, vol. 14, pp. 408-412.
Bleeker et al., "On the Application of Ultrasonic Contrast Agents for Blood Flowmetry and Assessment of Cardiac Perfusion", Journal of Ultrasound in Medicine, Aug. 1990, vol. 9, No. 8, pp. 461-471.
Branch, Andrea D., "A Good Antisense Molecule is Hard to Find", Trends in Biochem Science 23, Feb. 1998, pp. 45-50.
Bao et al. "Transfection of a Reporter Plasmid into Cultured Cells by Sonoporation In Vitro," Ultrasound in Medicine and Biology Journal, 1997, vol. 23, No. 6, pp. 953-959.
Broderick et al., "Guidelines for the Management of Spontaneous Intracerebral Hemorrhage: a Statement for Healthcare Professionals From a Special Writing Group of the Stroke Council, American Heart Association", Stroke, Journal of the American Heart Association, 1999, pp. 905-915.
Tachibana et al., "Liver tissue damage by ultrasound in combination with the photosensitizing drug, Photofrin II," Cancer Letters, vol. 78, (1-3), 1994, pp. 177-181.
Tachibana et al., "Enhancement of Cell killing of HL-60 cells by ultrasound in the presence of the photosensitizing drug Photofrin II," Cancer Letters, vol. 72, 1993, pp. 195-199.
Chamsuddin et al., "Catheter-directed Thrombolysis with the Endowave System in the Treatment of Acute Massive Pulmonary Embolism: a Retrospective Multicenter Case Series," Journal of Vascular and Interventional Radiology, Mar. 2008, vol. 19, No. 3, pp. 372-376.
U.S. Appl. No. 10/291,890, filed Nov. 7, 2002.
Crooke, Basic Principles of Antisense Therapeutics, Springer-Verlag, Eds, New York, 1998, pp. 1 and 4.
Deinsberger et al., "Stereotactic Aspiration and Fibrinolysis of Spontaneous Supratentorial Intracerebral Hematomas versus Conservative Treatment: a Matched-Pair Study", Zentralblatt für Neurochirurgie, Dec. 18, 2003, vol. 64, No. 4, pp. 145-150.
"EkoSonic® MACH4e", EKOS Advertisement, Venous Times, Issue 6, dated Jan. 2010, p. 3.
Fechmeier et al. "Transfection of Mammalian Cells with Plasid DNA by Scrape Loading and Sonication Loading," Proc. Natl. Acad. Sci. USA, Dec. 1987, vol. 84, pp. 8463-8467.

(56) References Cited

OTHER PUBLICATIONS

Feinstein et al., "Two-dimensional Contrast Echocardiography. I. In Vitro Development and Quantitative Analysis of Echo Contrast Agents", Journal of the American College of Cardiology, Jan. 1984, vol. 3, No. 1, pp. 14-20.
Feldman et al. "Optimal Techniques for Arterial Gene Transfer," Cardiovascular Research, 1997, vol. 35, pp. 391-404.
Findlay et al., "Lysis of Intraventricular Hematoma with Tissue Plasminogen Activator", Journal of Neurosurgery, 1991, vol. 74, pp. 803-807.
Frémont et al., "Prognostic Value of Echocardiographic Right/Left Ventricular End-Diastolic Diameter Ratio in Patients With Acute Pulmonary Embolism: Results From a Monocenter Registry of 1,416 Patients", Chest, Feb. 2008, vol. 133, No. 2, pp. 358-362.
Gilles et al., "Cavitation Generated by Amplitude Modulated HIFU: Investigations on the Inertial Cavitation Threshold," AIP Conference Proceedings: 6th Int. Symposium on Theraputic Ultrasound, May 21, 2007, vol. 911, pp. 171-177.
Greenleaf, William J. et al.; Arlifical Cavitation Nuclei Significantly Enhance Acoustically Induced Cell Transfection. vol. 24, No. 4 pp. 587-595, 1998.
Ho et al. "Antisense Oigonucleoties and Therapeutics for Malignant Diseases," Seminars in Drug Discovery 24, 1997, vol. 2, pp. 187-202.
Holland et al., "Thresholds for Transient Cavitation Produced by Pulsed Ultrasound in a Controlled Nuclei Environment", The Journal of the Acoustical Society of America, Nov. 1990, vol. 88, No. 5, pp. 2059-2069.
Hynynen et al.; "Small Cylindrical Ultrasound Sources for Induction of Hyperthermia via Body Cavities or Interstitial Implants", Arizona Cancer Center and Department of Radiation Oncology, University of Arizona Health Sciences Center; vol. 9, No. 2, 1993, pp. 263-274.
Jaff et al., "Management of Massive and Submassive Pulmonary Embolism, Iliofemoral Deep Vein Thrombosis, and Chronic Thromboembolic Pulmonary Hypertension: a Scientific Statement From the American Heart Association", Challenging Forms of Venous Thromboembolic Disease, Circulation, 2011, vol. 123, pp. 1788-1830.
Japanese Journal of Cancer Research, vol. 81, No. 3, Mar. 1990, pp. 304-308.
Jeffers, R.J. et al.; Evaluation of the Effect of Cavitation Activity on Drug-Ultrasound Synergisms, 1993.
Jeffers, Russel et al.; Dimethylformamide as an Enhancer of Cavitation-Induced Cell Lysis In Vitro, vol. 97, No. 1, Jan. 1995.
Keller et al., "Automated Production and Analysis of Echo Contrast Agents", Journal of Ultrasound in Medicine, Sep. 1986, vol. 5, pp. 493-498.
Kim et al. "Ultra-sound Mediated Transfection of Mammalian Cells," Human Gene Therapy, Jul. 10, 1996, vol. 7, pp. 1339-1346.
Kim, Timothy F., "Microbubbles Show Promise for Enhancing Ultrasound Signal, Image, Other Applications", The Journal of the American Medical Association, Mar. 1989, vol. 281, No. 11, p. 1542.
Kotnis et al. "Optimisation of Gene Transfer into Vascular Endothelial Cells Using Electroporation," Eur J. Vasc Surg, 1995, vol. 9, pp. 71-79.
Kucher et al., "Randomized, Controlled Trial of Ultrasound-Assisted Catheter-Directed Thrombolysis for Acute Intermediate-Risk Pulmonary Embolism", Ultrasound Thrombolysis for Pulmonary Embolism, Circulation, 2014, vol. 129, pp. 479-486.
Lang et al., "Contrast Ultrasonography of the Kidney: a New Method for Evaluation of Renal Perfusion in Vivo", Circulation, 1987, vol. 75, No. 1, pp. 229-234.
Lee et al.; "Arrays of Multielement Ultrasound Applicators for Interstitial Hyperthermia"; IEEE Transactions on biomedical Engineering; vol. 46, No. 7, Jul. 1999, pp. 880-890.
Leong et al., "Polyanhydrides for Controlled Release of Bioactive Agents", Biomaterials, Sep. 1986, vol. 7, pp. 364-371.

Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.
Matsumoto et al., "CT-Guided Stereotaxic Evacuation of Hypertensive Intracerebral Hematomas", Journal of Neurosurgery, Sep. 1984, vol. 61, No. 3, pp. 440-448.
Mayfrank et al., "Fibrinolytic Treatment of Intraventricular Haemorrhage Preceding Surgical Repair of Ruptured Aneurysms and Arteriovenous Malformations", British Journal of Neurosurgery, 1999, vol. 13, No. 2, pp. 128-131.
Maywald et al., "Experience With Atraumatic Vascular Diagnosis With the Aid of the Ultrasonic Doppler Technique", Electromedica, 1976, vol. 2 pp. 43-48.
Meltzer et al., "The Source of Ultrasound Contrast Effect", Journal of Clinical Ultrasound, Apr. 1980, vol. 8, No. 2, pp. 121-127.
Meyer et al., "Fibrinolysis for Patients with Intermediate-Risk Pulmonary Embolism", N. Engl. J. Med., 2014, vol. 340, pp. 1402-1411.
Miller, Douglas L. et al.; Sonoporation of Cultured Cells in the Rotation Tube Exposure System, vol. 25, No. 1, 1999.
Mohadjer et al., "CT-Guided Stereotactic Fibrinolysis of Spontaneous and Hypertensive Cerebellar Hemorrhage: Long-Term Results", Journal of Neurosurgery, Aug. 1990, vol. 73, No. 2, pp. 217-222.
Niizuma et al., "CT-Guided Stereotactic Aspiration of Intracerebral Hematoma—Result of a Hematoma-Lysis Method Using Urokinase", Applied Neurophysiology, Proceedings of the Ninth Meeting of the World Society, Jul. 4-7, 1985, pp. 4.
Niizuma et al., "Results of Stereotactic Aspiration in 175 Cases of Putaminal Hemorrhage", Neurosurgery, Jun. 1989, vol. 24, No. 6, pp. 814-819.
Orkin et al., Report and Recommendations of the Panel to Assess the NIH Investment in Research on Gene Therapy, Dec. 7, 1995, pp. 1-38.
Pang et al., "Lysis of Intraventricular Blood Clot with Urokinase in a Canine Model: Part 1", Neurosurgery, 1986, vol. 19, No. 4, pp. 540-546.
"Photophoresis Apparatus in Treatment of a Cutis T Cell Lymphadenoma," Science (Japan Edition), Oct. 1988, pp. 65-73.
Porter et al. "Interaction of Diagnostic Ultrasound with Synthetic Olionucleotide-Labeled Perfluorcarbon-Exposed Sonicated Dextrose Albumin Microbubbles," J Ultrasound Med, 15:557-584, 1996.
Porter et al., Thrombolytic Enhancement With Perfluorocarborn-Exposed Sonicated Dextrose Albumin Microbubbles, Nov. 1996.
Prat et al., "In Vivo Effects of Cavitation Alone or in Combination with Chemotherapy in a Peritoneal Carcinomatosis in the Rat," 1993, vol. 68, pp. 13-17.
Price et al.; Delivery of Colloidal Particles and Red Blood Cells to Tissue Through Microvessel Ruptures Created by Targeted Microbubble Destruction With Ultrasound, Sep. 29, 1998.
Rohde et al., "Intraventricular Recombinant Tissue Plasminogen Activator for Lysis of Intraventricular Haemorrhage", Journal of Neurology and Neurosurgery Psychiatry, 1995, vol. 58, pp. 447-451.
Romano et al., Latest Developments in Gene Transfer Technology: Achievements, Perspectives, and Controversies over Therapeutice Applications, (Stem Cells 18: 19-39, 2000).
Rosenschein et al., "Experimental Ultrasonic Angioplasty: Disruption of Atherosclerotic Plaques and Thrombi in Vitro and Arterial Recanalization in Vivo," Journal of the American College of Cardiology, Mar. 1, 1990, vol. 15, No. 3, pp. 711-717.
Saletes et al., "Acoustic Cavitation Generated by BiFrequency Excitation" University De Lyon, Dec. 2009.
Saletes et al., "Cavitation par Excitation Acoustique Bifréquentielle: Application á la Thrombolyse Ultrsonore," N' d'ordre 311, Universite de Lyon, Dec. 7, 2009, pp. 110.
Saletes et al., "Efficacité d'une Excitation Bifréquentielle en Thrombolyse Purement Ultrsonore," 10éme Congrés Français d'Acoustique, Universite de Lyon, Apr. 12-16, 2010.
Schäfer et al., "Influence of Ultrasound Operating Parameters on Ultrasound-Induced Thrombolysis In Vitro," Ultrasound in Medicine and Biology, vol. 31, No. 6, Mar. 2005, pp. 841-847.

(56) References Cited

OTHER PUBLICATIONS

Schaller et al., "Stereotactic Puncture and Lysis of Spontaneous Intracerebral Hemorrhage Using Recombinant Tissue-Plasminogen Activator", Neurosurgery, Feb. 1995, vol. 36, No. 2, pp. 328-335.
Somia et al., "Gene Therapy: Trials and Tribulations," Nature Reviews Genetics, 2000, vol. 1, pp. 91-99.
Tachibana K.; Albumin Microbubble Echo-Contrast Materials as an Enhancer for Ultrasound Accelerated Thrombolysis, Sep. 1, 1995.
Tachibana, "Enhancement of Fibrinolysis with Ultrasound Energy", JVIR, vol. 3, No. 2, May 1992, pp. 299-303.
Teernstra et al., "Stereotactic Treatment of Intracerebral Hematoma by Means of a Plasminogen Activator. A Multicenter Randomized Controlled Trial (SICHPA", Stroke, Journal of the American Heart Association, Mar. 20, 2003, pp. 968-974.
Tsetis et al., "Potential Benefits From Heating the High-Dose Rtpa Boluses Used in Catheter-Directed Thrombolysis for Acute/Subacute Lower Limb Ischemia", Journal of Endovascular Therapy, 2003, vol. 10, pp. 739-744.
Tsurumi, et al. "Direct Intramuscular Gene Transfer of Naked DNA Encoding Vascular Endothelial Growth Factor Augments Collateral Development and Tissue Perfusion," Circulation, 1996; 94: 3281-3290.
Unger et al., "Ultrasound Enhances Gene Expression of Liposomal Transfection," Investigative Radiology, vol. 32, No. 12, pp. 723-727, 1997.
Unger et al., "Acoustically Active Liposheres Containing Paclitaxel," vol. 11, No. 12, 1992.
Vandenburg et al., "Myocardial Risk Area and Peak Gray Level Measurement by Contrast Echocardiography: Effect of Microbubble Size and Concentration, Injection Rate, and Coronary Vasodilation," American Heart Journal, Apr. 1988, vol. 115, No. 4, pp. 733-739.
Verma et al., "Gene Therapy—Promises, Problems and Prospects," Nature, 1997, vol. 389, pp. 239-242.
Wheatly et al., "Contrast Agents for Diagnostic Ultrasound: Development and Evaluation of Polymer-Coated Microbubbles," Biomaterials, Nov. 1990, vol. 11, No. 19, pp. 713-717.
Wu, Yunqiu et al., "Binding as Lysing of Blood Clots Using MRX-408," Investigative Radiology, Dec. 1998, vol. 33, No. 12, pp. 880-885.
Wyber et al., "The Use of Sonication for the Efficient Delivery of Plasmid DNA into Cells," Pharmaceutical Research, vol. 14, No. 6, pp. 750-756.
Yumita et al., "Synergistic Effect of Ultrasound and Hematoporphyrin on Sarcoma 180", Japanese Journal of Cancer Research, vol. 81, No. 3, Mar. 1990, pp. 304-308.

\* cited by examiner

A-A

B-B

B-B

C-C

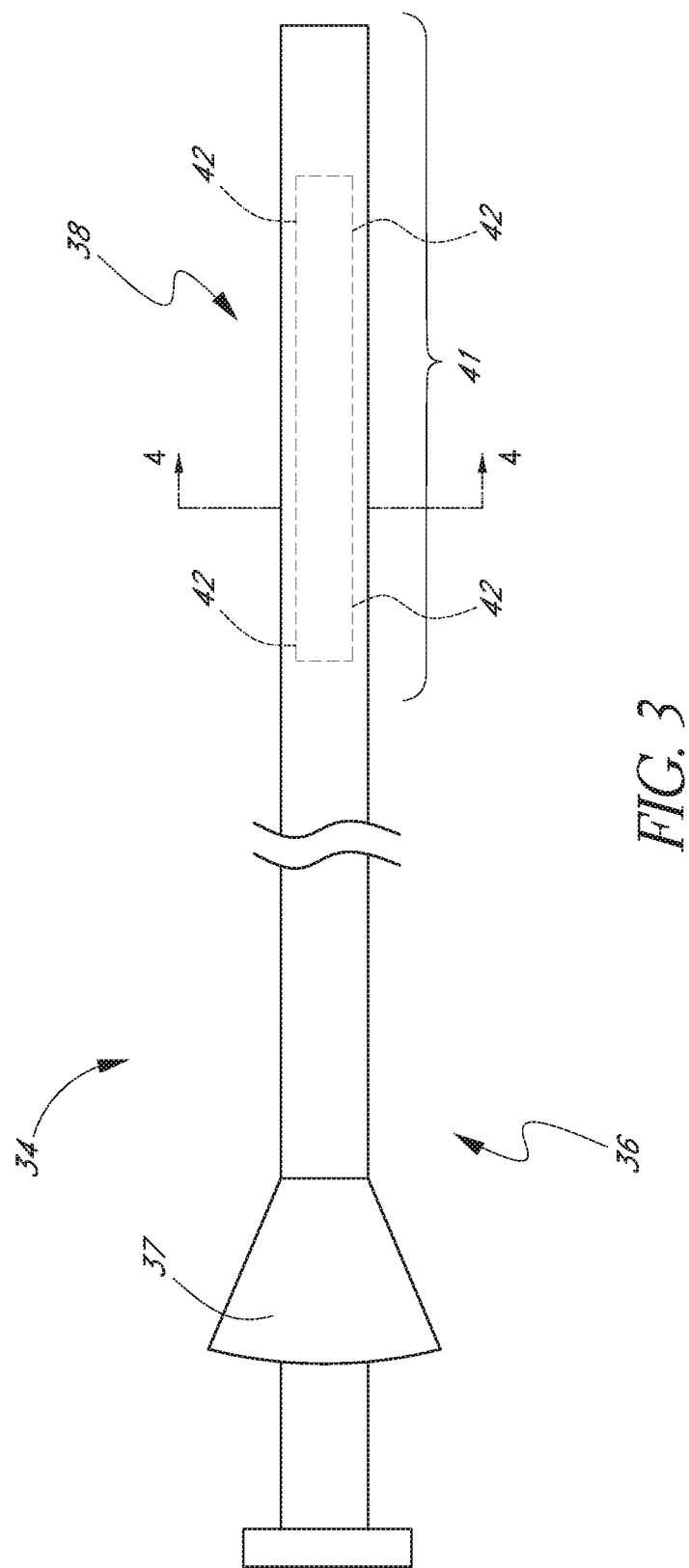

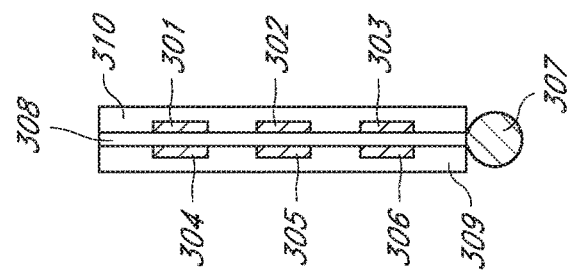
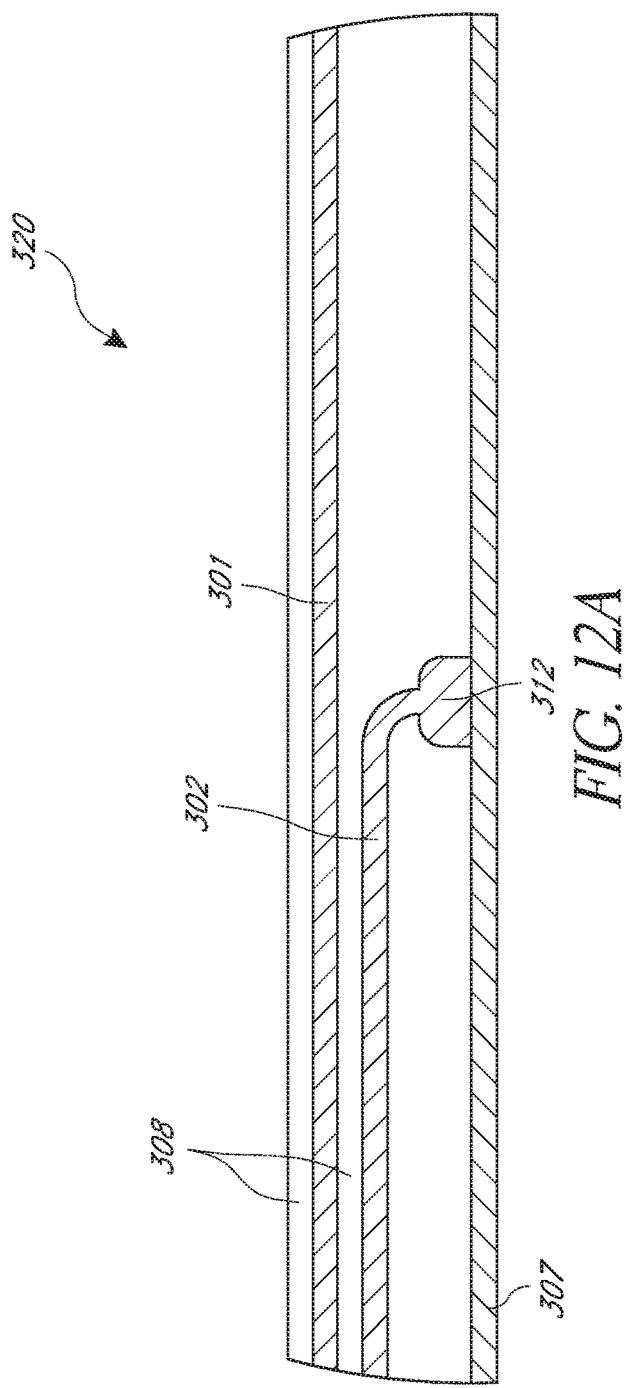
FIG. 12B
FIG. 12A

ULTRASOUND CATHETER

CROSS-REFERENCE TO RELATED APPLICATIONS

This application is a continuation of U.S. application Ser. No. 15/178,398 filed Jun. 9, 2016, now U.S. Pat. No. 10,495,520; which claims the benefit of priority to U.S. Provisional Application No. 62/173,863, filed Jun. 10, 2015, the entirety of which are herein incorporated by reference.

FIELD

The present disclosure relates generally to an ultrasonic catheter and more specifically to an ultrasonic catheter configured to deliver ultrasonic energy and a therapeutic compound to a treatment site.

BACKGROUND

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site within a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing therapeutic compounds directly to the occlusion site. Ultrasonic energy generated by the ultrasound assembly enhances the effect of the therapeutic compounds. Such a device can be used in the treatment of diseases such as peripheral arterial occlusion, deep vein thrombosis or acute ischemic stroke. In such applications, the ultrasonic energy enhances treatment of the occlusion with therapeutic compounds such as urokinase, tissue plasminogen activator ("tPA"), recombinant tissue plasminogen activator ("rtPA") and the like. Further information on enhancing the effect of a therapeutic compound using ultrasonic energy is provided in U.S. Pat. Nos. 5,318,014, 5,362,309, 5,474,531, 5,628,728, 6,001,069, 6,210,356 and 7,341,569.

Another use for ultrasonic catheters is in the treatment of pulmonary embolisms. Pulmonary embolisms ("PE") are caused when a large blood clot obstructs the major blood vessels leading from the heart to the lungs. The victim's heart can be suddenly overwhelmed with the task of pushing blood past this obstruction. About 5% of PEs are classified as massive and can result in rapid heart failure, shock and death without immediate therapy. Such massive PEs have traditionally been treated by a large dose of clot-dissolving drug (i.e., a thrombolytic). However, such treatment can result in unintended bleeding and even fatalities. Up to 40% of PEs are less critical obstructions, often called sub-massive PE. Current treatment protocols include treatment with anti-coagulant medication. Such treatments do not remove the clot but simply prevent the clot from growing larger. Recent studies suggest that failure to remove these sub-massive clots may have long-term adverse consequences including recurrent PE, chronic pulmonary hypertension and death.

SUMMARY

In some embodiments, disclosed is an ultrasound catheter that includes a first tubular body having a first longitudinal axis extending centrally through the tubular body, the first tubular body including at least one delivery port extending through a wall of the first tubular body. In some embodiments, the ultrasound catheter includes a second tubular body having a second longitudinal axis extending centrally through the second tubular body, the first and second longitudinal axes being displaced from each other such that an asymmetrical longitudinally extending gap is formed between an outer surface of the second tubular body and an interior surface of the first tubular body. In some embodiments, the ultrasound catheter includes a temperature sensor forming a thermocouple extending longitudinally within the gap between the first tubular body and the second tubular body. In some embodiments, the disclosure includes an inner core positioned within the second tubular body, the inner core comprising at least one ultrasound element. In certain embodiments, the temperature sensor comprises a flexible circuit. In certain embodiments, the temperature sensor comprises a plurality of filament pairs wherein each of the filaments is insulated; and a plurality of thermocouples wherein each of the plurality of thermocouples are formed between each of the plurality of filament pairs.

In some embodiments, disclosed is a method of manufacturing a catheter. In some embodiments, the method includes inserting an inner tubular body into an outer tubular body. In some embodiments, the method includes placing a temperature sensor between the outer and inner tubular body, wherein the temperature sensor is adjacent to an outer surface of the inner tubular body such that the inner tubular body does not extend along the same longitudinal axis a the outer tubular body. In certain embodiments, the temperature sensor comprises a flexible circuit. In certain embodiments, the temperature sensor comprises a plurality of filament pairs wherein each of the filaments is insulated; and a plurality of thermocouples wherein each of the plurality of thermocouples are formed between each of the plurality of filament pairs.

In some embodiments, disclosed is an ultrasound catheter including an elongate inner tubular body. In some embodiments, the ultrasound catheter includes an elongate outer tubular wherein the elongate inner tubular body is positioned within the elongate outer tubular body to form an asymmetrical gap between an outer surface of the inner tubular body and an interior surface of the elongate outer tubular body to form a fluid delivery lumen. In some embodiments, the ultrasound catheter includes a temperature sensor extending along the outer surface of the inner tubular body within the gap. In some embodiments, the ultrasound catheter includes an inner core positioned within the inner tubular body and comprising at least one ultrasound element. In certain embodiments, the temperature sensor comprises a flexible circuit. In certain embodiments, the temperature sensor comprises a plurality of filament pairs wherein each of the filaments is insulated; and a plurality of thermocouples wherein each of the plurality of thermocouples are formed between each of the plurality of filament pairs.

In some embodiments, disclosed is a method of manufacturing a catheter including inserting an inner tubular body into an outer tubular body. In some embodiments, the method of manufacturing includes placing a temperature sensor between the outer and inner tubular body, wherein the temperature sensor is adjacent to an outer surface of the inner tubular body such that the inner tubular body does not extend along the same longitudinal axis a the outer tubular body. In certain embodiments, the temperature sensor comprises a flexible circuit. In certain embodiments, the temperature sensor comprises a plurality of filament pairs wherein each of the filaments is insulated; and a plurality of thermocouples wherein each of the plurality of thermocouples are formed between each of the plurality of filament pairs.

In some embodiments, disclosed is an ultrasound catheter including an elongate inner tubular body. In some embodiments, the ultrasound catheter includes an elongate outer tubular wherein the elongate inner tubular body is positioned within the elongate outer tubular body to form an asymmetrical gap between an outer surface of the inner tubular body and an interior surface of the elongate outer tubular body to form a fluid delivery lumen. In some embodiments, the ultrasound catheter includes a temperature sensor extending along the outer surface of the inner tubular body within the gap. In some embodiments, the ultrasound catheter includes an inner core positioned within the inner tubular body and comprising at least one ultrasound element.

In some embodiments, disclosed is a flexible circuit for a catheter. In some embodiments, the flexible circuit includes a plurality of traces formed on the flexible circuit separated by insulating material. In some embodiments, the plurality of traces includes at least two traces of a first material connected to a single trace of second dissimilar material at different points along a length of the flexible circuit. In some embodiments, a temperature sensor for a catheter comprises a plurality of filament pairs wherein each of the filaments is insulated; and a plurality of thermocouples wherein each of the plurality of thermocouples are formed between each of the plurality of filament pairs.

For purposes of summarizing the invention and the advantages achieved over the prior art, certain objects and advantages of the invention have been described in this application. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the embodiments having reference to the attached figures, the invention not being limited to any particular embodiment(s) disclosed.

BRIEF DESCRIPTION OF THE DRAWINGS

Exemplary embodiments of the vascular occlusion treatment system are illustrated in the accompanying drawings, which are for illustrative purposes only. The drawings comprise the following figures, in which like numerals indicate like parts.

FIG. 3 is a schematic illustration of an elongate inner core configured to be positioned within the central lumen of the catheter illustrated in FIG. 2.

FIG. 12A is a horizontal cross-section showing a top view of another embodiment of a flexcircuit, with protective second coverlay 310 removed, that can be configured to form a thermocouple to serve as a temperature sensor in the ultrasonic catheter illustrated in FIGS. 1A-E.

FIG. 12B is a vertical cross-sectional view of the embodiment of the flexcircuit illustrated in FIG. 12A at a more proximal point.

DETAILED DESCRIPTION OF THE PREFERRED EMBODIMENTS

Figure 1A:
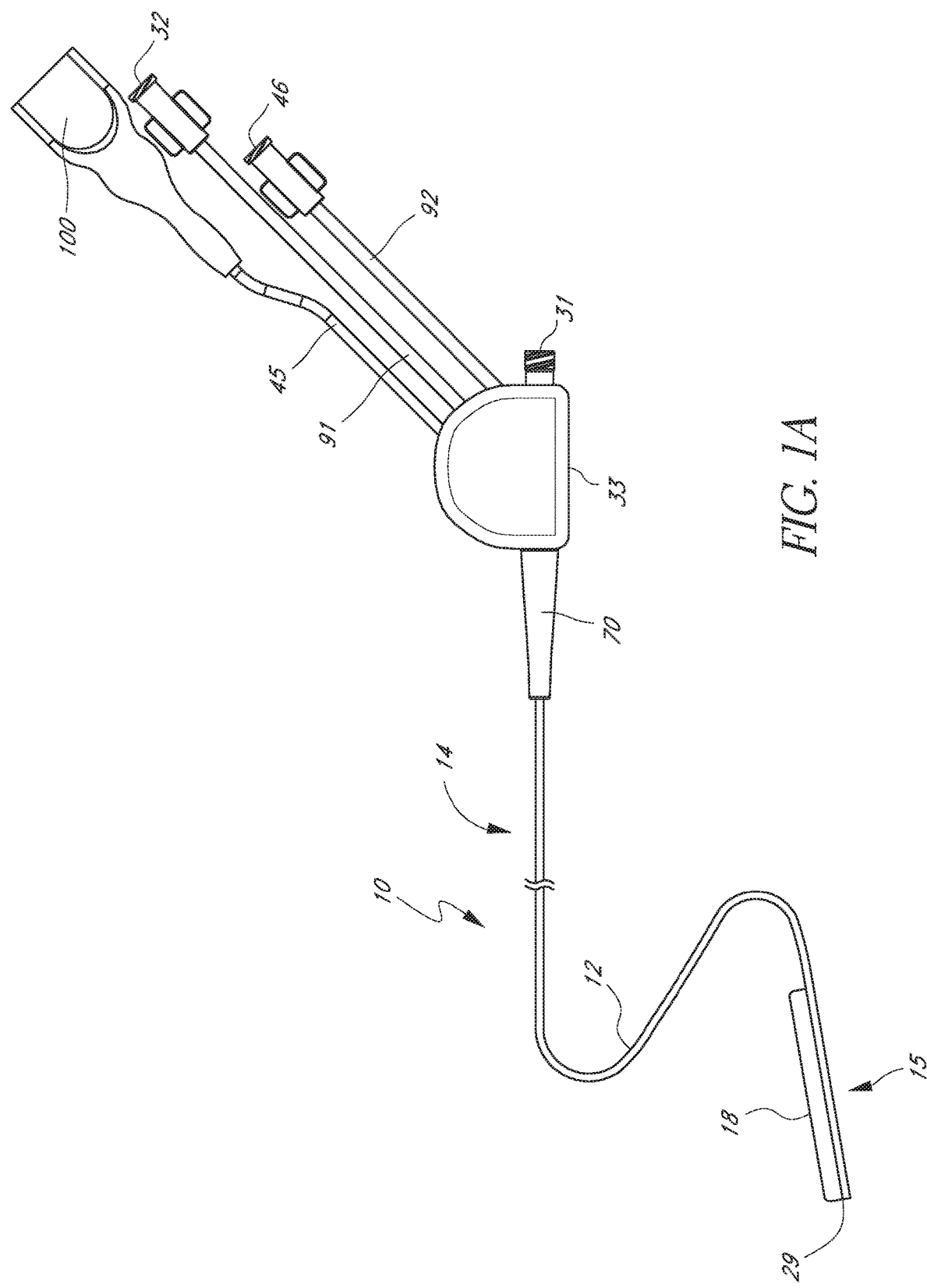
FIG. 1A is a schematic illustration of an ultrasonic catheter configured for insertion into large vessels of the human body.

As described above, it is desired to provide an ultrasonic catheter also referred to herein as "ultrasound catheter(s)" having various features and advantages. Examples of such features and advantages include the ability to apply ultrasonic energy to a treatment site. In other embodiments, the catheter has the ability to deliver a therapeutic compound to the treatment site. Embodiments of an ultrasonic catheter having certain of these features and advantages are described herein. Methods of using such an ultrasonic catheter are also described herein.

The ultrasonic catheters also referred to herein as "ultrasound catheter(s)" described herein can be used to enhance the therapeutic effects of therapeutic compounds at a treatment site within a patient's body. As used herein, the term "therapeutic compound" refers broadly, without limitation, to a drug, medicament, dissolution compound, genetic material, anti-cancer drug, or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069 and 6,210,356, the entire disclosures of which are hereby incorporated by herein by reference. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing Heparin, Uronkinase, Streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663, the entire disclosures of which are hereby incorporated by herein by reference.

The ultrasonic catheters described herein can be configured for applying ultrasonic energy over a substantial length of a body lumen, such as, for example, the larger vessels located in the leg. In other embodiments, the catheter can be configured for treatment of pulmonary embolisms, ("PE"), which can be caused when a large blood clot obstructs the major blood vessels leading from the heart to the lungs. However, it should be appreciated that certain features and aspects of the present disclosure may be applied to catheters configured to be inserted into other vessels or cavities such as the small cerebral vessels, in solid tissues, in duct systems and in body cavities. Additional embodiments that may be combined with certain features and aspects of the embodiments described herein are described in U.S. Patent Publication US2004/0019318, entitled "Ultrasound Assembly For Use With A Catheter" and filed Nov. 7, 2002, the entire disclosure of which is hereby incorporated herein by reference.

FIG. 1A schematically illustrates an ultrasonic catheter 10 configured for use in the large vessels of a patient's anatomy. For example, the ultrasonic catheter 10 illustrated in FIG. 1A can be used to treat long segment peripheral arterial occlusions, such as those in the vascular system of the leg. In other examples, the ultrasonic catheter 10 illustrated in FIG. 1A can be used for treatment of a pulmonary embolism as described, for example, in U.S. Patent Publication US2012/0289889 (filed May 10, 2012), which is hereby incorporated by reference herein in its entirety. As will be explained in detail below, in some embodiments, the catheter is configured to be introduced into the patient's the major blood vessels leading from the heart to the lungs (e.g., the pulmonary artery). In one embodiment of use, femoral venous access may be used to place the catheter 10 into such vessels. In such embodiments, the catheter 10 can be advanced through femoral access site, through the heart and into the pulmonary artery. The dimensions of the catheter 10 are adjusted based on the particular application for which the catheter 10 is to be used.

As illustrated in FIG. 1A, the ultrasonic catheter 10 can include a multi-component, elongate flexible exterior tubular body 12 having a proximal region 14 and a distal region 15. The exterior tubular body 12 can include a flexible energy delivery section 18 located in the distal region 15 of the catheter 10. The exterior tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in some embodiments, the proximal region 14 of the exterior tubular body 12 can comprise a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the exterior tubular body 12 is reinforced by braiding, mesh or other constructions to provide increased kink resistance and pushability. For example, nickel titanium or stainless steel wires can be placed along or incorporated into the exterior tubular body 12 to reduce kinking.

In some embodiments configured for treating thrombus in the arteries of the leg, the exterior tubular body 12 has an outside diameter between about 0.060 inches and about 0.075 inches (between about 0.15 cm and about 0.19 cm). In another embodiment, the exterior tubular body 12 has an outside diameter of about 0.071 inches (about 0.18 cm). In certain embodiments, the exterior tubular body 12 has an axial length of approximately 106 to 135 centimeters, although other lengths may by appropriate for other applications.

The energy delivery section 18 of the exterior tubular body 12 can include a material that is thinner than the material comprising the proximal region 14 of the exterior tubular body 12 or a material that has a greater acoustic transparency. Thinner materials generally have greater acoustic transparency than thicker materials. Suitable materials for the energy delivery section 18 can include, but are not limited to, high or low density polyethylenes, urethanes, nylons, and the like. In certain modified embodiments, the energy delivery section 18 may be formed from the same material or a material of the same thickness as the proximal region 14.

In certain embodiments, the exterior tubular body 12 can be divided into three sections of varying stiffness. In some embodiments, the first section, can include the proximal region 14, which can have a relatively higher stiffness. The second section, which can be located in an intermediate region between the proximal region 14 and the distal region 15 of the exterior tubular body 12, can have a relatively lower stiffness. This configuration further facilitates movement and placement of the catheter 10. The third section, which can include the energy delivery section 18, can be generally lower in stiffness than the second section in spite of the presence of the ultrasound radiating members 40.

To provide access to the interior of the exterior tubular body 12, a plurality of inlets can be fluidly connected to the proximal region 14 of catheter 10. In some examples, the proximal region 14 of the catheter 10 can include a cooling inlet port 46, a drug inlet port 32, and/or a proximal access port 31. In some embodiments, to provide an electrical connection to the energy delivery section 18, the catheter 10 can further include a cable 45 that can include a connector 101 to the control system 100 (shown in FIG. 10). In some variants, the cable 45 can be connected to the catheter 10 at the proximal region 14 through the proximal access port 31. In some examples, the catheter 10 can further include a backend hub 33 that helps to secure the various inlet ports at the proximal region 14 of the catheter 10.

Figure 1B:
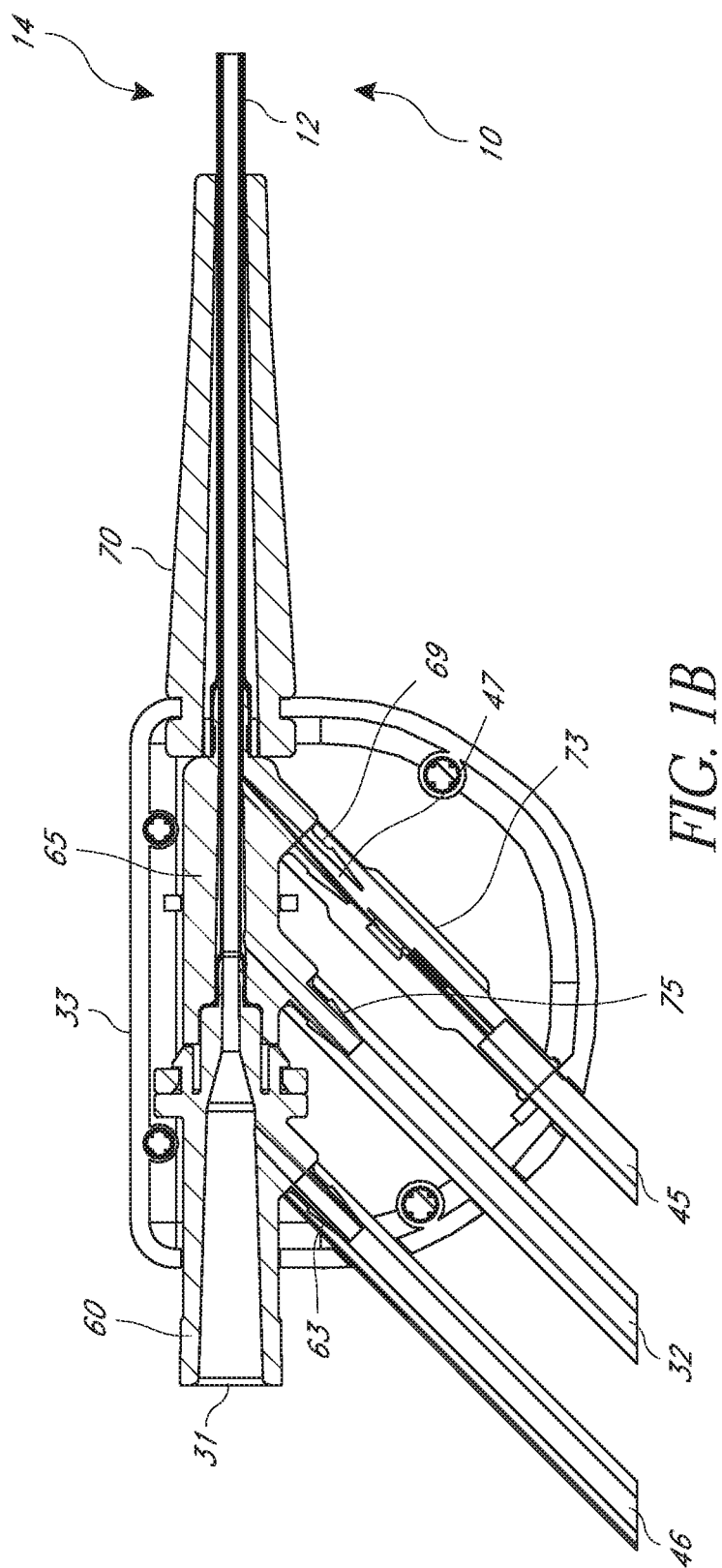
FIG. 1B is a cross-sectional view of the ultrasonic catheter of FIG. 1A.
Figure 1C:
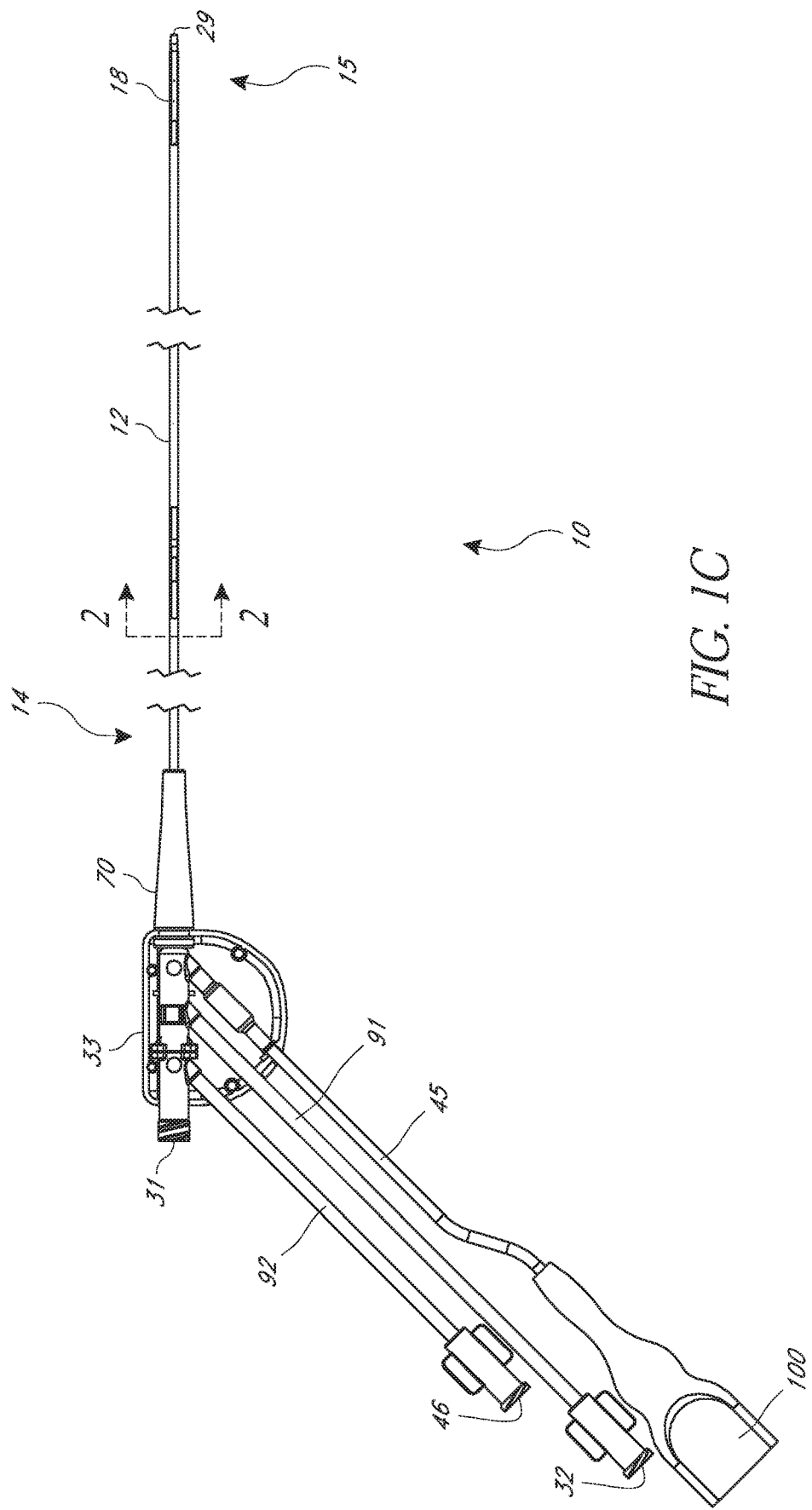
FIG. 1C is an enlarged cross-sectional view of a hub portion of the ultrasonic catheter of FIG. 1A.
Figure 1D:
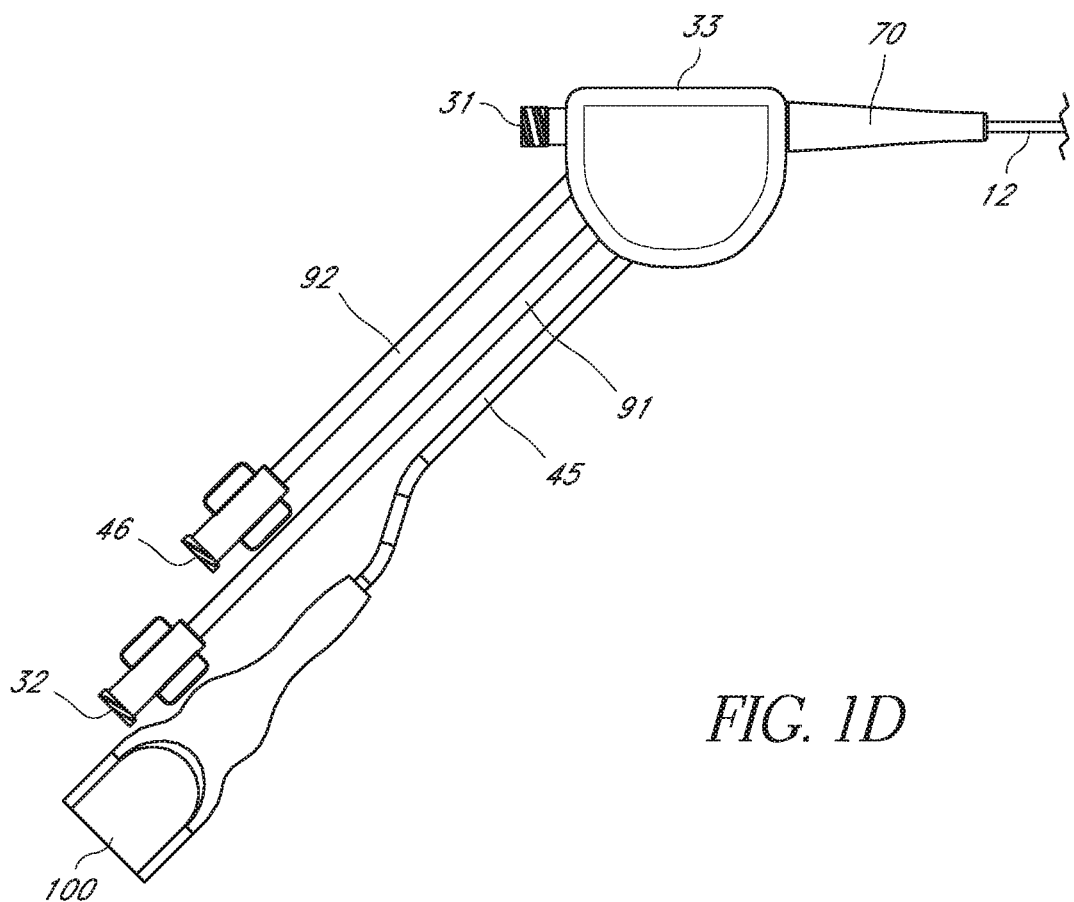
FIG. 1D is a side view of the hub portion ultrasonic catheter of FIG. 1A.
Figure 1E:
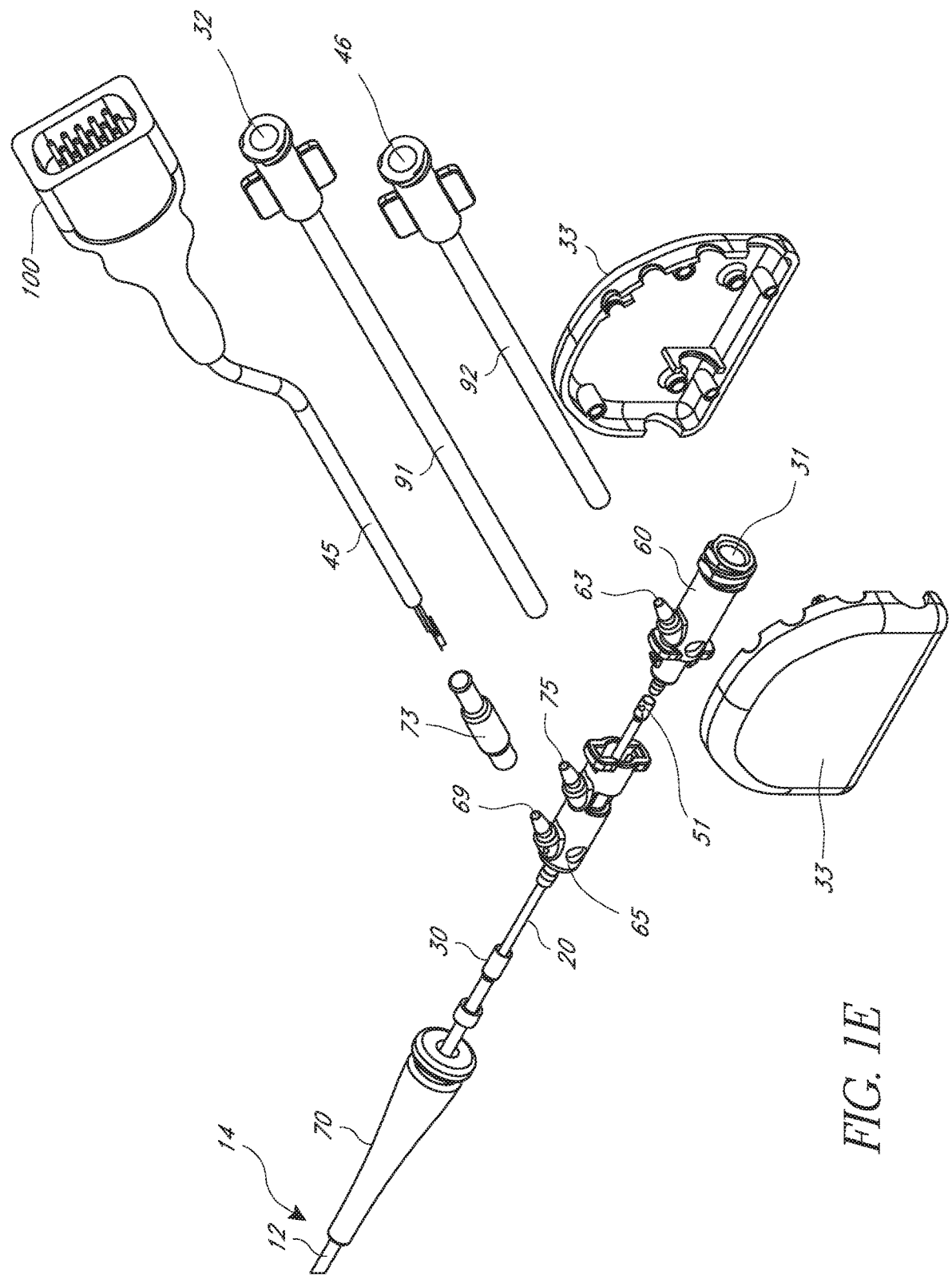
FIG. 1E is an exploded illustration the hub portion of the ultrasonic catheter of FIG. 1A.

FIGS. 1B-E illustrate various views of the ultrasound catheter of FIG. 1A. FIGS. 1B-1C illustrate cross-sectional views of the hub 33 and FIG. 1D-D illustrates a side view of the hub 33. FIG. 1E illustrates an exploded view of the hub 33.

Figure 2:
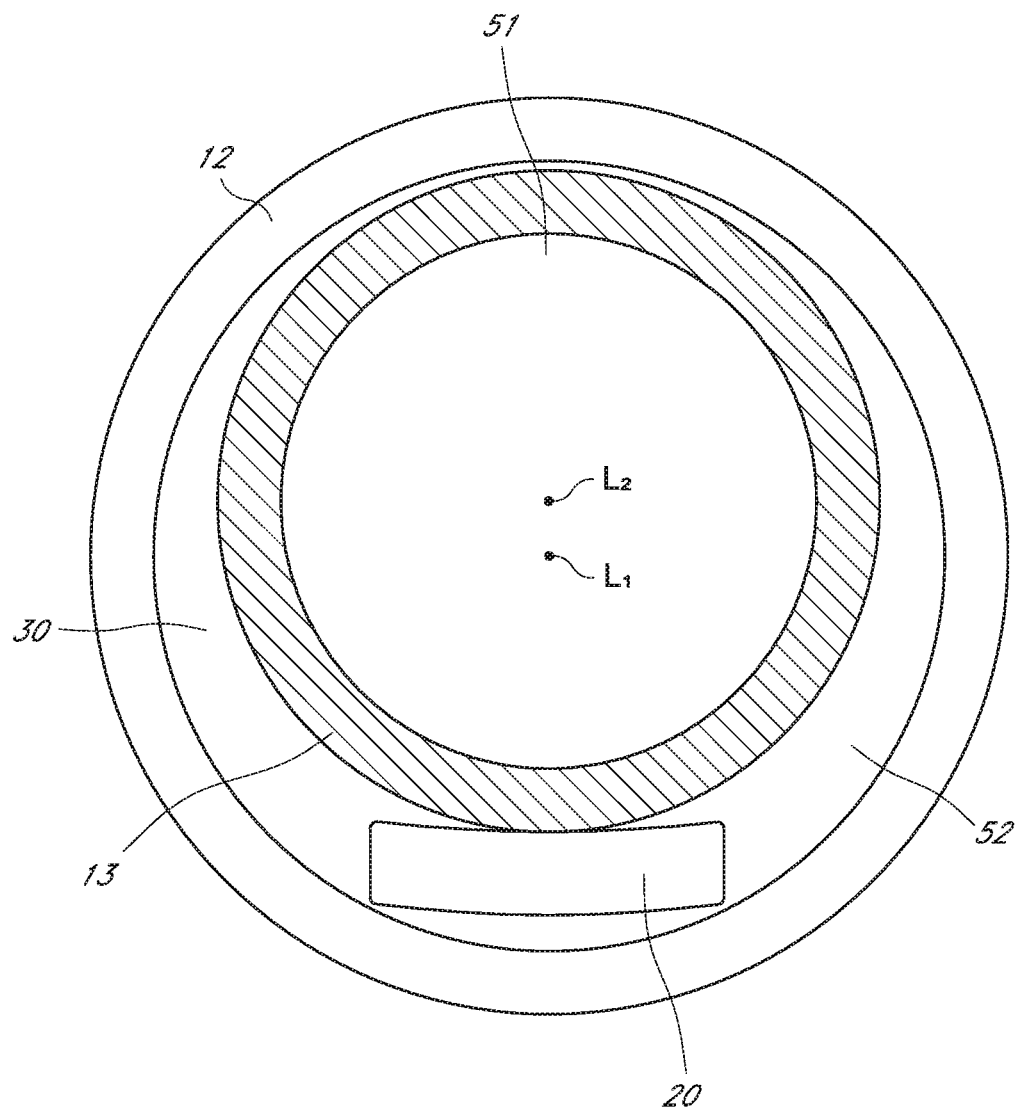
FIG. 2 is a cross-sectional view of the ultrasonic catheter taken along line 2-2 of FIG. 1C or anywhere along the length of the exterior tubular body of FIG. 1K.

FIG. 2 illustrates a cross section of the exterior tubular body 12 taken along line 2-2 in FIG. 1B. As shown in FIG. 2, in the illustrated embodiment the catheter 10 may be formed of two lumens—fluid delivery lumen 30 and central lumen 51, which can be formed from an interior wall of an exterior tubular body 12 and an interior wall of an interior tubular body 13, respectively. In some examples, the interior tubular body 13 can be located within the exterior tubular body 12 such that a gap 52 is formed between an interior wall of the exterior tubular body 12 and an exterior wall of the interior tubular body 13 such that the fluid delivery lumen 30 extends coaxially about the interior tubular body. In the embodiment shown in FIG. 2, the exterior tubular body 12 has a first longitudinal axis L1 extending centrally through the exterior tubular body 12, and the interior tubular body 13 has a second longitudinal axis L2 extending centrally through the interior tubular body 13. The first and second longitudinal axes L1, L2 are displaced from each other such that an asymmetrical gap 52 is formed between an outer surface of the interior tubular body 13 and an interior surface of the exterior tubular body 12. In other embodiments, more or fewer fluid delivery lumens can be formed by a plurality of tubular bodies located within the exterior tubular body 12 and/or by the addition of dividers and/or channels.

Figure 2A:
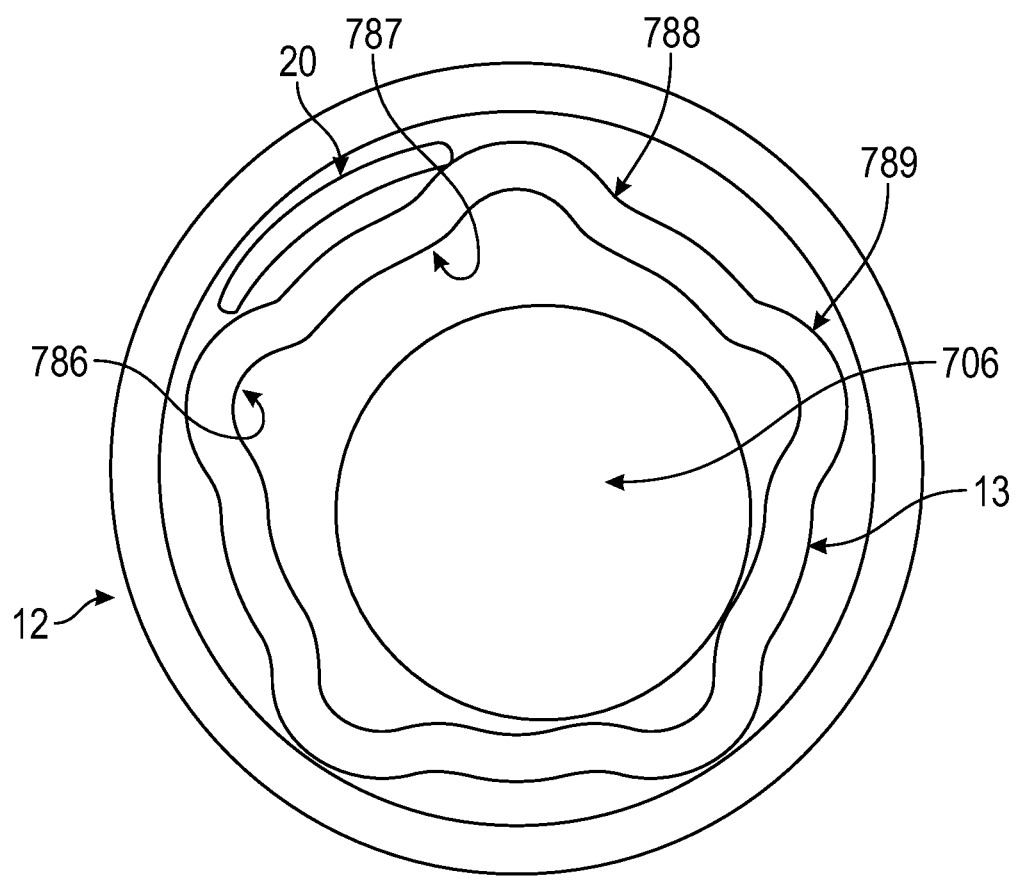
FIG. 2A is a cross-sectional view of another embodiment of the ultrasonic catheter taken along line 2-2 of FIG. 1C or anywhere along the length of the exterior tubular body of FIG. 1K.
Figure 2B:
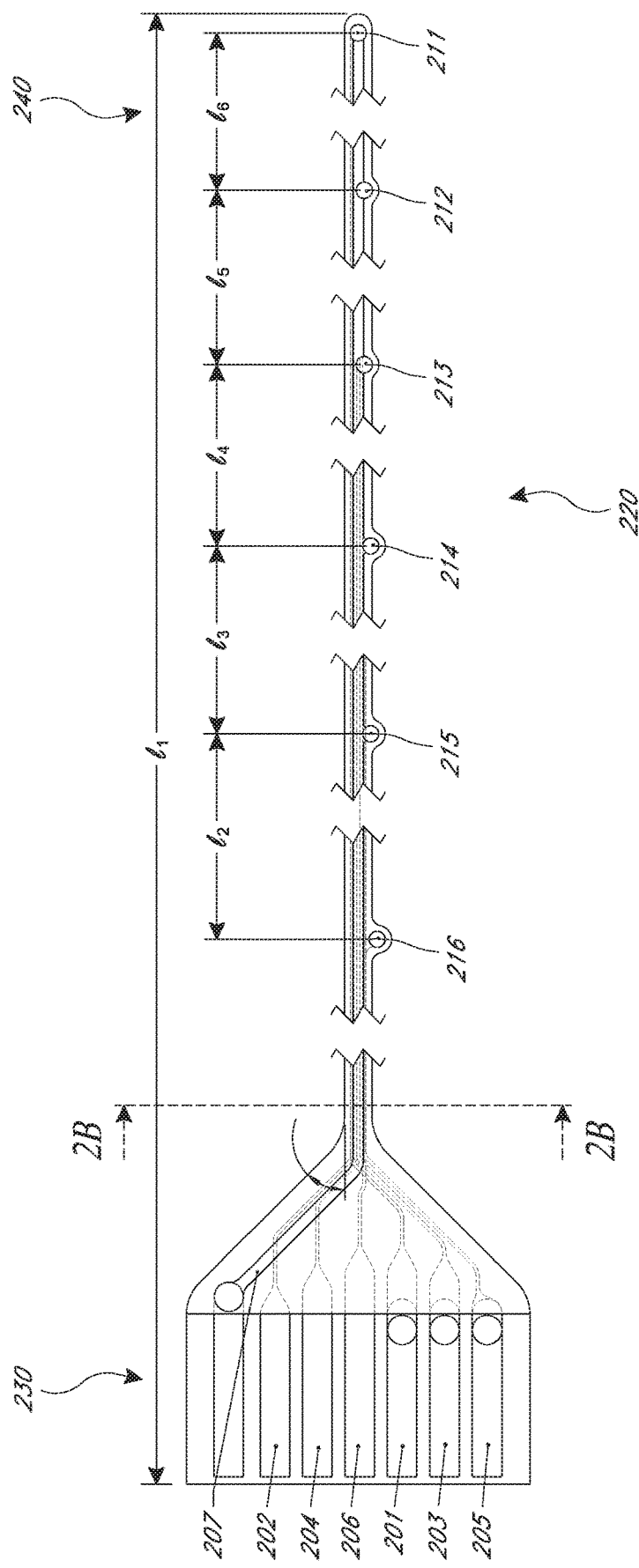
FIG. 2B is a top cross-sectional view of an embodiment of a flexible circuit ("flexcircuit") that can be configured to form a thermocouple to serve as a temperature sensor in the ultrasonic catheter illustrated in FIGS. 1A-1O and FIGS. 2-2A.
Figure 8:
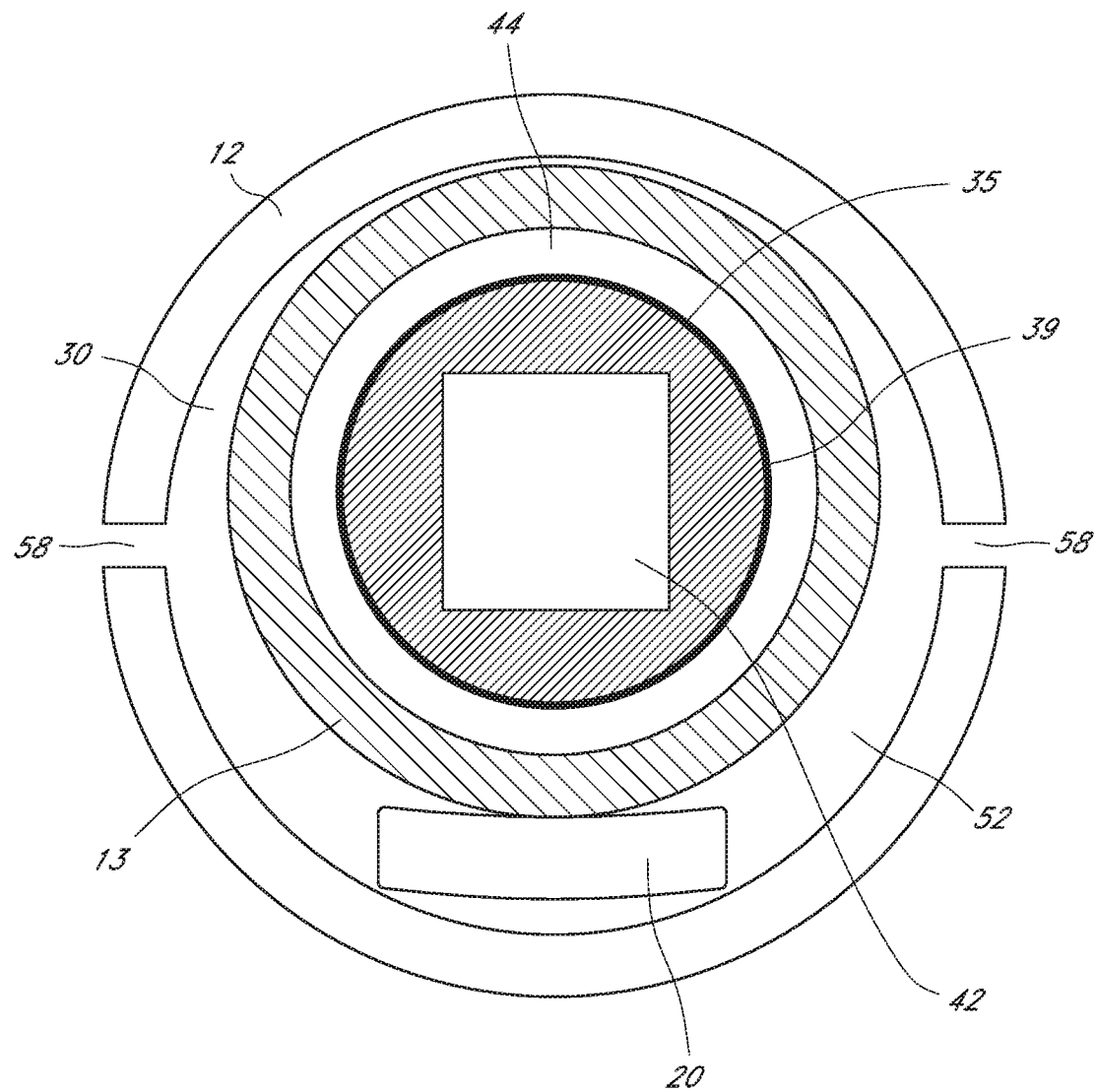
FIG. 8 illustrates the energy delivery section of the inner core of FIG. 4 positioned within the energy delivery section of the tubular body of FIG. 2.

With continued reference to FIG. 2, in some examples, the exterior tubular body 12 can further include a temperature sensor 20 that can be positioned within the fluid delivery lumen 30 between the outside surface of the of the interior tubular body 13 and the interior surface of the exterior tubular body 12. As will be described in more detail below, the temperature sensor 20 shown in FIGS. 2 and 8 can be a flexible circuit or "flexcircuit" 220 as shown in FIGS. 2A and 2B or flexcircuit 320 as shown in FIGS. 12A and 12B. In some embodiments the flexible circuit is configured to form a hermocouple. In certain embodiments, the temperature sensor 20 shown in FIGS. 2 and 8 can be a ribbon thermocouple 500 as shown in FIGS. 2D-2F or a ribbon thermocouple 600 as shown in FIGS. 2G-2I. As described below, there are potential advantages to embodiments that utilize a flexible circuit 220, 320 and/or thermocouple ribbon 500, 600 as described herein. However, in certain embodiments of the ultrasonic catheter 10, the temperature sensor 20 can take other configurations or forms. In some embodiments, the temperature sensor 20 is positioned on a side of the interior tubular body 13 such that the interior tubular body 13 is positioned asymmetrically within the exterior tubular body 12. In such an arrangement, an asymmetrical longitudinally extending gap 52 is formed between an outer surface of the interior tubular body (corresponding to the second tubular body) and an interior surface of the exterior tubular body (corresponding to the first tubular body); thus in the illustrated arrangement the gap 52 between the outer surface of the interior tubular body and the interior surface of the exterior tubular body can be an asymmetrical gap 52 (a crescent shape), which can have certain advantages as described below. It is therefore preferred that the flexible circuit or ribbon thermocouple is positioned in the widest portion of the asymmetrical gap 52, and optionally, adjacent the exterior surface of the interior tubular body. In an embodiment, the flexible circuit or ribbon thermocouple can be coupled to the outside surface of the interior tubular body 13 at one or more locations. In an embodiment, the flexible circuit or ribbon thermocouple can be coupled to the outside surface of the interior tubular body 13 at a distal end of the catheter 10. While not illustrated in FIGS. 2 and 8, in some embodiments, the flexible circuit or ribbon thermocouple can contact an interior surface of the exterior tubular body 12 (corresponding to the first tubular body) in addition to or, as an alternative, in some embodiments, to contacting the outer surface of the interior tubular body 13 (corresponding to the second tubular body). In certain embodiments, the flexible circuit 220 as shown in FIGS. 2A and 2B or flexcircuit 320 as shown in FIGS. 12A and 12B or be ribbon thermocouple 500 as shown in FIGS. 2D-2F or a ribbon thermocouple 600 as shown in FIGS. 2G-2I when positioned as shown in FIGS. 2 and 8, can bend and be curved as shown in FIGS. 2 and 8 to form a crescent shape corresponding to the outer surface of the interior tubular body 13 (corresponding to the second tubular body) and/or the interior surface of the exterior tubular body 12 (corresponding to the first tubular body).

FIG. 2A illustrates another embodiment of the cross section of an exterior tubular body 12. As shown in FIG. 2A, the exterior tubular body 12 can be disposed about the interior tubular body 13. An inner core 706 can be inserted within the interior tubular body 13 and positioned at a treatment site. As noted with regard to FIG. 2, the exterior tubular body 12 can also include a temperature sensor 20 which can be arranged in accordance with any of the embodiments described herein.

In some embodiments, the interior tubular body 13 can include an uneven exterior and/or interior surface that can, as will be discussed in more detail, additional cooling within the device. In some embodiments, the interior tubular body 13 can have a non-circular cross-section. In some embodiments, the interior tubular body 13 can include a plurality of indentations 786 and/or protrusions 787 such that the interior tubular body 13 does not have a circular interior surface and/or exterior surface. Because the diameter of the inner core 706 is less than the diameter of the interior tubular body, in an interior tubular body with a circular interior surface, the inner core 706 could be placed against the interior tubular body 13 such that there could be a relatively large portion with no or minimal gap between the exterior surface of the inner core 706 and the interior surface of the interior tubular body 13 and/or a relatively large portion with no or minimal gap between the exterior of the interior tubular body 13 and the interior of the exterior tubular body 12. This can potentially cause uneven over-heating of the inner core 706. The indentations 786 can therefore ensure that cooling fluid will have room to flow past the inner core 706 and contact more external surfaces of the inner core 706. In a similar manner, drug flowing between the interior tubular body 13 and the exterior tubular body 12 can be more uniformly distributed between the two tubular components as a result of an uneven surface about the exterior of the interior tubular body 13. In some embodiments, the exterior of the interior tubular body 13 can include indentations 788 and/or protrusions 789. In some embodiments, the plurality of indentations 788 and/or protrusions 789 can ensure that the inner core 706 does not cause overheating within the exterior tubular body 12. In some examples, as the indentations 786, 788 and/or protrusions 787, 789 can be of any shape or size, this can reduce manufacturing costs as any imperfection on the inner and/or outer surface of the tubular body 13 would provide additional cooling benefits to the inserted inner core 706. The indentations 786, 788 and/or protrusions 787, 789 can extend longitudinally along the length of the interior tubular body 13. In certain embodiments, the indentations 786, 788 and/or protrusions 787, 789 can extend longitudinally along at least 50% of the length of the interior tubular body 13 and along at least 75% of the length of the interior tubular body 13 and in certain embodiments along at least 90% of the length of the interior tubular body 13. The embodiment of the interior tubular body 13 with indentations 786, 788 and/or protrusions 787, 789 can be used in combination with the temperature sensors described herein and/or used independently to promote uniform cooling.

Temperature Sensor

Turning first to the flexcircuits illustrated in FIGS. 2B-C and 12A-12B, as described above, the temperature sensor 20 can comprise a flexible circuit ("flexcircuit") that is configured to form one or more thermocouples. The flexcircuit can be used to measure the temperature at different points along the length of the catheter 10, and so it is preferred that the flexible circuit extends along the length of the central first tubular body.

Figure 2C:
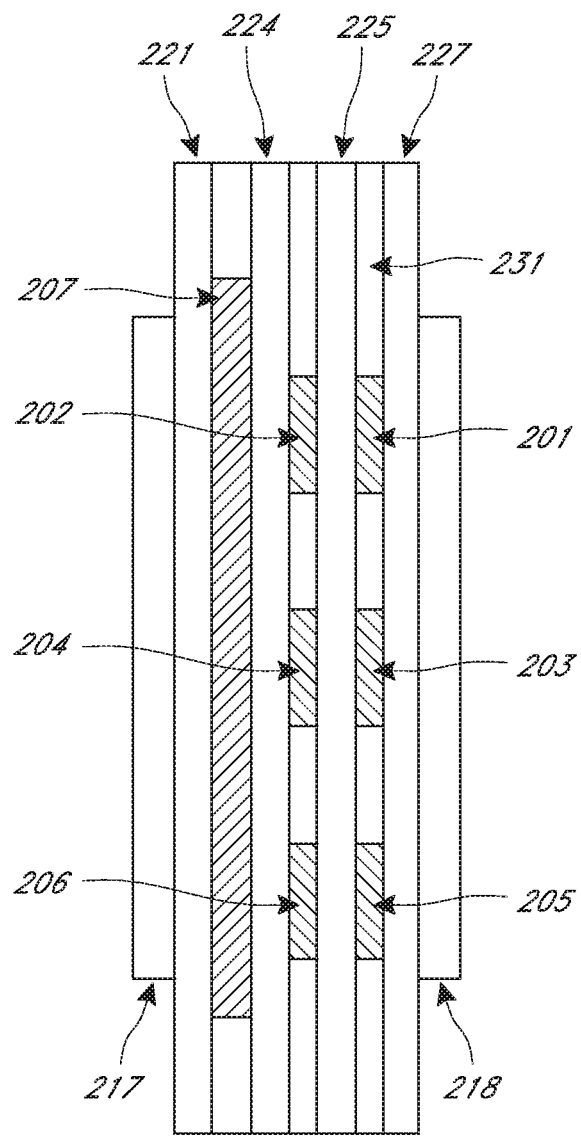
FIG. 2C is a side cross-sectional view of the embodiment of the flexcircuit illustrated in FIG. 2B.
Figure 2D:
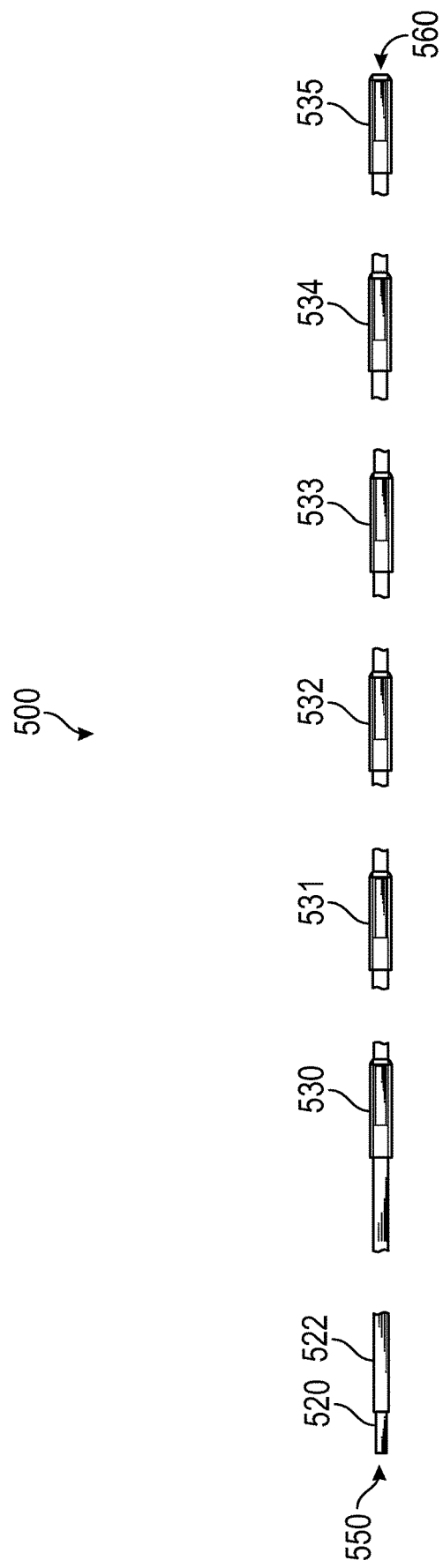
FIG. 2D is a side view of an embodiment of a temperature sensor composed of a plurality of insulated wires configured to form a plurality of thermocouples.
Figure 2E:
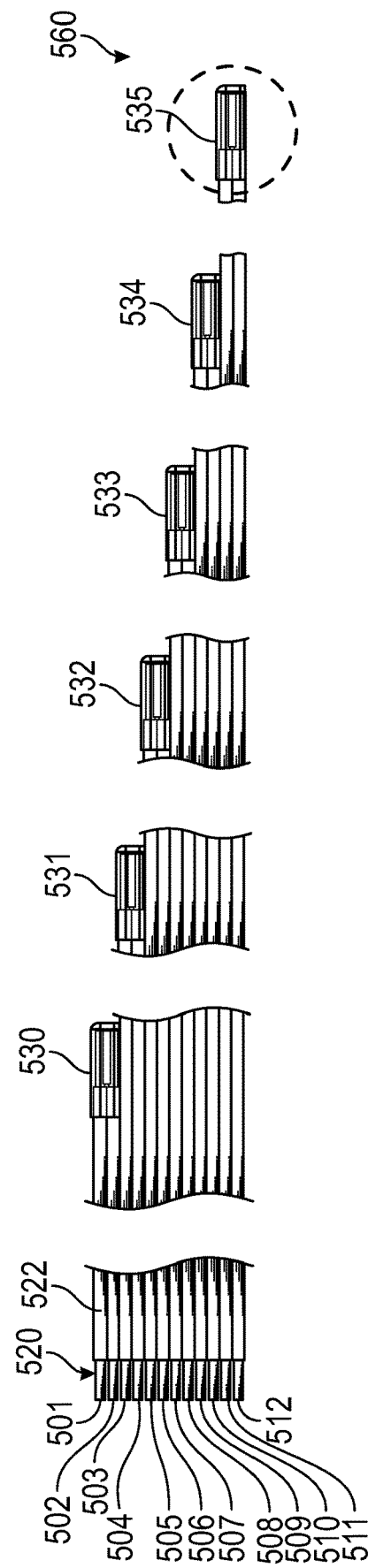
FIG. 2E is a top view of an embodiment of the temperature sensor of FIG. 2D.
Figure 2F:
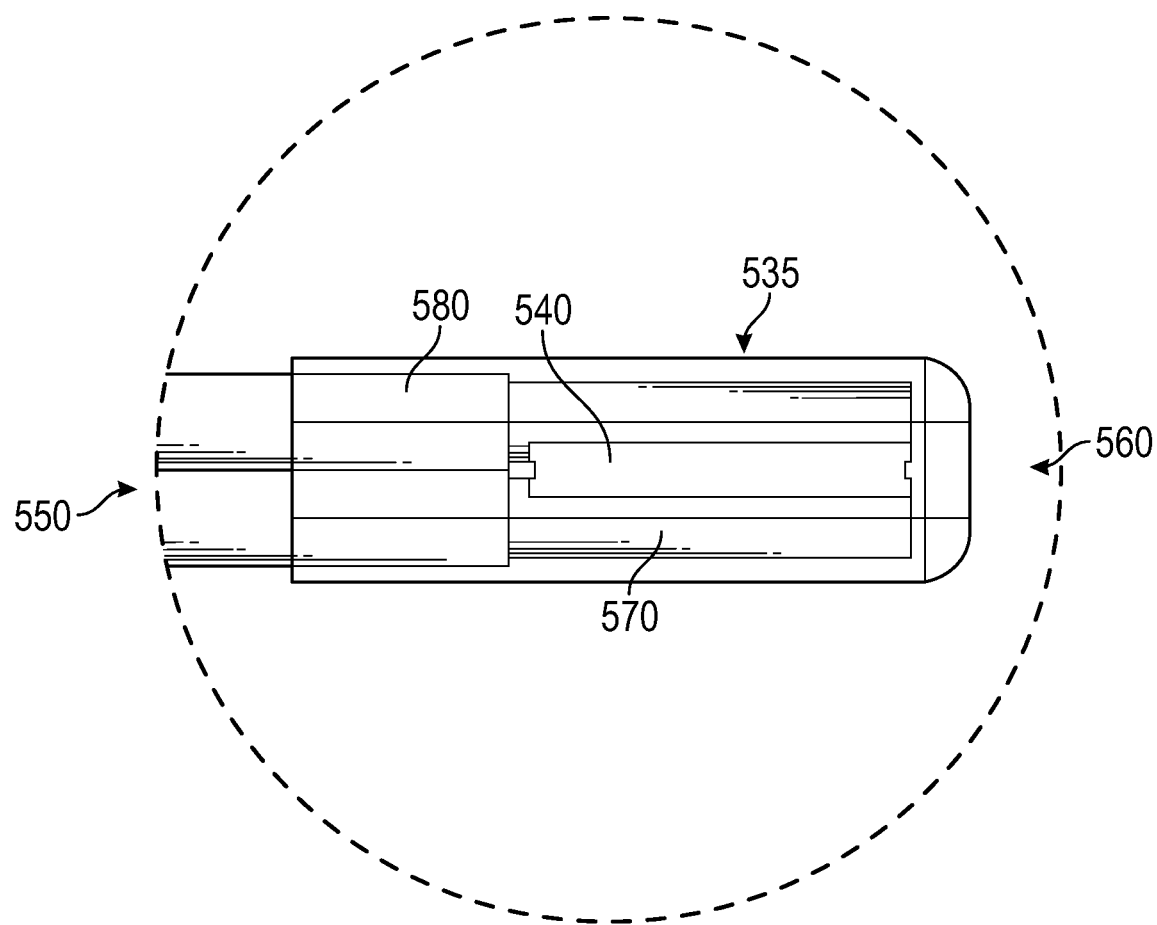
FIG. 2F is an enlarged top view of a thermocouple junction of the temperature sensor of FIG. 2D.
Figure 2G:
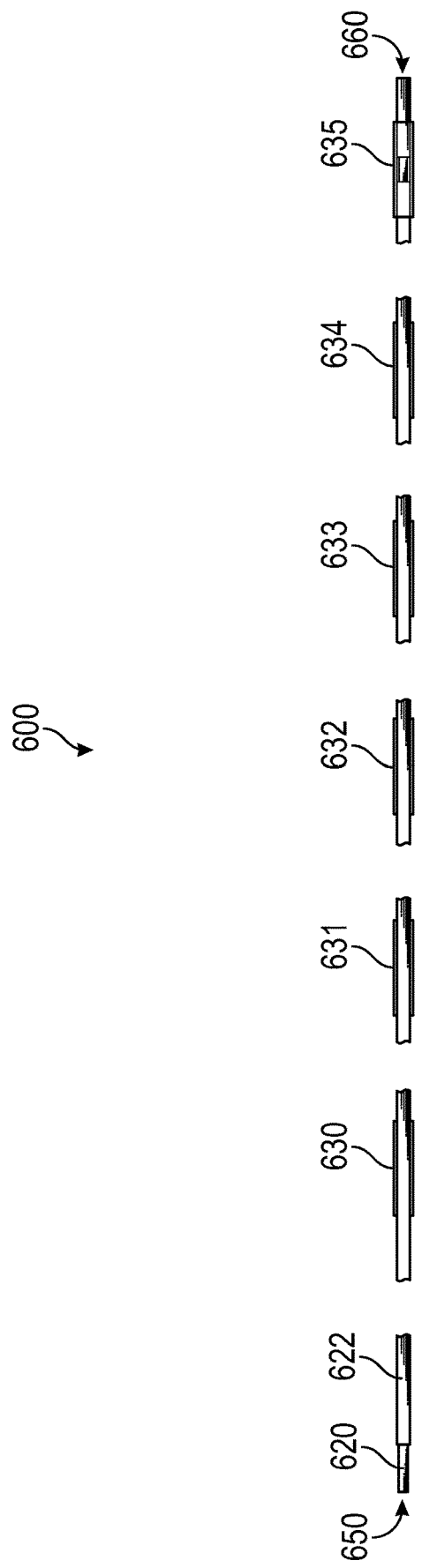
FIG. 2G is a side view of another embodiment of a temperature sensor composed of a plurality of insulated wires configured to form a plurality of thermocouples.
Figure 2H:
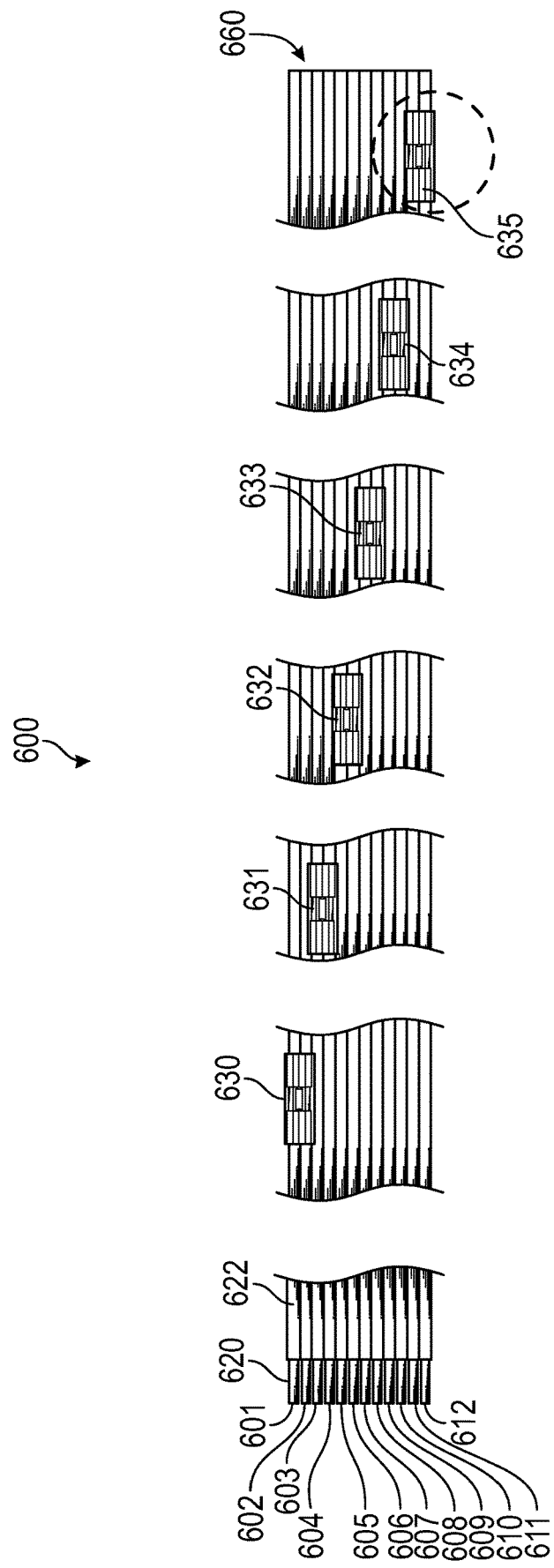
FIG. 2H is a top view of another embodiment of a temperature sensor of FIG. 2G.
Figure 2I:
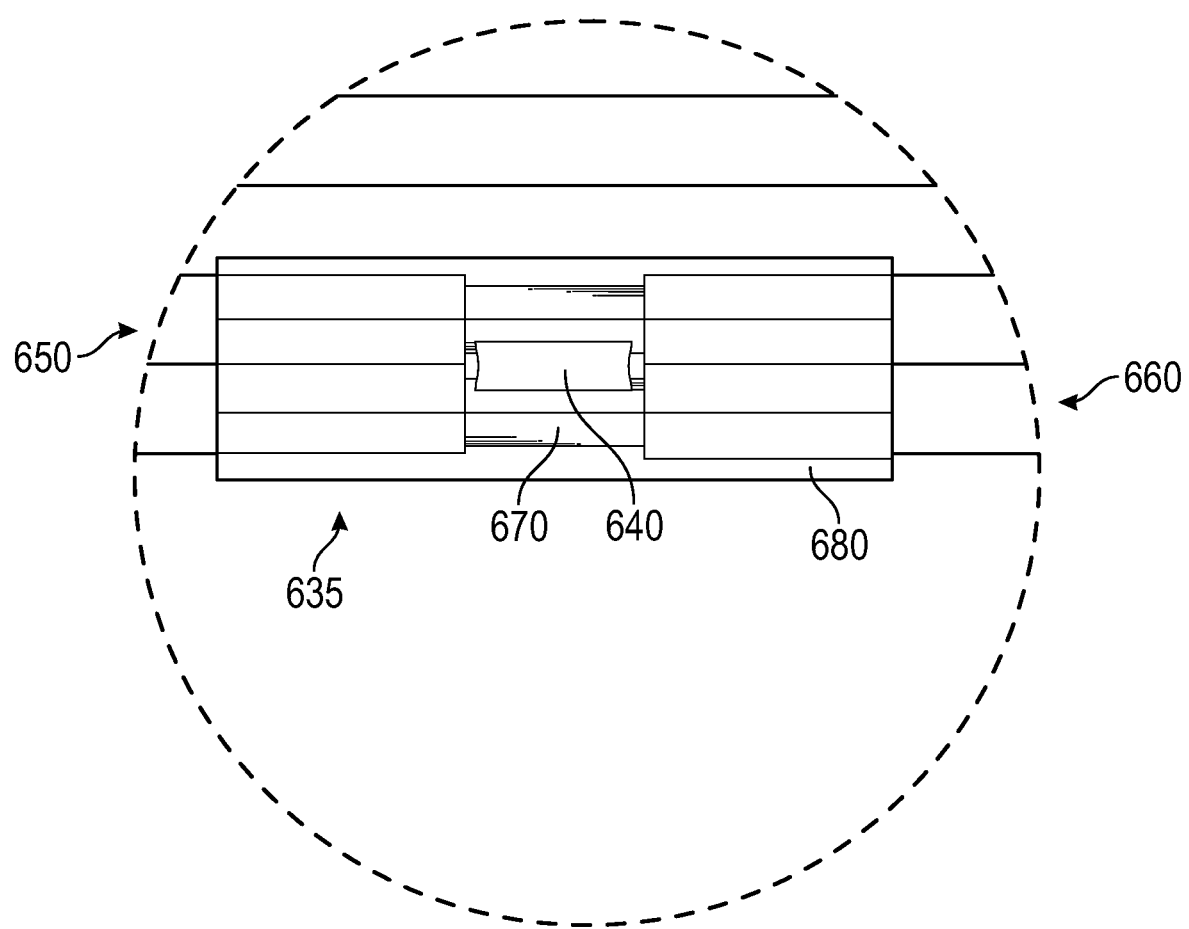
FIG. 2I is an enlarged top view of a thermocouple junction of the temperature sensor of FIG. 2G.

FIG. 2B illustrates a top view of one embodiment of the flexcircuit 220 and FIG. 2C is a cross-sectional view of the flexcircuit 220. FIGS. 12A-12B illustrate two views of another embodiment of a flexcircuit 320. With reference to FIGS. 2B and 2C, on one embodiment, the flexcircuit 220 is composed of a plurality of traces. In one embodiment, the flexcircuit 220 includes a first trace 207 that runs the entire length of the flexcircuit 220. The first trace is preferably constantan. Constantan is a copper-nickel alloy that has a constant resistivity over a wide range of temperatures. The first trace 207 can therefore provide good temperature sensitivity along its length. While a constantan trace is preferred, modified embodiments can include a trace of a different material.

To form the thermocouple, the flexcircuit 220 includes a plurality of second traces formed of a material different than the first trace 207. Each individual trace of this plurality of second traces extends from the proximal end 230 to a different point along the length of the flexcircuit 220. In some examples, the individual traces of this plurality of second traces are made of copper overlaid on the flexcircuit 220. In the illustrated embodiment, the first trace is Constantan and the plurality of second traces are formed from copper. In other embodiments, the first and second materials can be a different combination of materials. For example, the first material can be Alumel (consisting of approximately 95% nickel, 2% manganese, 2% aluminum and 1% silicon) and the second material can be Chromel (90% nickel and 10% chromium) as can be found in a Type K thermocouple or other combinations of dissimilar materials. In one example, the flexcircuit 220 can include a trace 201 that extends from the proximal end 230 of the flexcircuit 220 to a joint 211 at the distal end 240 of the flexcircuit 220. Similarly, the flexcircuit 220 can include one or more of any of the following traces: trace 201 that extends from the proximal end 230 to a joint 211 close to a distal end of the flexcircuit 220, trace 202 that extends from the proximal end 230 to a joint 212, trace 203 that extends from the proximal end 230 to a joint 213, trace 204 that extends from the proximal end 230 to a joint 214, trace 205 that extends from the proximal end 230 to a joint 215, and trace 206 that extends from the proximal end 230 to a joint 216 closer to a proximal end of the flexcircuit 220. In some examples, the plurality of joints (e.g. joint 211, joint 212, joint 213, joint 214, joint 215, and joint 216) allows the temperature to be taken along several points along the length of the flexcircuit 220. In some variants, this can help to measure the temperature of the ultrasonic catheter along the entire length of the device or a portion of the device (e.g., a portion of the device that includes the ultrasound elements described below). In modified embodiments, the traces 201-206 and joints 211-216 can be arranged in different orders or configurations.

When temperature differential is experienced by the different conductors (e.g., between one of the traces 201-206 and the first trace 207), it produces a voltage when the temperature of one of the spots differs from the reference temperature at other parts of the circuit. In this manner, temperatures along the flexcircuit 220 can be measured by measuring the voltages between one of the traces 201-206 and the first trace 207. The illustrated preferred embodiment of FIG. 2B includes a single first trace of Constantan and six (6) traces of copper, although in other embodiments other dissimilar material combinations such as Alumel and Chromel may be used together, respectively. In modified embodiments more or fewer traces and/or traces formed of different materials each dissimilar from the first trace may be used. An advantage of the illustrated embodiment is that a single first trace can be used to measure the temperature at multiple locations along the length of the flexcircuit 220, which can reduce the overall size of the flexcircuit as compared to a circuit with multiple first traces; in the preferred embodiment, a single Constantan trace is used as the first trace, which can reduce the overall size of the flexcircuit as compared to a circuit with multiple Constantan first traces. In modified embodiments, the flexcircuit can include multiple first traces that are each individually associated with the individual traces of the plurality of second traces of dissimilar materials.

In some embodiments, the flexcircuit 220 can be of variable length and can be configured to run the entire length or a portion of the catheter 10. Similarly, to measure temperature along the length of the flexcircuit 220, the distance between the joints 211-216 can be varied for the catheter 10. In the one embodiment, the flexcircuit 220 can have a length $l_1$ from proximal end 230 to distal end 240 of about 115 cm. In some embodiments, the distance between each of the joints 211-216 (e.g. length $l_2$, length $l_3$, length $l_4$, length $l_5$, length $l_6$) can be approximately 10 cm. In additional embodiments, the distance between each of the joints 211-216 can be between 1.0 cm and 50.0 cm depending upon the number of joints and the desired overall length of the flexcircuit 220. The distance between the joints 211-216 need not be uniform in certain embodiments. As mentioned above, in one arrangement, the joints are positioned generally along the length of the catheter in which the ultrasound elements are positioned such that the temperature of the catheter around the ultrasound elements can be monitored. Accordingly, in the illustrated embodiment the joints 211, 212, 213, 214, 215, 216 are positioned in the energy delivery section 18 of the exterior tubular body 12.

FIG. 2C illustrates a side cross-sectional view of the flexcircuit 220. As described previously, the flexcircuit 220 can be formed by a plurality of layered traces. In one example, the flexcircuit 220 includes the first trace 207 formed on a bottom middle layer 224. In some variants, the first trace 207 can be 0.001 inch (0.003 cm) thick. The flexcircuit 220 can include three traces 202, 204, 206 and 201, 203, 205 formed on a top middle layer 225, respectively, that can be formed from a different material than the first trace 207 and arranged as described above. Each of the second or copper traces can be separated from each other by adhesive 231 which can fill in the gaps between layers of the flexcircuit and traces In the illustrated embodiments the flexcircuit 220 can include a plurality of insulating layers between each of the layers containing the traces. As discussed above, aside from where a joint between two of the conductive layers are formed (e.g. joint 211, joint 212, joint 213, joint 214, joint 215, and joint 216), the plurality of insulating layers covers the length of the trace to insulate each of the traces from each other. The flexible circuit therefore comprises a plurality of joints 211, 212, 213, 214, 215 and 216 between the dissimilar materials of the first trace 207 and each of the plurality of second traces 201, 202, 203, 204, 205 and 206. As illustrated in FIG. 12B, the flexcircuit 220 can include a bottom coverlay 221, the bottom middle layer 224, top middle layer 225, and a top coverlay 227 that forms an insulating layer between each of the trace layers. The flexcircuit 220 of the illustrated embodiment also includes additional top insulating layer 218 and bottom insulating layer 217 which can cover electrically conducting vias which form the joints 211-216 that connect corresponding traces. In the preferred embodiment, each of these insulating layers can be formed of polyimide. In an embodiment, the top insulating layer 218 and bottom insulating layer 217 can extend along the entire length of the flexcircuit 220. In another embodiment, the top insulating layer 218 and bottom insulating layer 217 can cover portions of the flexcircuit 220 around the joints 211-216. In one embodiment, the joints 211-216 are formed by forming an electrically conducting via through the flexcircuit 220 to electrically connect the respective first trace 207 and second traces 201-206. The via can then be covered with the top insulating layer 218 and bottom insulating layer 217. As shown in FIG. 2C, gaps between the respective layers and traces can be filled in with an adhesive 231.

FIGS. 12A-12B illustrate another embodiment of a flexcircuit 320. FIG. 12A shows a vertical cross-sectional view of the flexcircuit 320 at a proximal point. As shown, the flexcircuit 320 can include a plurality of traces that are located on each of the top and bottom surfaces of the flexcircuit 320. As an example illustrated in FIG. 12B, the top surface can include a plurality of second traces 301, 302, and 303 whereas the bottom surface can include a plurality of second traces 304, 305, and 306, with a first trace 307 running laterally on a side, in this case the right side. The traces on the top and bottom surface of the flexcircuit 320 are separated by an insulator 308. In some examples, the bottom surface of the flexcircuit 320 can include a protective first coverlay 309 whereas the top surface of the flexcircuit 320 can include a protective second coverlay 310. The thickness of the flexcircuit 320 can be approximately 0.004 cm and the width of the flexcircuit 320 can be approximately 0.021 cm. In some embodiments, each of the traces of the flexcircuit 320 can be separated by a space of 0.003 cm.

The flexcircuit 320 can include a first material trace 307 that runs parallel to the length of the flexcircuit 320. In order to measure temperature at a specific point along the flexcircuit 320, each of the traces (e.g. trace 301, trace 302, trace 303, trace 304, trace 305, and trace 306) runs a varied distance along the flexcircuit 320. Traces (e.g. trace 301, trace 302, trace 303, trace 304, trace 305, and trace 306) can be made of a second material different from the first material. As with the embodiment of FIGS. 2A-2B, in one embodiment, the first material is Constantan and the second material is copper. In other embodiments, other dissimilar material combinations such as Alumel and Chromel can be used together. In some examples, where a temperature measurement is desired, one of the traces can make a right angle and form a node to contact the constantan trace 307.

FIG. 12A is a horizontal cross section illustrating a top view of a section of the flexcircuit 320 with protective second coverlay 310 removed. As illustrated, a temperature measurement can be obtained at node 312—a point along the flexcircuit 320. Each of the traces (e.g. trace 301, trace 302, trace 303, trace 304, trace 305, and trace 306) can run parallel along the length of the flexcircuit 320. At varying points, a node is formed where the trace turns to contact the first material trace 307. FIG. 12A shows a view taken at a more distal point than that shown in FIG. 12B, as at the segment of the flexcircuit 320 shown in FIG. 12A, the trace 303 has already formed a node to determine the temperature at a point further ahead proximally and therefore does not appear in this view. As well, trace 301 continues to run distally across the length of the segment shown in FIG. 12A and can therefore determine the temperature of the flexcircuit 320 distally further down along the length of the flexcircuit 320. The node 312 (and any of nodes 311, 313, 314, 315 and 316 (not shown)) can have a width of 0.011 cm and a height of 0.006 cm. Nodes 311, 312, 313, 314, 315 and 316 therefore constitute a plurality of joints between the dissimilar materials of the first material trace 307 and each of the plurality of second traces 301, 302, 303, 304, 305 and 306.

In certain embodiments, the temperature sensor 20 can be a ribbon thermocouple composed of a plurality of wires or that are coupled together. For example, FIGS. 2D-2F illustrate an embodiment of ribbon thermocouple 500. In some embodiments, the ribbon thermocouple 500 can be composed of a plurality of filaments and a plurality of thermocouple junctions. The plurality of filaments can be adhered together along the entire length of the ribbon thermocouple 500, from the proximal end 550 to the distal end 560. As will be discussed in more detail below, each of the plurality of filaments are adhered together except within 0.50 inches of the formed thermocouple junction.

As shown in FIG. 2E, in some embodiments, the ribbon thermocouple 500 can include filament 501, filament 502, filament 503, filament 504, filament 505, filament 506, filament 507, filament 508, filament 509, filament 510, filament 511, and filament 512. In some examples, each of the filaments is composed of a conductor 520 and an insulator 522. In some embodiments, the conductor 520 of each of the filaments is composed of a material such as copper or constantan. In some embodiments, the material of the conductor 520 of each of the filaments alternates. For example, filament 501, filament 503, filament 505, filament 507, filament 509, and filament 511 is composed of copper and filament 502, filament 504, filament 506, filament 508, filament 510, and filament 512 is composed of constantan. In some embodiments, the insulator 522 of each of the filaments is composed of polyesterimide.

In some examples, the ribbon thermocouple 500 can be configured to form a plurality of thermocouples along the length of the ribbon thermocouple 500 from the proximal end 550 to the distal end 560. In some embodiments, each of the thermocouples can be formed by stripping adjacent filaments of insulation and soldering the exposed conductor 520 together to form a thermocouple joint. As illustrated in FIGS. 2D-2E, thermocouple junction 530 can be formed by stripping filament 501 and filament 502 and soldering them together, thermocouple junction 531 can be formed by stripping filament 503 and filament 504 and soldering them together, thermocouple junction 532 can be formed by stripping filament 505 and filament 506 and soldering them together, thermocouple junction 533 can be formed by filament 507 and filament 508 and soldering them together, thermocouple junction 534 can be formed by filament 509 and filament 510 and soldering them together, and thermocouple junction 535 can be formed by filament 511 and filament 512 and soldering them together.

In some examples, the two filaments of the thermocouple junction are formed of different materials. In some embodiments, one of the two filaments of the thermocouple junction is formed of copper and one of the two filaments of the thermocouple junction is formed of constantan.

As shown in FIG. 2E, in some embodiments, the filaments are terminated at the formed thermocouple junction. FIG. 2F illustrates an enlarged view of the thermocouple junction 535 along section A-A of FIG. 2E. As discussed above, the distal end 560 of the pair of filaments has a stripped portion 570. In some embodiments, the stripped portion 570 of the pair of filaments is attached together with a solder 540. In some examples, the attachment of the two filaments is done by laser welding. In some examples, the insulation of the pair of filaments is laser stripped. In some embodiments, the solder is composed of about 95% to about 99% tin. In some examples, the thermocouple junction 535 includes a joint insulation 580. In some embodiments, the joint insulation 580 is composed of a polymer.

FIGS. 2G-2I illustrate another embodiment of a ribbon thermocouple 600 composed of a plurality of filaments and a plurality of thermocouple junctions. The plurality of filaments can be adhered together along the entire length of the ribbon thermocouple 600, from the proximal end 650 to the distal end 660. As will be discussed in more detail below, each of the plurality of filaments can be adhered together along the entire length of the ribbon thermocouple 600.

As shown in FIG. 2H, in some embodiments, the ribbon thermocouple 600 can include filament 601, filament 602, filament 603, filament 604, filament 605, filament 606, filament 607, filament 608, filament 609, filament 610, filament 611, and filament 612. In some examples, each of the filaments is composed of a conductor 620 and an insulator 622. In some embodiments, the conductor 620 of each of the filaments is composed of a material such as copper or constantan. In some embodiments, the conductor 620 of each of the filaments alternates. For example, filament 601, filament 603, filament 605, filament 607, filament 609, and filament 611 is composed of copper and filament 602, filament 604, filament 606, filament 608, filament 610, and filament 612 is composed of constantan.

In some examples, the ribbon thermocouple 600 can be configured to form a plurality of thermocouples along the length of the temperature sensor 600 from the proximal end 650 to the distal end 660. In some embodiments, each of the thermocouples can be formed by stripping adjacent filaments of insulation and soldering the exposed conductor 520 together to form a thermocouple joint. As illustrated in FIGS. 2G-2I, thermocouple junction 630 can be formed by stripping filament 601 and filament 602 and soldering them together, thermocouple junction 631 can be formed by stripping filament 603 and filament 604 and soldering them together, thermocouple junction 632 can be formed by stripping filament 605 and filament 606 and soldering them together, thermocouple junction 633 can be formed by filament 607 and filament 608 and soldering them together, thermocouple junction 634 can be formed by filament 609 and filament 610 and soldering them together, and thermocouple junction 635 can be formed by filament 611 and filament 612 and soldering them together.

In some examples, the two filaments of the thermocouple junction are formed of different materials. In some embodiments, one of the two filaments of the thermocouple junction is formed of copper and one of the two filaments of the thermocouple junction is formed of constantan.

As shown in FIG. 2H, each of the filaments extends from the proximal end 650 to the distal end 660, with the thermocouple junctions formed on a portion of the filaments. FIG. 2I illustrates an enlarged view of the thermocouple junction 635 along section A-A of FIG. 2H. As discussed above, a portion of the pair of filaments has a stripped portion 670 to form a window in the insulator 622 along the pair of filaments. In some examples, the insulation of the pair of filaments is laser stripped. In some embodiments, the stripped portion 670 of the pair of filaments is attached together with a solder 640. In some examples, the attachment of the two filaments is done by laser welding. In some embodiments, the solder is composed of about 95% to about 99% tin. In some embodiments, the thermocouple junction 635 includes a joint insulation 680. In some examples, the joint insulation 680 is composed of a polymer.

The illustrated embodiments of FIGS. 2-2I and 12A-12B have several advantages. For example, prior art ultrasound catheters have included a plurality of separate thermocouple wires extending along the length of the catheter in order to measure the temperature of the catheter at several locations along the energy delivery section of the catheter. By replacing the plurality of wires with a single flexible circuit or ribbon thermocouple with a plurality of nodes along the length of the flexcircuit or ribbon thermocouple, the complexity and costs associated with assembling the catheter can be reduced as only a single element (flex circuit or ribbon thermocouple) needs to be inserted between the catheter elements. In addition, as shown in FIGS. 2-2A, exterior tubular body 12 and the interior tubular body 13 can be configured into an asymmetrical arrangement so as to accommodate the flexcircuit or ribbon thermocouple. This asymmetrical arrangement can provide additional room for the flexcircuit or ribbon thermocouple and its plurality of traces or wires. However, surprisingly the asymmetrical shape of the asymmetrical gap 52 between the exterior tubular body 12 and the interior tubular body 13 does not adversely affect the delivery of drug through the catheter and to the treatment zone.

In some embodiments, the ribbon thermocouple design of FIGS. 2D-2I can include a gap between each of the pair of wires that are configured to form a thermocouple. In some examples, the distance between the conductors of each of the wires is closer together than the distance between each of the pair of wires that are configured to form a thermocouple. In some embodiments, this can help with the forming of the thermocouples. The distance between each of the pair of wires can aid in the removal of insulation material and the subsequent electrical connection of the exposed conductors. As discussed above, in some embodiments, the formation of an electrical connection of the exposed conductors can be through welding, soldering, or other electrical coupling method.

Ultrasound Catheters

Turning back to FIG. 1E, to provide access to the interior of the catheter 10, the proximal region 14 can include a distal hub 65 that can provide access to the asymmetrical gap 52 and a proximal hub 60 that can be configured to provide access to the central lumen 51. With reference to FIGS. 1B and 1E, a proximal end of the exterior tubular body 12 can extend through a nose cone 70 and can be coupled to the distal hub 65 through by a barbed fitting on the distal hub 65. In this manner, the distal hub 65 can provide access to asymmetrical gap 52 between the tubular body 12 and the internal tubular body 13 as shown in FIG. 2. Fluid lumen 30 includes a gap 52 between the exterior tubular body 12 and the internal tubular body 13. With reference to FIGS. 1B and 2, the fluid lumen inlet port 32 and the cable port 47 are in communication with this asymmetrical gap 52. That is to say, the fluid lumen inlet port 32 is a first fluid injection port in fluid communication with the gap 52. A cable 45 can extend through the cable port 47 and can be coupled the temperature sensor 20. The interior tubular body 13 can extend through the distal hub 65 and can be coupled to the proximal hub 60 such that the interior of the proximal hub 60 is in communication with the central lumen 51. As shown in FIG. 1B, the interior fluid port 46 is in communication with the interior of the proximal hub 60 such that fluid injected through the fluid port 46 will enter the central lumen 51. Thus, interior fluid port 46 is a fluid injection port in fluid communication with the interior of the interior tubular body 13. As illustrated, the proximal hub 60 can, in turn, be connected to a proximal end of the internal tubular body 13 by a barbed fitting on the proximal hub. While in the illustrated embodiment, barb fittings are used to connect the exterior tubular body 12 and the internal tubular body 13 to the distal hub 65 and proximal hub 60 respectively, in modified embodiments, other connection configurations can be such as such as flanged and threaded flared connections.

Figure 1F:
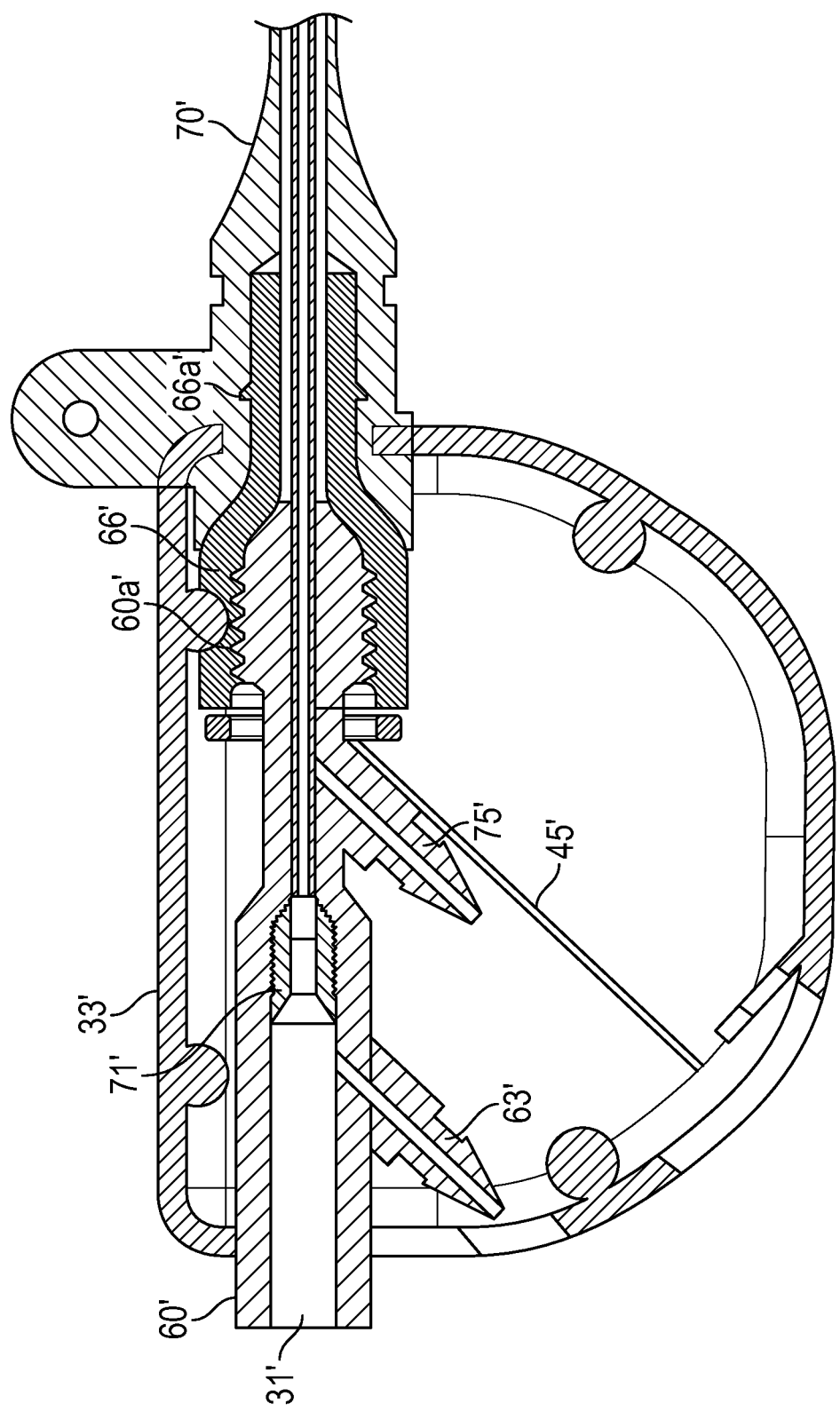
FIG. 1F is an enlarged cross-sectional side view of a modified hub portion of the ultrasonic catheter of FIG. 1A.

For example, FIG. 1F illustrates a cross-sectional view of another embodiment of the backend hub 33'. As discussed with regard to the backend hub 33 in FIGS. 1B & 1E, the backend hub 33' can include a plurality of components that can provide access to the interior of the exterior tubular body 12. In some embodiments, the backend hub 33' can be configured to retain a proximal hub 60'.

Unlike the hub described in FIGS. 1B & 1E which is composed of a distal hub 65 and a proximal hub 60, the proximal hub 60' spans the entire length of the backend hub 33' and provides a fluid connection to the interior of the catheter 10. The proximal end of the interior tubular body 13 is secured to the inside surface of the backend hub 33' through a threaded flared fitting 71'.

The proximal hub 60' also includes a plurality of inlets to provide fluid communication with the interior of the catheter 10. The proximal hub 60' can have a proximal access port 31'. In some examples, the proximal hub 60' can include a second barb inlet 75' which can provide fluid communication to the gap 52 and a third barb inlet 63' that can provide access to the central lumen 51. In the embodiment illustrated in FIG. 1F, the cable 45' can be provided through an opening in the proximal hub 60'. As discussed above, the cable 45' can provide an electrical connection for the temperature sensor 20.

The proximal hub 60' can be secured to the nosecone 70' through a plurality of components. As illustrated in FIG. 1F, the distal end of the proximal hub 60' includes a plurality of threads 66a' that is secured to the inside surface of a flared fitting 66'. The flared fitting 66' can further include a plurality of barbed connectors that protrude from the surface of the nose cone 70 to secure the proximal hub 60' and flanged fitting 66' to the inside of the nosecone 70'.

With continued reference to FIGS. 1B and 1E, the distal hub 65 can include a first barb inlet 69 can be coupled to a connector 73 through which a cable 45 can extend. The temperature sensor 20 can be connected to the cable with one or both components extending partially through the first barb inlet 69 and connector 73. The distal hub 65 can also include a second barb inlet 75 which can be connected to the inlet port 32 to provide fluid communication to the gap 52. The proximal hub 60 can include a third barb inlet 63 and a proximal access port 31 that provides access to the central lumen 51. The third barb inlet 63 can be connected to the interior fluid port 46. In a modified embodiment, one or more of the first, second and third barb inlets 69, 75 and/or 63 can be replaced with flanged and/or flared fittings.

As discussed above, a plurality of components may be attached to the inlets of the distal hub 65 and proximal hub 60 to be in fluid communication with the interior of the exterior tubular body 12. As illustrated in FIGS. 1B-1E, a cable 45 can be attached to or extend through the first barb inlet 69 to form an electrical connection with the temperature sensor 20. In some embodiments the cable 45 is secured to the first barb inlet 69 through the use of connector 73 which can include an adhesive lining. In some embodiments, the cable 45 can include a connector 101 to the control system 100. Similarly, the fluid line 91 with fluid inlet port 32 can be attached to the second barb inlet 75 to provide fluid access to the asymmetrical gap 52. As well, in some embodiments, the cooling fluid line 92 with cooling fluid inlet port 46 can be attached to the barb inlet 63 to provide fluid access to the cooling fluid inlet port 46. The fluid inlet port 32 and cooling fluid inlet port 46 can be provided with luer fittings to facilitate connections to other components.

In order to secure the aforementioned components in the proximal region 14 of the catheter 10, the catheter 10 can include a housing structure to secure the fluid line 91 and cooling fluid line 92 to the inlets of the distal hub 65 and proximal hub 60. In some examples, as illustrated in FIG. 1E, the catheter 10 can include a backend hub 33 that has a first and second portion. The two parts of the backend hub 33 can be disposed about the proximal hub 60 and distal hub 65 so as to secure the distal hub 65 and proximal hub 60 in place. In some examples, the 65 and proximal hub 60 is further secured by the nosecone 70. In some embodiments, the nosecone 70 can be further retained by the backend hub 33 which secures the nosecone 70 at the distal end of the distal hub 65.

As noted above, in some embodiments, the arrangement of the exterior tubular body 12 and the interior tubular body 13 can be configured into an asymmetrical arrangement so as to accommodate the temperature sensor 20. As illustrated in FIG. 2, the central lumen 51 and temperature sensor 20 are located within the fluid delivery lumen 30. The cross-section of the exterior tubular body 12, as illustrated in FIG. 2, can be substantially constant along the length of the catheter 10. Thus, in such embodiments, substantially the same cross-section is present in both the proximal region 14 and the distal region 15 of the catheter 10, including the energy delivery section 18. In certain embodiments, the same or asymmetrically shaped cross-section is present along at least 50% of the length of the catheter, in other embodiments, at least 75% of the length of the catheter and in other embodiments at least 90% of the length of the catheter.

In some embodiments, the central lumen 51 has a minimum diameter greater than about 0.030 inches (greater than about 0.076 cm). In other embodiments, the central lumen 51 has a minimum diameter greater than about 0.037 inches (greater than about 0.094 cm), although other dimensions may be used in other applications. As described above, the central lumen 51 can extend through the length of the exterior tubular body 12. As illustrated in FIG. 1C, the central lumen 51 can have a distal exit port 29 and a proximal access port 31. As noted above, in some embodiments, the proximal access port 31 forms part of the backend hub 33, which is attached to the proximal region 14 of the catheter 10. In some examples, the backend hub 33 can further include cooling fluid inlet port 46 which is hydraulically connected to the central lumen 51. In some embodiments, the backend hub 33 can also include a fluid inlet port 32, which is in hydraulic connection with the asymmetrical gap 52 in the fluid delivery lumen 30, and which can be hydraulically coupled to a source of drug or therapeutic compound via a hub such as a Luer fitting. This embodiment of the disclosure therefore comprises a first fluid injection port (fluid inlet port 32) in fluid communication with the gap 52.

The central lumen 51 can be configured to receive an inner core 34 comprising a plurality of ultrasound radiating members extending along a length of the ultrasound catheter. FIG. 3 illustrates an embodiment of elongate inner core 34, which can be inserted into the central lumen 51. In some embodiments, the elongate inner core 34 can include a proximal region 36 and a distal region 38. A proximal hub 37 can be fitted on the inner core 34 at one end of the proximal region 36. As will be described below, in an arrangement, one or more ultrasound radiating members can be positioned within an inner core 34 located within the distal region 38. The ultrasound radiating members 40 can form an ultrasound assembly 42, which will be described in detail below. In one embodiment, when the inner core 34 can be positioned within the central lumen such that the ultrasound assembly 42 is positioned generally within the energy delivery section 18 of the catheter 10. As noted above, in one embodiment, the joints 212, 213, 214, 215, 216 of the flex circuit can be positioned adjacent the ultrasound assembly 42 and/or within the energy delivery section 18 of the catheter 10 and/or the thermocouple junctions of a the ribbon thermocouple can be positioned adjacent the ultrasound assembly 42 and/or within the energy delivery section 18 of the catheter.

FIGS. 1G-1J illustrate another embodiment of a back end hub 745, which can be used in the embodiments describe herein. As with the other embodiments, the hub 745 can be coupled to the, the exterior tubular body 12, the interior tubular body 13, and a plurality of inlets. In some examples, the ultrasonic catheter 700 can include a plurality of inlets. For example, the ultrasonic catheter 700 can include a first barb inlet 740, a second barb inlet 750, and a proximal access port 755.

Figure 1G:
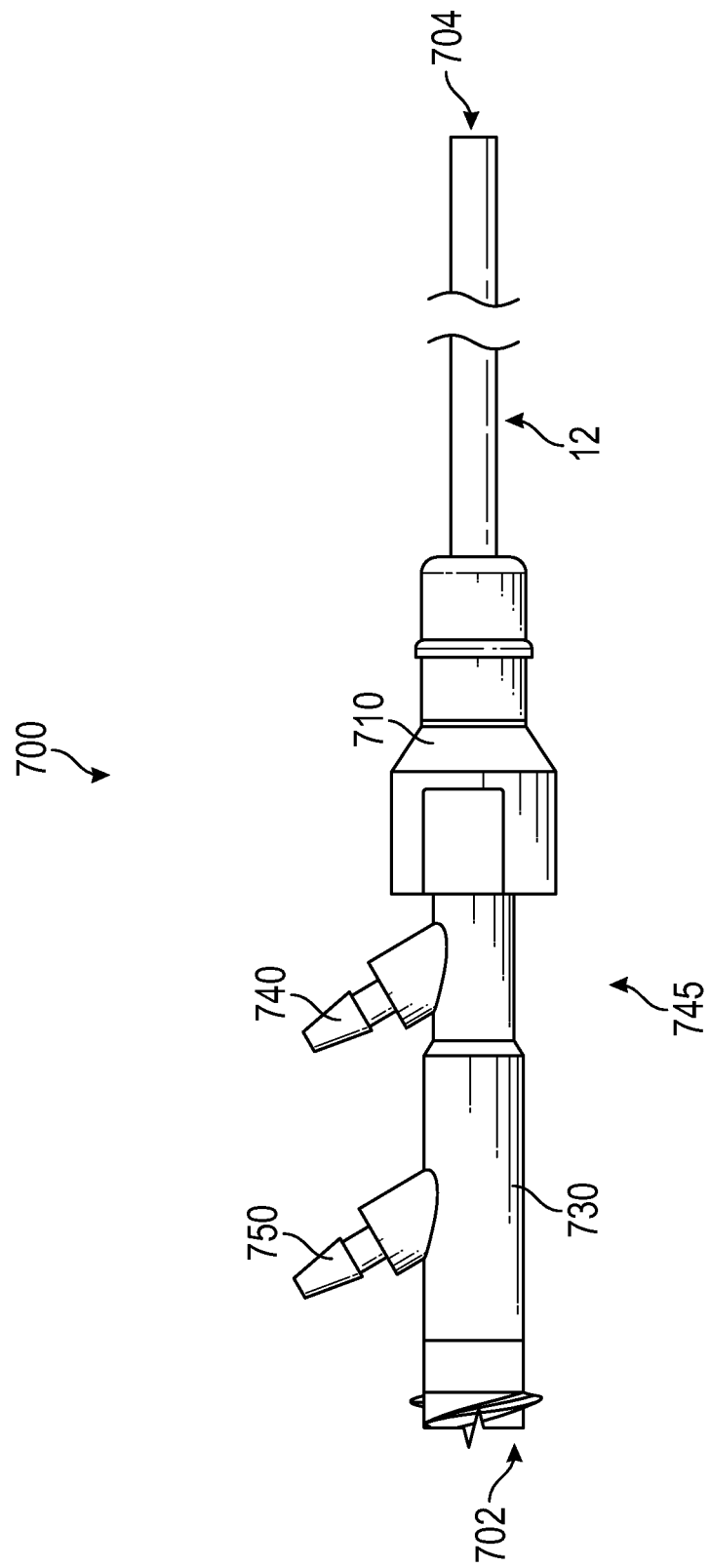
FIG. 1G is a side view of an embodiment of the hub portion of the ultrasonic catheter configured for insertion into the human body.
Figure 1H:
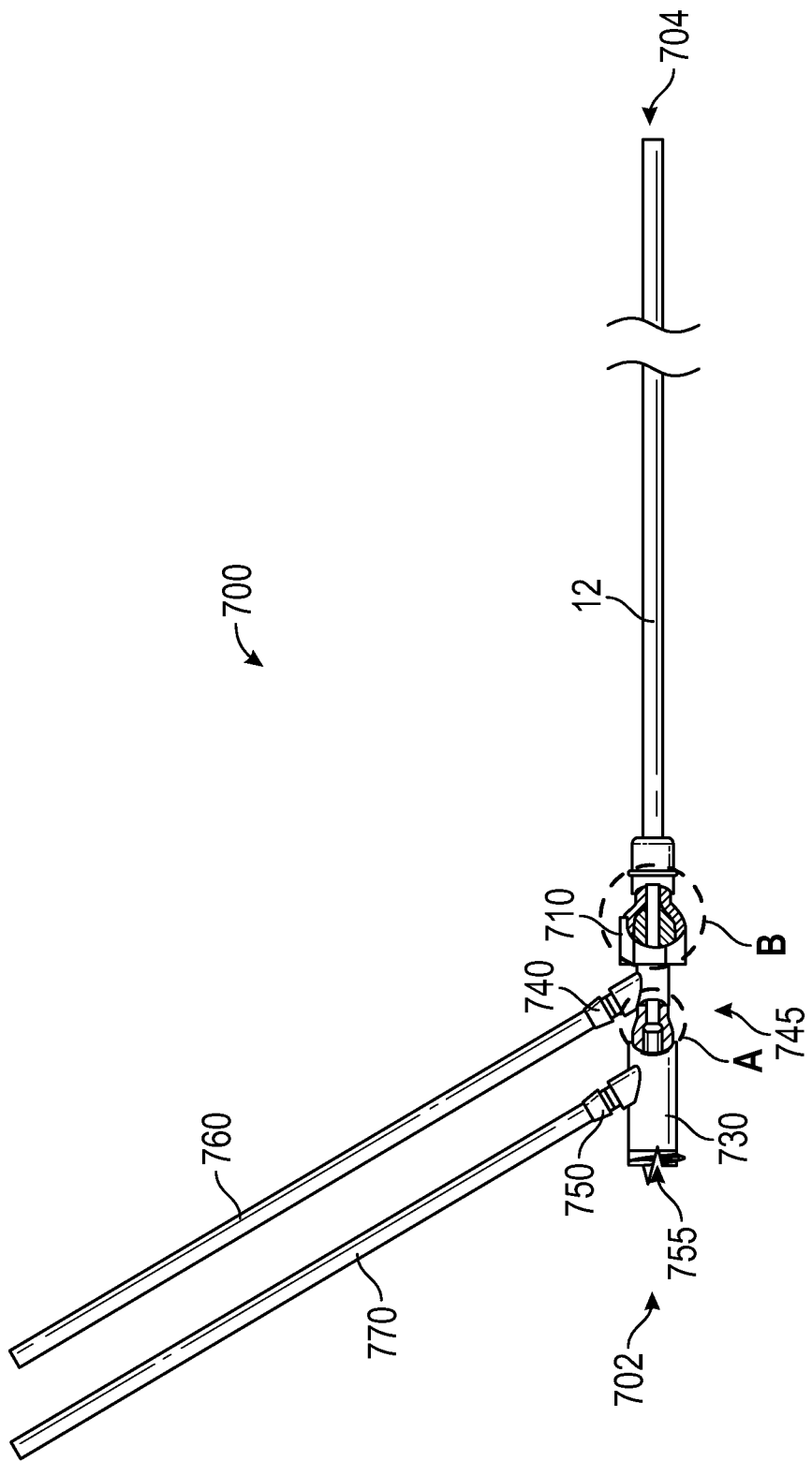
FIG. 1H is a side view of the embodiment of the hub portion of the ultrasonic catheter of FIG. 1G with attached fluid tubes configured for insertion into the human body.

In some embodiments, the hub 745 of the ultrasonic catheter 700 can be composed of a plurality of nested components that are sealed together. As illustrated in FIGS. 1G-1H, in some examples, the hub 745 can be composed of a cap 710 and a manifold body 730. A cross-section of each of the portions of the hub 745 is illustrated in greater detail in FIGS. 1I-1J. In some examples, the components of the hub 745 can be composed of a high density poly ethylene ("HDEV"). In some embodiments, the components of the hub 745 can be composed of a polycarbonate.

Figure 1I:
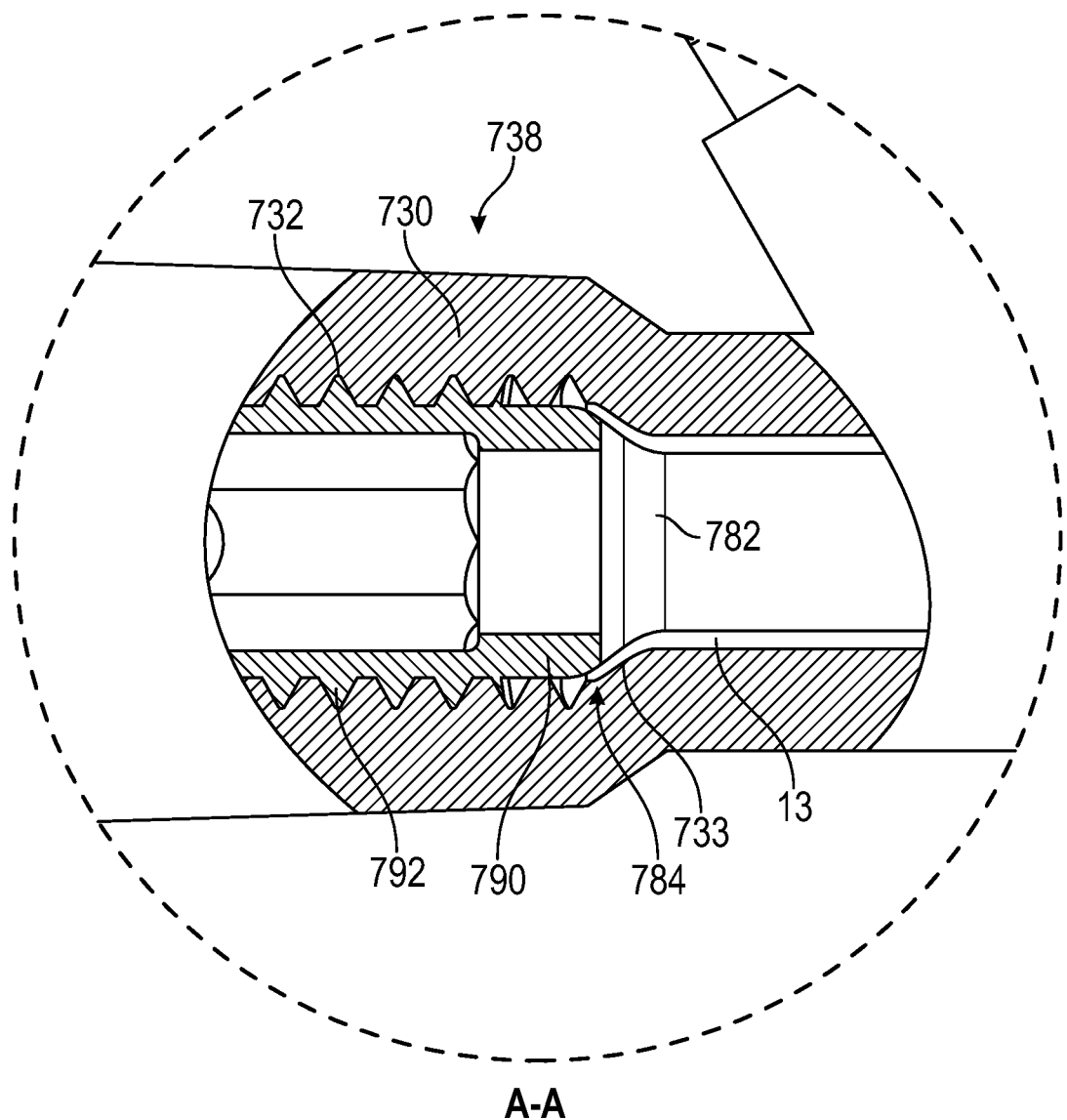
FIG. 1I is an enlarged cross-sectional view of the hub portion of the ultrasonic catheter of FIG. 1H along section A-A
Figure 1J:
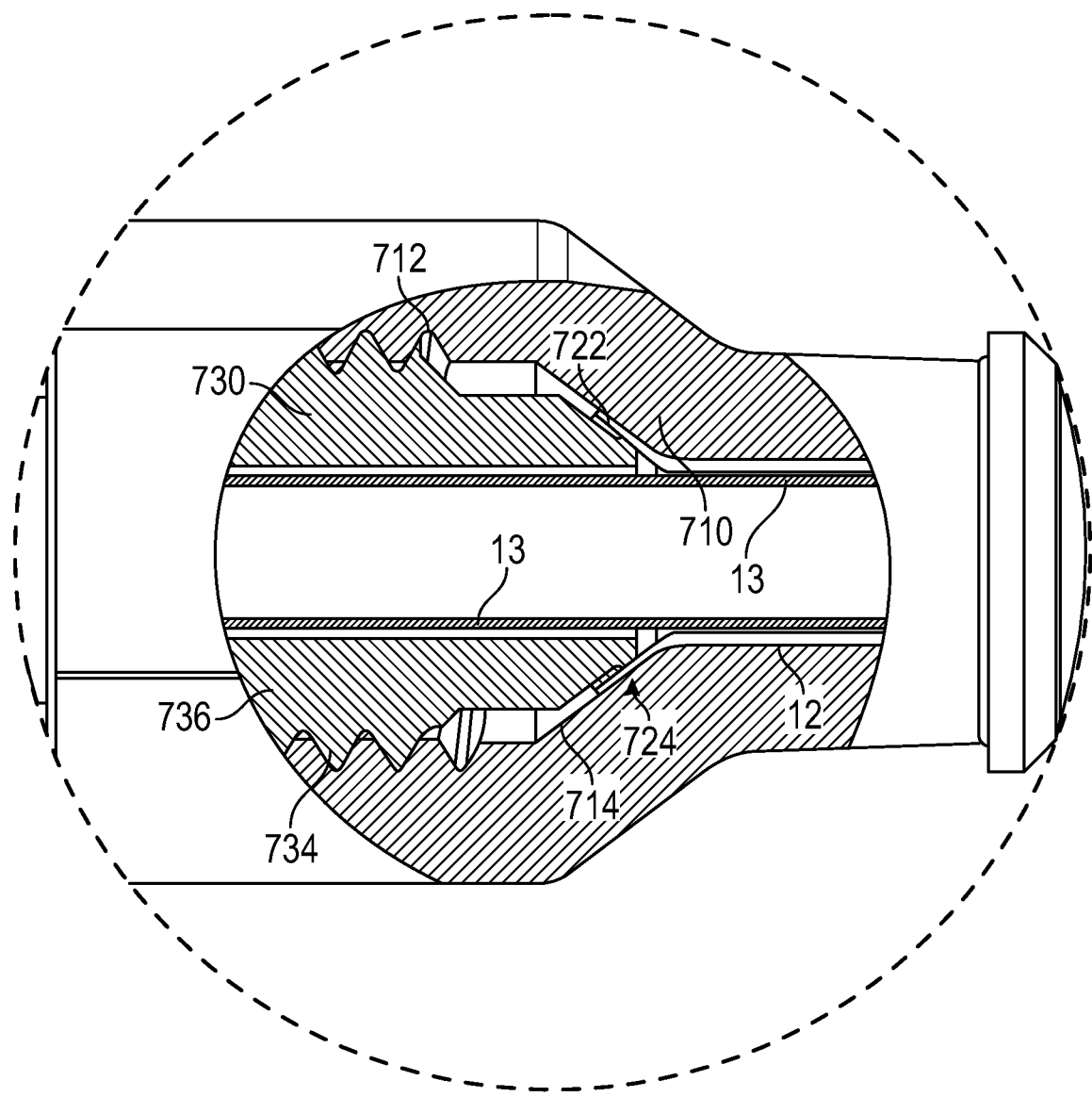
FIG. 1J is an enlarged cross-sectional view of the hub portion of FIG. 1H along section B-B.

Turning first to FIG. 1J, illustrated is a cross-section along circle B-B of the cap 710 in FIG. 1H. In some embodiments, the cap 710 is disposed about a distal end of the distal end 736 of the manifold body 730. As shown, in some examples, the cap 710 has internal threads 312 that are disposed about the internal surface of the cap 710. The cap internal threads 712 are configured to engage with the external threads 734 disposed about the external surface of the distal end 736. As will be discussed in more detail below, in some embodiments, the manifold body 730 and the cap 710 have an interior lumen that secures the exterior tubular body 12 and interior tubular body 13.

Figure 1K:
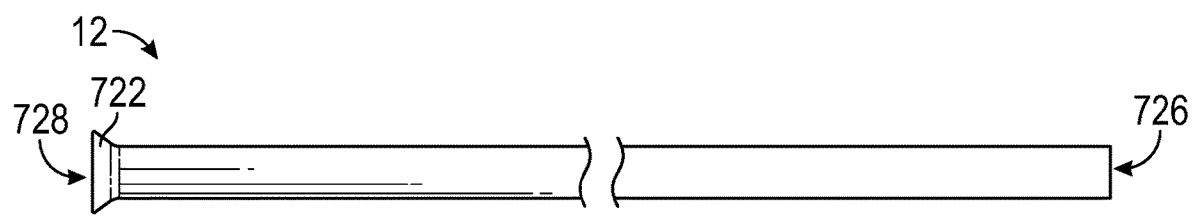
FIG. 1K is a side view of the exterior tubular body of the hub portion of FIG. 1G.

In some embodiments, the cap 710 can include an internal taper 714 that reduces in diameter. As shown in FIG. 1J, the internal taper 714 can accommodate a flared end 722 of the exterior tubular body 12. FIG. 1K illustrates a side view of an embodiment of the exterior tubular body 12. As illustrated, the exterior tubular body 12 can include a distal end 726 and a proximal end 728. In some embodiments, the flared end 722 of the exterior tubular body 12 can be located at the proximal end 728. In some examples, the distal end 736 of the manifold body 730 can, when secured within the cap 710, be configured to engage with and secure the flared end 722 of the exterior tubular body 12. As the distal end 736 of the manifold body 730 is rotated within the cap 710, the distal end 736 of the manifold body 730 can apply pressure to the flared end 722 to form a seal 724. As will be discussed in more detail below, the seal 724 can allow fluid to be pumped into the exterior tubular body 12 and prevent fluid from leaking out of the exterior tubular body 12.

In some examples, as shown in FIG. 1J, the exterior tubular body 12 can be disposed about the interior tubular body 13. As discussed above, the interior tubular body 13 can be configured to accommodate the inner core 706. In some embodiments, as will be discussed in more detail below, the interior tubular body 13 can provide for a coolant to flow through the interior tubular body 13 to maintain the temperature of the inner core 706. In some embodiments, as will be discussed in more detail below, the exterior surface of the interior tubular body 13 and the interior surface of the exterior tubular body 12 can provide for a drug or therapeutic compound to flow through.

Turning next to FIG. 1I, illustrated is a cross-section along circle A-A of the manifold body 730 of the hub 745. In some embodiments, the proximal end 738 of the manifold body 730 can be configured to engage with and secure the interior tubular body 13. In some examples, the proximal end 738 of the manifold body 730 can include internal threads 732 that are disposed along the inner surface of the manifold body 730. In some embodiments, the proximal end of the interior tubular body 13 can be engaged with a threaded insert 790. The external threads 792 of the threaded insert 790 can be rotated to engage with the internal threads 732 of the manifold body 730.

In some embodiments, the manifold body 730 can include an internal taper 733 that reduces in diameter. As shown in FIG. 1I, the internal taper 733 can accommodate a flared end 782 of the interior tubular body 13. In some examples, the distal end of the threaded insert 790 can, when secured within the manifold body 730, be configured to engage with and secure the flared end 782 of the interior tubular body 13. As the threaded insert 790 is secured within the proximal end 738 of the manifold body 730, the distal end of the threaded insert 790 can apply pressure to the flared end 782 to form a seal 784. As will be discussed in more detail below, the seal 784 can prevent fluid from leaking out of the interior tubular body 13.

As noted above, the hub 745 can include a number of openings to allow access to the interior of the exterior tubular body 12 and the interior tubular body 13 as shown in FIGS. 2 and 2A. In some embodiments, the hub 745 can include the first barb inlet 740. The first barb inlet 740 can be located near the distal end 736 of the manifold body 730. In some embodiments, the first barb inlet 740 can be fluidly connected to the opening between the interior surface of the exterior tubular body 12 and the exterior surface of the interior tubular body 13. This can be, for example, the asymmetric gap 52 of FIG. 2. The first barb inlet 740 can be fluidly connected to a drug inlet tube 760 and allow a drug or a therapeutic compound to flow from the drug inlet tube 760 and into the exterior tubular body 12 such that the drug or therapeutic compound flows between the interior surface of the exterior tubular body 12 and the exterior surface of the interior tubular body 13.

In some examples, as illustrated in FIGS. 1G-1H, the hub 745 can include the second barb inlet 750. The second barb inlet 750 can be located near the proximal end 738 of the manifold body 730. In some embodiments, the second barb inlet 750 can be fluidly connected to the interior of the interior tubular body 13. This can be, for example, through the central lumen as illustrated in FIG. 2. The second barb inlet 750 can be fluidly connected to a coolant inlet tube 770 and allow a cooling fluid to flow through the interior tubular body 13. As noted above, in some examples, the cooling fluid can help to maintain the temperature of the inserted inner core.

In some embodiments, as illustrated in FIGS. 1G-1H, the hub 745 can include a proximal access port 755 that can provide access to the interior of the interior tubular body 13. In some embodiments, the proximal access port 755 can be configured to allow an inner core (for example the inner core 34 of FIG. 2 or the inner core 706 of FIG. 2A) to be inserted into the ultrasonic catheter 700.

FIGS. 1L-1O illustrate another embodiment of hub 845 which can be used with any of the embodiments described herein. In some embodiments, the ultrasonic catheter 800 can include a hub 845, an exterior tubular body 12, an interior tubular body 13, and a plurality of inlets. For example, the ultrasonic catheter 800 can include a first barb inlet 822, a second barb inlet 832, and a proximal access port 855.

Figure 1L:
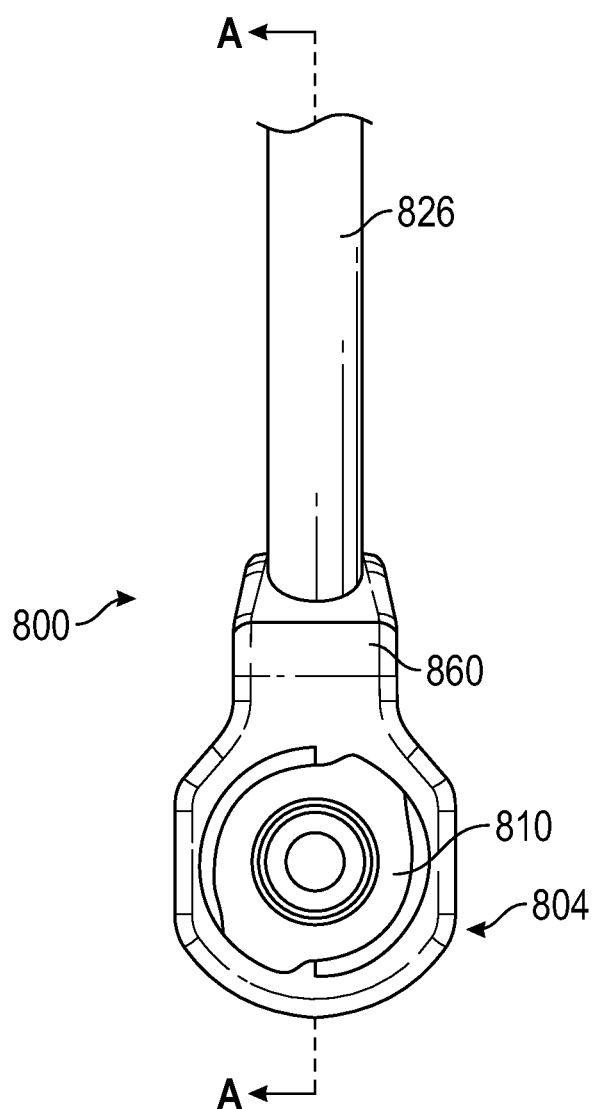
FIG. 1L is a front view of another embodiment of the hub portion of the ultrasonic catheter configured for insertion into the human body.
Figure 1M:
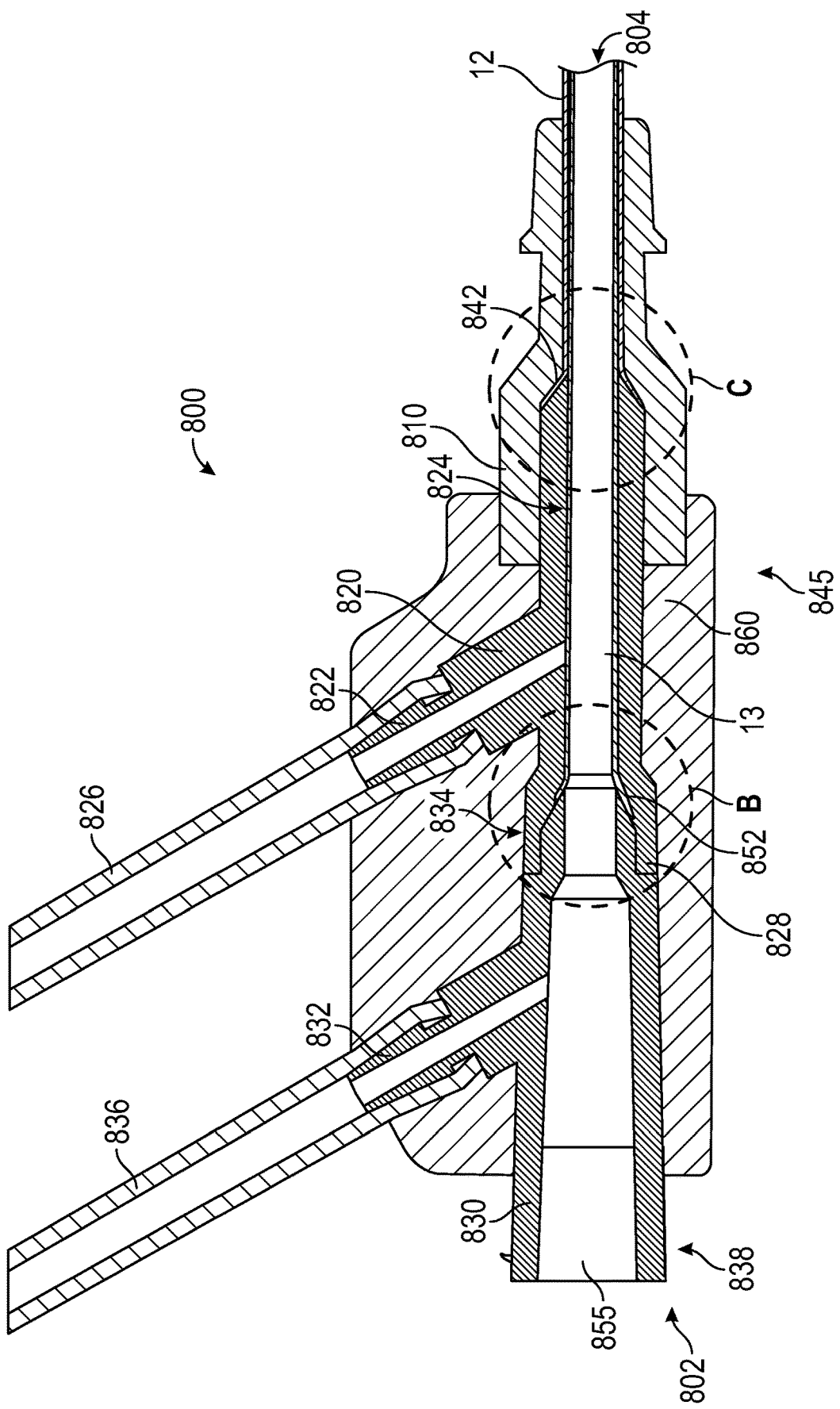
FIG. 1M is a cross-sectional view of the hub portion of the ultrasonic catheter of FIG. 1L.

In some embodiments, the hub 845 of the ultrasonic catheter 800 can be composed of a plurality of nested components that are secured together. In some examples, the various components of the hub 845 can be composed of a polycarbonate. As will be discussed in more detail below, the hub 845 can include an external overmold that provides an easy and secure way of attaching the various components of the hub 845. As illustrated in FIG. 1L-1M, in some examples, the hub 845 can be composed of a manifold cap 810, a distal manifold 820, a proximal manifold 830, and an overmold 860. A cross-section of each of the junctions between each of the components of the hub 845 is illustrated in greater detail in FIGS. 1N-1O.

Figure 1N:
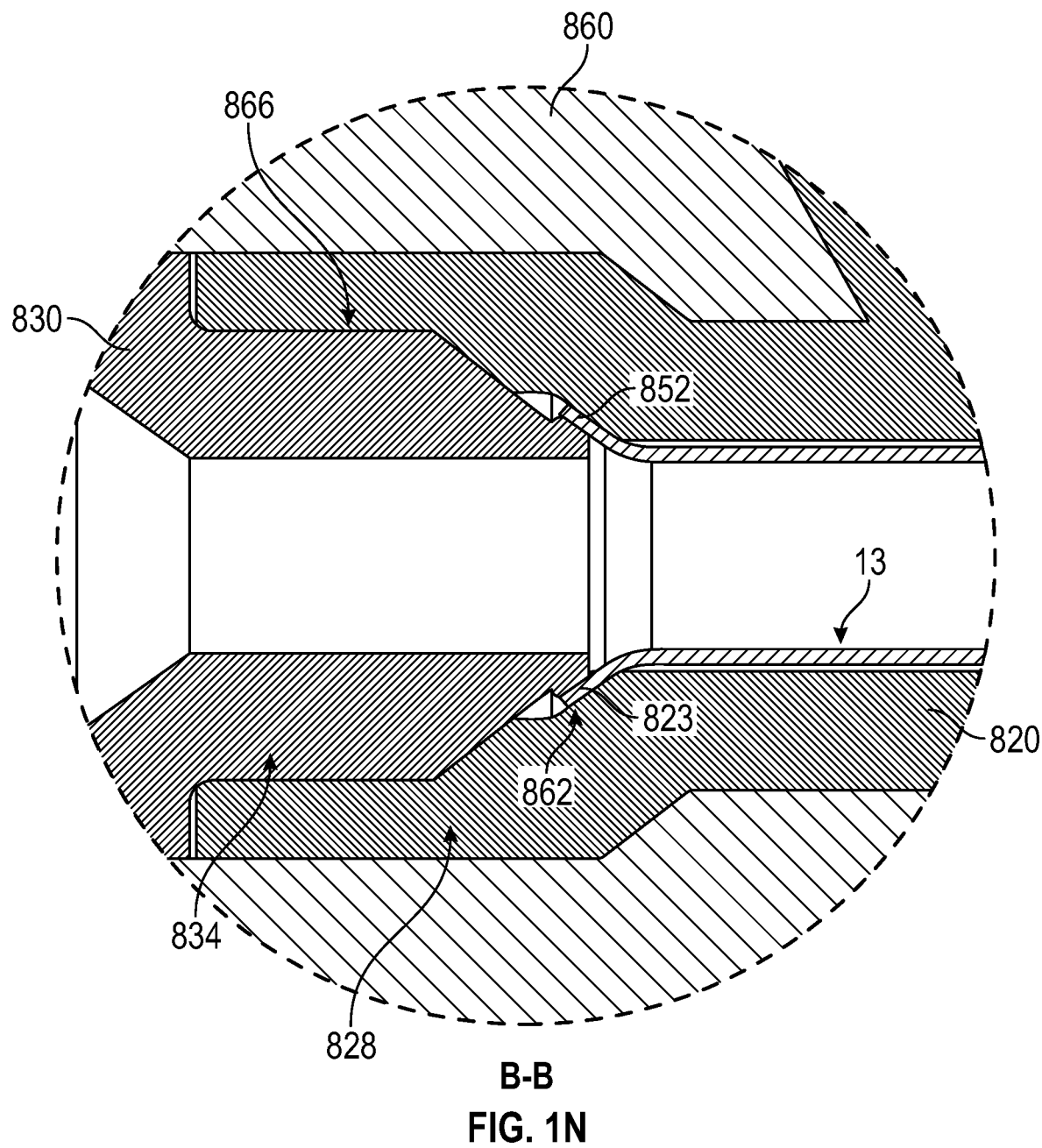
FIG. 1N is an enlarged cross-sectional view of the hub portion of the ultrasonic catheter of FIG. 1L along section B-B.
Figure 1O:
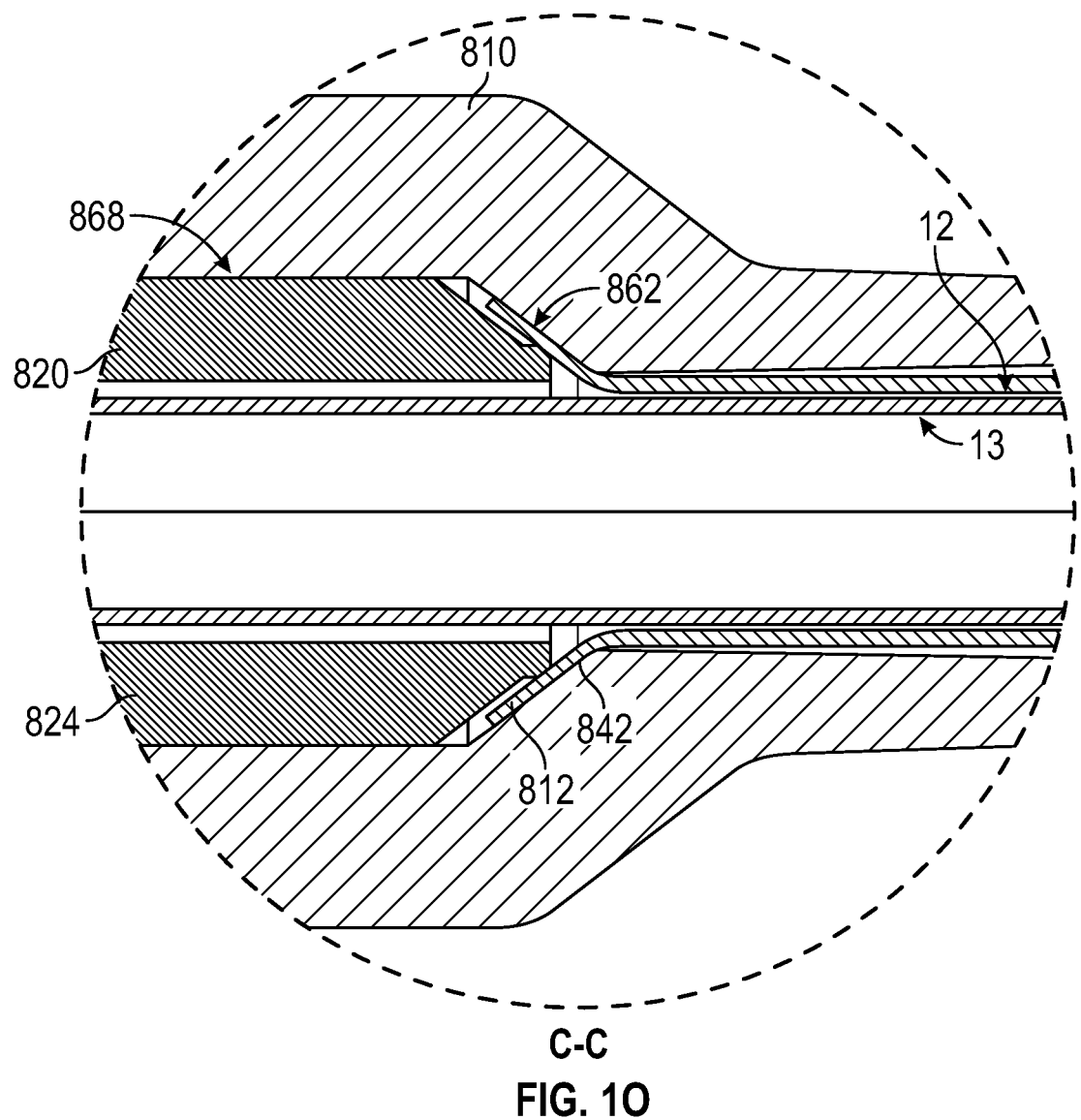
FIG. 1O is an enlarged cross-sectional view of the hub portion of the ultrasonic catheter of FIG. 1L along section C-C.

Turning first to FIG. 1O, illustrated is a cross-section along circle C-C of the manifold cap 810 in FIG. 1M. In some embodiments, the manifold cap 810 is disposed about a distal end 824 of the distal manifold 820. As illustrated, in some examples, the manifold cap 810 is press fit 868 about the distal end 824 of the distal end 824.

In some embodiments, the manifold cap 810 can include an internal taper 812 that reduces in diameter. As shown in FIGS. 1M and 1O, the internal taper 812 can accommodate a flared end 842 of the exterior tubular body 12. In some examples, when the distal end 824 of the distal manifold 820 is secured within the manifold cap 810, the distal manifold 820 can be configured to engage with and secure the flared end 842 of the exterior tubular body 12. In some embodiments, as the distal end 824 of the distal manifold 820 is inserted within the manifold cap 810, the distal end 824 of the distal manifold 820 can apply pressure to the flared end 842 to form a seal 862. As will be discussed in more detail below, the seal 862 can allow fluid to be pumped into the exterior tubular body 12 and prevent fluid from leaking out of the exterior tubular body 12.

In some examples, as shown in FIGS. 1M and 1O, the exterior tubular body 12 can be disposed about the interior tubular body 13. As discussed above, the interior tubular body 13 can be configured to accommodate an inner core. In some embodiments, as will be discussed in more detail below, the interior tubular body 13 can provide for a coolant to flow through the interior tubular body 13 to maintain the temperature of the inserted inner core. In some embodiments, as will be discussed in more detail below, the exterior surface of the interior tubular body 13 and the interior surface of the exterior tubular body 12 can provide for a drug or therapeutic compound to flow through.

Turning next to FIGS. 1M-1N, illustrated is a cross-section along circle B-B of the connection between the proximal manifold 830 and the distal manifold 820 of the hub 845. In some embodiments, the proximal end 828 of the distal manifold 820 can be disposed about the distal end 834 of the proximal manifold 830. In some examples, the distal manifold 820 is press fit 866 about the proximal manifold 830.

In some embodiments, the proximal end 828 of the distal manifold 820 can be configured to engage with and secure the interior tubular body 13. In some embodiments, the distal manifold 820 can include an internal taper 823 that reduces in diameter. As shown in FIG. 1N, the internal taper 823 can accommodate a flared end 852 of the interior tubular body 13. In some examples, the distal end 834 of the proximal manifold 830 can, when secured within the proximal end 828 of the distal manifold 820, be configured to engage with and secure the flared end 852 of the interior tubular body 13. In some embodiments, the distal end 834 of the proximal manifold 830 can apply pressure to the flared end 852 to form a seal 862. As will be discussed in more detail below, the seal 862 can prevent fluid from leaking out of the interior tubular body 13.

As noted above, the hub 845 can include a number of openings to allow access to the interior of the exterior tubular body 12 and the interior tubular body 13 as shown in FIGS. 2 and 2A. In some embodiments, the hub 845 can include the first barb inlet 822. The first barb inlet 822 can be located on the distal manifold 820. In some embodiments, the first barb inlet 822 can be fluidly connected to the opening between the interior surface of the exterior tubular body 12 and the exterior surface of the interior tubular body 13. This can be, for example, the asymmetric gap 52 of FIG. 2. In some embodiments, the drug inlet tube 826 can be disposed about the first barb inlet 822. The first barb inlet 822 can be fluidly connected to the drug inlet tube 826 and allow a drug or a therapeutic compound to flow from the drug inlet tube 826 and into the exterior tubular body 12 such that the drug or therapeutic compound flows between the interior surface of the exterior tubular body 12 and the exterior surface of the interior tubular body 13.

In some examples, as illustrated in FIG. 1M, the hub 845 can include the second barb inlet 832. The second barb inlet 832 can be located on the proximal manifold 830. In some embodiments, the proximal manifold 830 can be fluidly connected to the interior of the interior tubular body 13. This can be, for example, through the central lumen as illustrated in FIG. 2. In some embodiments, the coolant inlet tube 836 can be disposed about the second barb inlet 832. The second barb inlet 832 can be fluidly connected to the coolant inlet tube 836 and allow a cooling fluid to flow through the interior tubular body 13. As noted above, in some examples, the cooling fluid can help to maintain the temperature of the inserted inner core.

In some embodiments, as illustrated in FIG. 1M, the hub 845 can include a proximal access port 855 that can provide access to the interior tubular body 13. In some examples, the proximal access port 855 can be configured to allow an inner core (for example the inner core 34 of FIG. 2 or the inner core 706 of FIG. 2A) to be inserted into the ultrasonic catheter 800.

As discussed above, in some embodiments, the hub 845 can include an overmold 860. In some examples, the overmold 860 can be composed of a co-polyester. In some embodiments, the overmold 860 can be composed of a polyamide. The overmold 860 can be configured to seal and secure the various components of the hub 845.

Details and various embodiments of the inner core 34 and its operation of can be found in several patents and patent applications filed by EKOS Corporation of Bothell, Wash. including U.S. Pat. No. 7,220,239 and U.S. Patent Publication No. 2008/0171965, which are hereby incorporated by reference in their entirety.

Figure 4:
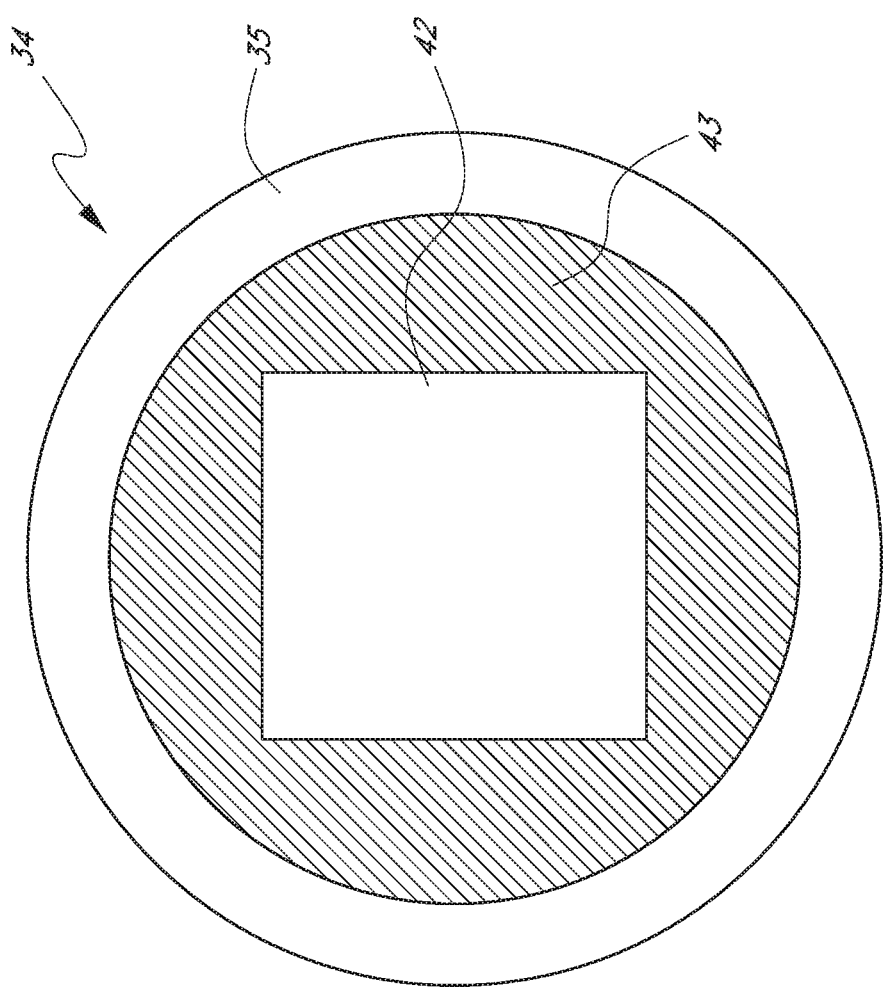
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 can have a cylindrical shape, with an outer diameter that permits the inner core 34 to be inserted into the central lumen 51 of the interior tubular body 13 via the proximal access port 31. Suitable outer diameters of the inner core 34 include, but are not limited to, about 0.010 inches to about 0.100 inches (about 0.025 cm to about 0.254 cm). In other embodiments, the outer diameter of the inner core 34 can be between about 0.020 inches and about 0.080 inches (about 0.051 cm to about 0.20 cm). In other embodiments, the inner core 34 can have an outer diameter of about 0.035 inches (about 0.089 cm).

Still referring to FIG. 4, the inner core 34 can include a cylindrical outer body 35 that houses the ultrasound assembly 42. The ultrasound assembly 42 can include wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 can be electrically connected to the backend hub 33, where the inner core 34 can be connected to a control system 100 via cable and through a connector (not shown). In one arrangement, an electrically insulating potting material 43 fills the inner core 34, surrounding the ultrasound assembly 42, thus preventing or limiting movement of the ultrasound assembly 42 with respect to the outer body 35. In one embodiment, the thickness of the outer body 35 is between about 0.0002 inches and about 0.010 inches (between about 0.0005 cm and about 0.025 cm). In another embodiment, the thickness of the outer body 35 is between about 0.0002 inches and about 0.005 inches (between about 0.0005 cm and about 0.01 cm). In yet another embodiment, the thickness of the outer body 35 is about 0.0005 inches (about 0.001 cm).

Figure 5:
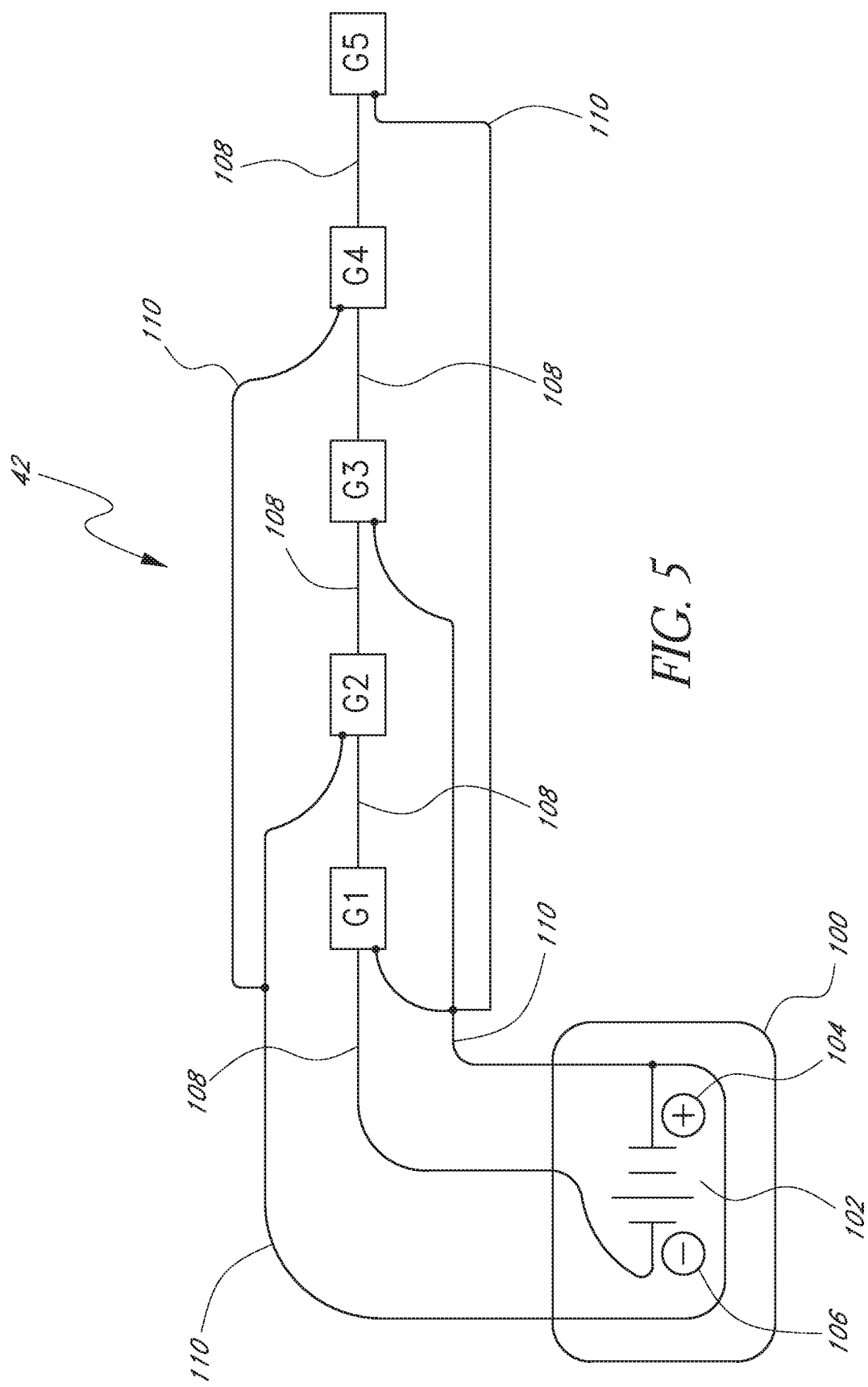
FIG. 5 is a schematic wiring diagram illustrating an exemplary technique for electrically connecting five groups of ultrasound radiating members to form an ultrasound assembly.
Figure 6:
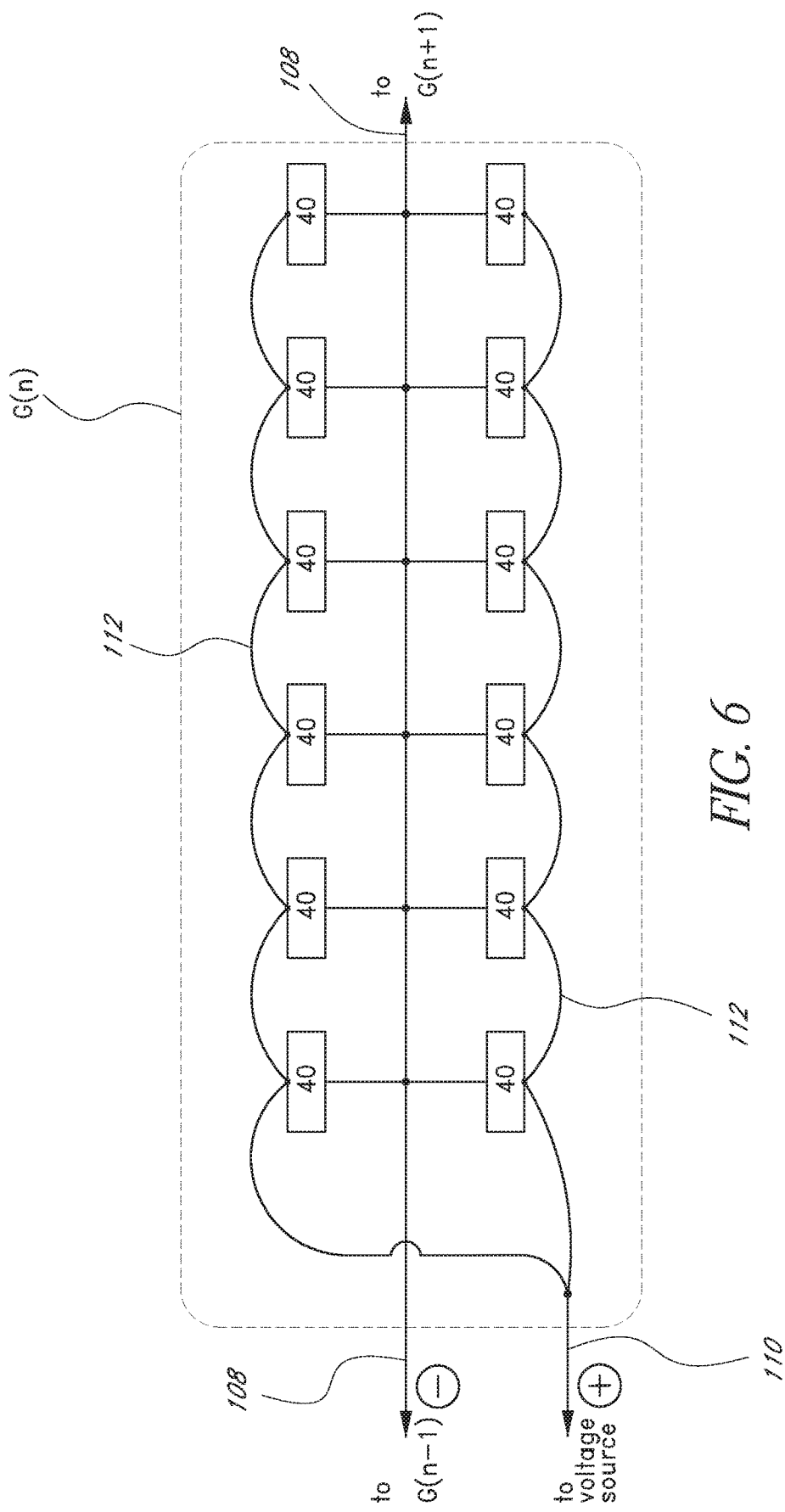
FIG. 6 is a schematic wiring diagram illustrating an exemplary technique for electrically connecting one of the groups of FIG. 5.

In some embodiments, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 can include five groups G1, G2, G3, G4, and G5 of ultrasound radiating members 40 that can be electrically connected to each other. The five groups are also electrically connected to the control system 100. In some embodiments, two, three, or four groups of ultrasound radiating member 40 may be electrically connected to each other and the control system 100.

In some embodiments, the ultrasound assembly 42 comprises five or less (i.e., one, two, three, four, or five) ultrasound radiating members 40. The ultrasound radiating members 40 may be divided into one or more groups as described above. The reduced or limited number of ultrasound radiating members 40 can allow the ultrasound assembly 42 to be driven at a higher power.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 16 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, vibration through a wire that is coupled to the ultrasound radiating member.

Still referring to FIG. 5, the control circuitry 100 can include, among other things, a voltage source 102. The voltage source 102 can comprise a positive terminal 104 and a negative terminal 106. The negative terminal 106 is connected to common wire 108, which connects the five groups G1-GS of ultrasound radiating members 40 in series. The positive terminal 104 can be connected to a plurality of lead wires 110, which each connect to one of the five groups G1-GS of ultrasound radiating members 40. Thus, under this configuration, each of the five groups GI-GS, one of which is illustrated in FIG. 6, can be connected to the positive terminal 104 via one of the lead wires 110, and to the negative terminal 106 via the common wire 108. The control circuitry can be configured as part of the control system 100 and can include circuits, control routines, controllers etc. configured to vary one or more power parameters used to drive ultrasound radiating members 40.

Referring now to FIG. 6, in one embodiment, each group G1-GS can comprise a plurality of ultrasound radiating members 40. Each of the ultrasound radiating members 40 can be electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
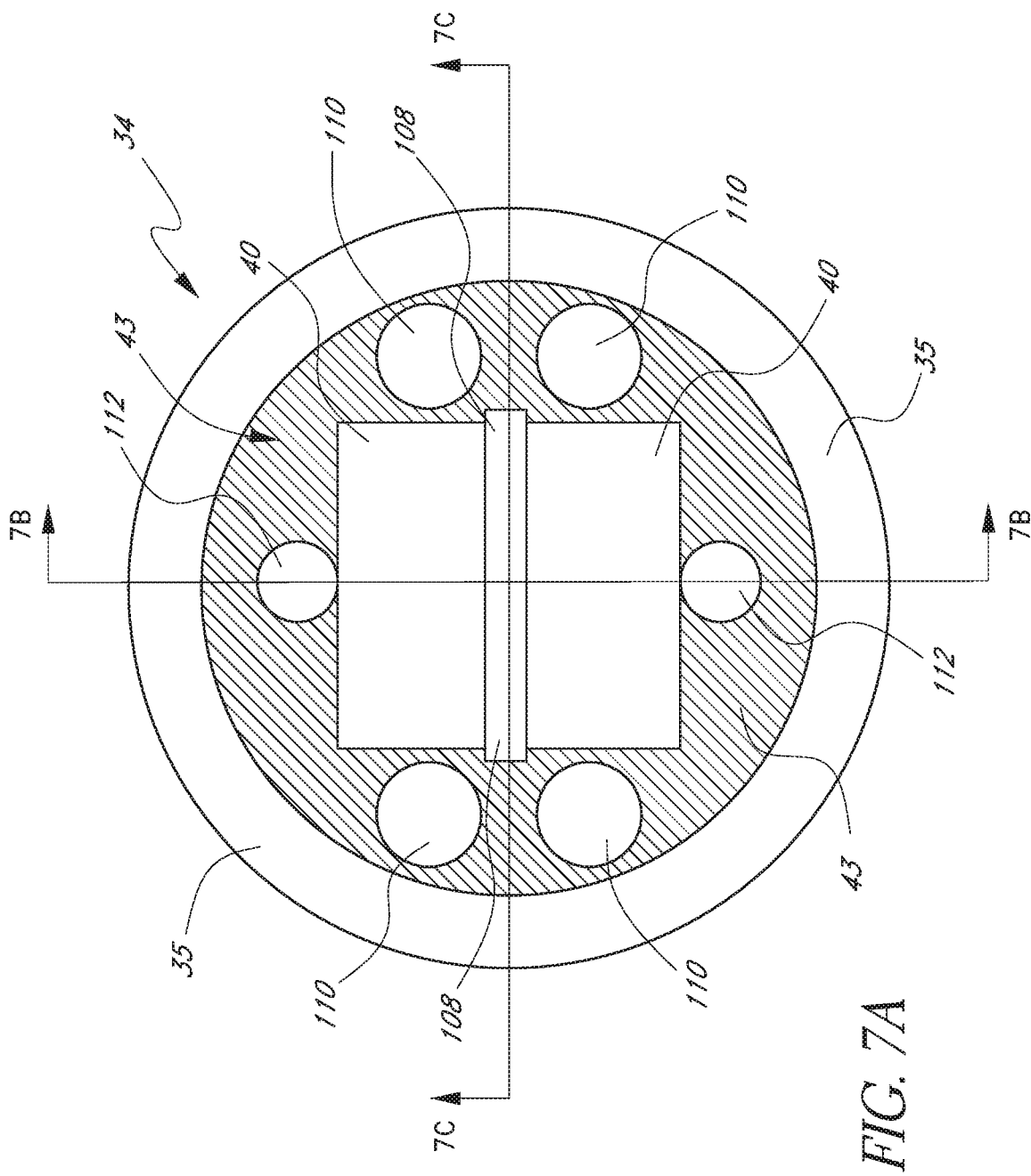
FIG. 7A is a schematic illustration of the ultrasound assembly of FIG. 5 housed within the inner core of FIG. 4.

FIG. 7A illustrates one technique for arranging the components of the ultrasound assembly 42 (as schematically illustrated in FIG. 5) into the inner core 34 (as schematically illustrated in FIG. 4). FIG. 7A illustrates a cross-sectional view of the ultrasound assembly 42 taken within group GI in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 can include an elongate, flat piece of electrically conductive material in electrical contact with a pair of ultrasound radiating members 40. Each of the ultrasound radiating members 40 can also be in electrical contact with a positive contact wire 312. Because the common wire 108 is connected to the negative terminal 106, and the positive contact wire 312 is connected to the positive terminal 104, a voltage difference can be created across each ultrasound radiating member 40. In some embodiments, the lead wires 110 can be separated from the other components of the ultrasound assembly 42, thus preventing interference with the operation of the ultrasound radiating members 40 as described above. For example, in some embodiments, the inner core 34 is filled with an insulating potting material 43, thus deterring unwanted electrical contact between the various components of the ultrasound assembly 42.

Figure 7B:
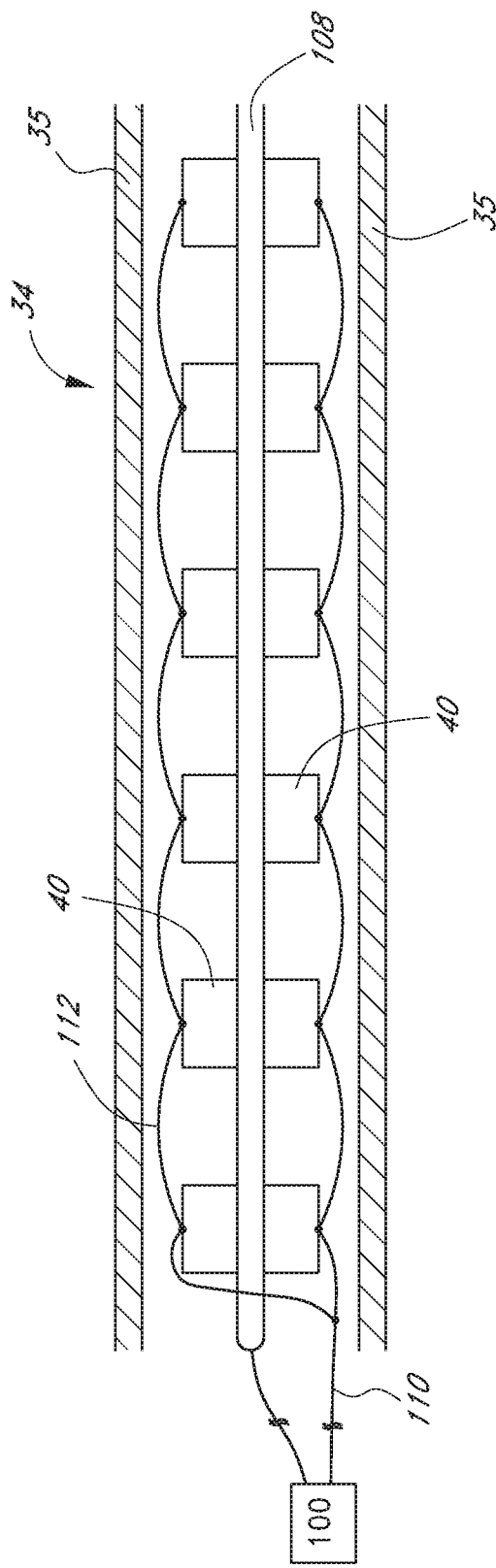
FIG. 7B is a cross-sectional view of the ultrasound assembly of FIG. 7A taken along line 7B-7B.
Figure 7C:
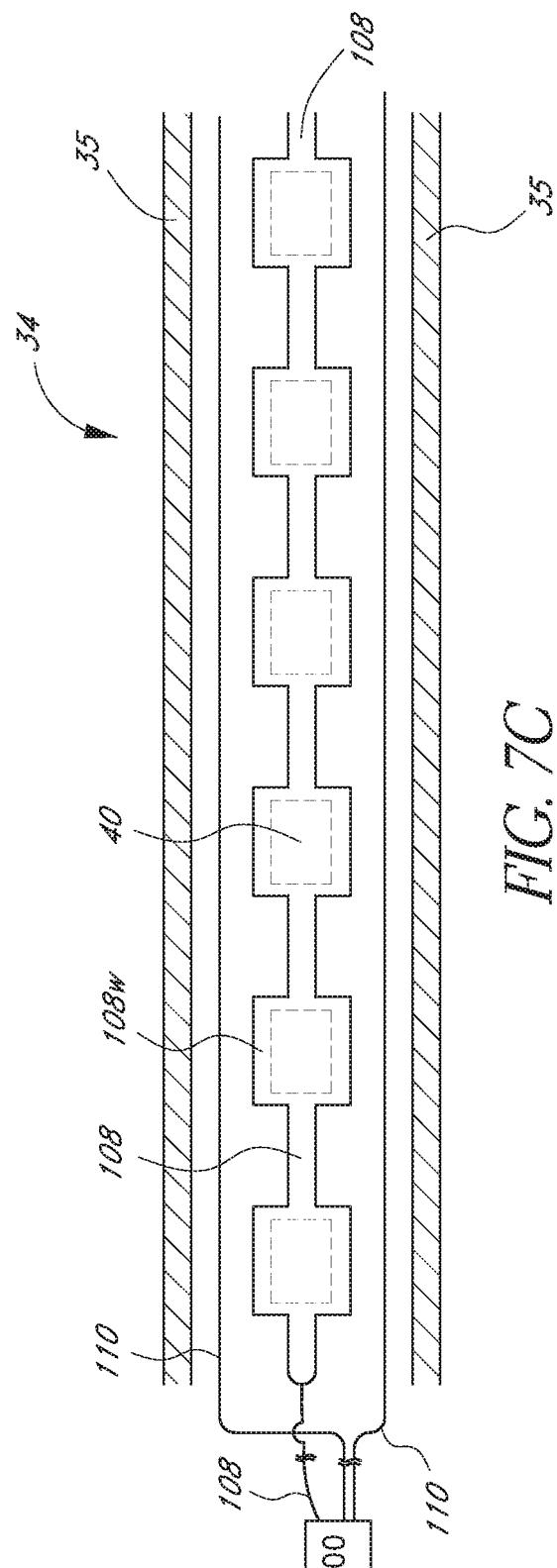
FIG. 7C is a cross-sectional view of the ultrasound assembly of FIG. 7A taken along line 7C-7C.

FIGS. 7B and 7C illustrate cross-sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 can include wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
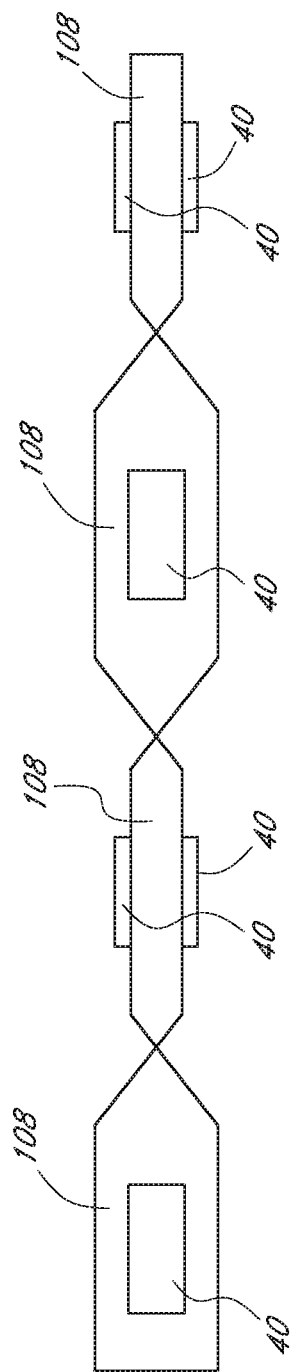
FIG. 7D is a side view of an ultrasound assembly center wire twisted into a helical configuration.

In a modified embodiment, such as illustrated in FIG. 7D, the common wire 108 can be twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off"

in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focused, more diffuse ultrasonic energy field to the treatment site.

In some embodiments, the ultrasound radiating members 40 comprise rectangular lead zirconate titanate ("PZT") ultrasound transducers. In some embodiments, the ultrasound transducer may have dimensions of about 0.017 inches by about 0.010 inches by about 0.080 inches (about 0.043 cm by about 0.025 cm by about 0.20 cm). In other embodiments, other configuration may be used. For example, disc-shaped ultrasound radiating members 40 can be used in other embodiments. In an embodiment, the common wire 108 comprises copper, and is about 0.005 inches (about 0.01 cm) thick, although other electrically conductive materials and other dimensions can be used in other embodiments. Lead wires 110 can comprise 36 gauge electrical conductors, while positive contact wires 112 can be 42 gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment 1 MHz and 3 MHz. In yet another embodiment, the ultrasound radiating members 40 are operated with a frequency of about 2 MHz.

FIG. 8 illustrates the inner core 34 positioned within the exterior tubular body 12 along a cross-sectional line similar to 2-2 in FIG. 1C. Details of the ultrasound assembly 42, provided in FIG. 7A, are omitted for clarity. As described above, the inner core 34 can be slid within the central lumen 51 of the interior tubular body 13, thereby allowing the inner core 34 to be positioned within the energy delivery section 18. For example, in an embodiment, the materials comprising the inner core energy delivery section 41, the tubular body energy delivery section 18, and the potting material 43 all comprise materials having similar acoustic impedance, thereby minimizing ultrasonic energy losses across material interfaces.

FIG. 8 further illustrates placement of fluid delivery ports 58 within the tubular body energy delivery section 18. As illustrated, holes or slits can be formed from the fluid delivery lumen 30 through the exterior tubular body 12, thereby permitting fluid flow from the asymmetrical gap 52 to the treatment site. Thus, a source of therapeutic compound coupled to the inlet port 32 can provide a hydraulic pressure which drives the therapeutic compound through the asymmetric gap 52 in the fluid delivery lumen 30 and out the fluid delivery ports 58. Thus, inlet port 32 is a first fluid injection port in fluid communication with the asymmetric gap 52.

In some embodiments, as illustrated in FIG. 8, the fluid delivery lumen 30 is not evenly spaced around the circumference of the exterior tubular body 12. As discussed, in some embodiments, the exterior tubular body 12 further accommodates the temperature sensor 20. As noted above, the temperature sensor can be a flexcircuit such as the flexcircuit 220 described above with respect to FIGS. 2A and 2B or flexcircuit 320 described with respect to FIGS. 12A and 12B. In some embodiments, the temperature sensor 20 can contact the interior tubular body 13 to bias the interior tubular body 13 against the interior surface of the exterior tubular body 12 and/or to one side of the fluid delivery lumen 30.

In some examples, the configuration of the interior tubular body 13 and temperature sensor 20 can provide a manufacturing benefit as it allows for the construction of the catheter 10 by simply inserting the interior tubular body 13 and temperature sensor 20 into the exterior tubular body 12. This can allow the gap 52 to form between the exterior surface of the interior tubular body 13 and the interior surface of the exterior tubular body 12. In some embodiments, the size, location, and geometry of the fluid delivery ports 58 can be selected to provide uniform fluid flow from the fluid delivery ports 58 to the treatment site. For example, in one embodiment, the fluid delivery ports 58 closer to the proximal region of the energy delivery section 18 have smaller diameters than fluid delivery ports 58 closer to the distal region of the energy delivery section 18, thereby allowing uniform delivery of fluid across the entire energy delivery section 18. The configuration of the interior tubular body 13 can also provide better kink resistance and can potentially reduce the ultrasound attenuation. In some embodiments where the fluid delivery ports 58 have similar sizes along the length of the exterior tubular body 12, the fluid delivery ports 58 have a diameter between about 0.0005 inches to about 0.0050 inches (between about 0.001 cm to about 0.013 cm). In another embodiment in which the size of the fluid delivery ports 58 changes along the length of the exterior tubular body 12, the fluid delivery ports 58 have a diameter between about 0.001 inches to about 0.005 inches (between about 0.002 to about 0.01 cm) in the proximal region of the energy delivery section 18, and between about 0.0020 inches to about 0.005 inches (between about 0.005 cm to 0.01 about cm) in the distal region of the energy delivery section 18. The increase in size between fluid delivery ports 58 depends on the material composition of the exterior tubular body 12, and on the gap 52. In some embodiments, the fluid delivery ports 58 can be created in the exterior tubular body 12 by punching, drilling, burning, or ablating (e.g. with a laser), or by any other suitable methods. The drug or therapeutic compound flowing along the length of the exterior tubular body 12 can be increased by increasing the density of the number of fluid delivery ports 58 toward the distal region 15 of the exterior tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the exterior tubular body 12 further defines cooling fluid lumen 44. The cooling fluid lumen 44 can be formed between outer surface 39 of the inner core 34 and the inner surface of the interior tubular body 13. In some embodiments, a cooling fluid can be introduced through the proximal access port 31 such that the cooling fluid flow is produced through cooling fluid lumen 44 and out the distal exit port 29 (see FIG. 1C). Thus, in some embodiments, the proximal access port 31 is a fluid injection port in fluid communication with an interior of the interior tubular body 13. In the illustrated arrangement, a cooling fluid can be introduced through the port 46 such that the cooling fluid flow is produced through cooling fluid lumen 44 and out the distal exit port 29. The cooling fluid lumen 44 can be evenly spaced around the inner core 34 so as to provide uniform cooling fluid flow over the inner core 34. Such a configuration can be desirable to remove unwanted thermal energy at the treatment site. As will be explained below, the flow rate of the cooling fluid and the power to the ultrasound assembly 42 can be adjusted to maintain the temperature of the inner core 34 in the energy delivery section 41 within a desired range.

In some embodiments, the inner core 34 can be rotated or moved within the interior tubular body 13. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the interior tubular body 13 without kinking of the interior tubular body 13 without kinking of the interior tubular body 13. Additionally, the inner core outer body 35 can include a material having the ability to transmit torque. Suitable materials for the outer body 35 can include, but are not limited to, polymides, polyesters, polyurethanes, thermoplastic elastomers and braided polyimides.

In one embodiment, the fluid delivery lumen 30 and the cooling fluid lumen 44 are open at the distal end of the exterior tubular body 12, thereby allowing the drug or therapeutic compound and the cooling fluid to pass into the patients' vasculature at the distal exit port. Or, if desired, the fluid delivery lumen 30 can be selectively occluded at the distal end of the exterior tubular body 12, thereby providing additional hydraulic pressure to drive the therapeutic compound out of the fluid delivery ports 58. In either configuration, the inner core 34 can prevented from passing through the distal exit port by providing the inner core 34 with a length that is less than the length of the tubular body. In other embodiments, a protrusion is formed on the internal side of the tubular body in the distal region 15, thereby preventing the inner core 34 from passing through the distal exit port.

In still other embodiments, the catheter 10 further includes an occlusion device (not shown) positioned at the distal exit port 29. The occlusion device can have a reduced inner diameter that can accommodate a guidewire, but that is less than the inner diameter of the central lumen 51. Thus the inner core 34 is prevented from extending through the occlusion device and out the distal exit port 29. For example, suitable inner diameters for the occlusion device include, but are not limited to, about 0.005 inches to about 0.050 inches (about 0.01 cm to about 0.13 cm). In other embodiments, the occlusion device has a closed end, thus preventing cooling fluid from leaving the catheter 10, and instead recirculating to the proximal region 14 of the exterior tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the exterior tubular body 12 can include a temperature sensor 20, which can be located adjacent the interior tubular body 13. In such embodiments, the proximal region 14 of the exterior tubular body 12 includes a temperature sensor lead which can be incorporated into cable 45 (illustrated in FIG. 1B). As discussed above, in some embodiments the temperature sensor 20 can have a minimal profile such that it can be placed within the exterior tubular body 12 adjacent the interior tubular body 13. In some embodiments, to have a minimal profile, the temperature sensor 20 can be made of a flexible circuit as described above. For example, the temperature sensor 20 can be the flexcircuit 220 of FIGS. 2A and 2B or the flexcircuit 320 of FIGS. 12A and 12B. In other embodiments, temperature sensor 20 can include, but is not limited to, temperature sensing diodes, thermistors, thermocouples, resistance temperature detectors ("RTDs") and fiber optic temperature sensors which use thermalchromic liquid crystals. In some embodiments, suitable temperature sensor 20 geometries can include a strip that lies along the length of the exterior tubular body 12. In other embodiments, suitable temperature sensor 20 geometries can include, but are not limited to, a point, a patch or a stripe. In some embodiments, to provide for easy of assembly, the temperature sensor(s) 20 can be positioned within the exterior tubular body 12 (as illustrated), and/or within one or more of the cooling fluid lumen 44.

Figure 9:
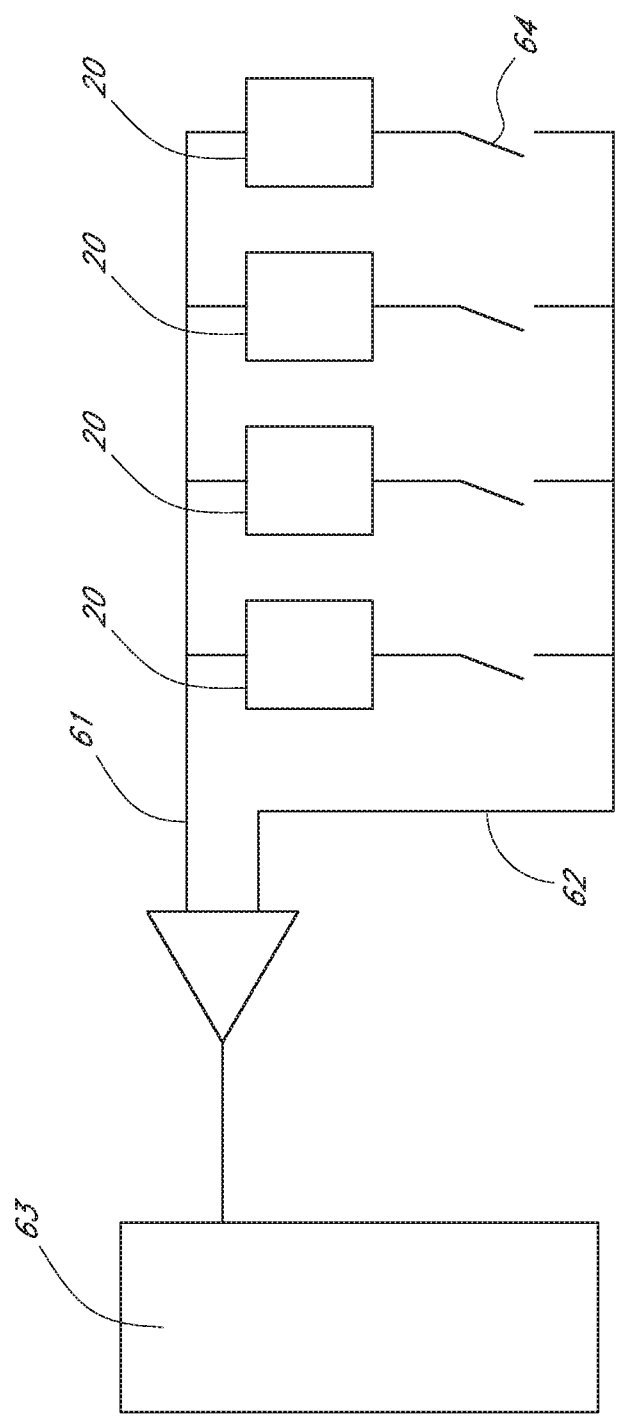
FIG. 9 illustrates a wiring diagram for connecting a plurality of temperature sensors with a common wire.

FIG. 9 illustrates one embodiment for electrically connecting a plurality of temperature sensor 20. In such embodiments, each temperature sensor 20 is coupled to a common wire 61 (e.g., a Constantan trace) and is associated with an individual return wire 62. Accordingly, n+1 wires can be used to independently sense the temperature at n distinct temperature sensor 20. The temperature at a particular temperature sensor 20 can be determined by closing a switch 64 to complete a circuit between that thermocouple's individual return wire 62 and the common wire 61. In embodiments wherein the temperature sensor 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires run through the exterior tubular body 12 to independently sense the temperature at n independent temperature sensor 20.

Figure 10:
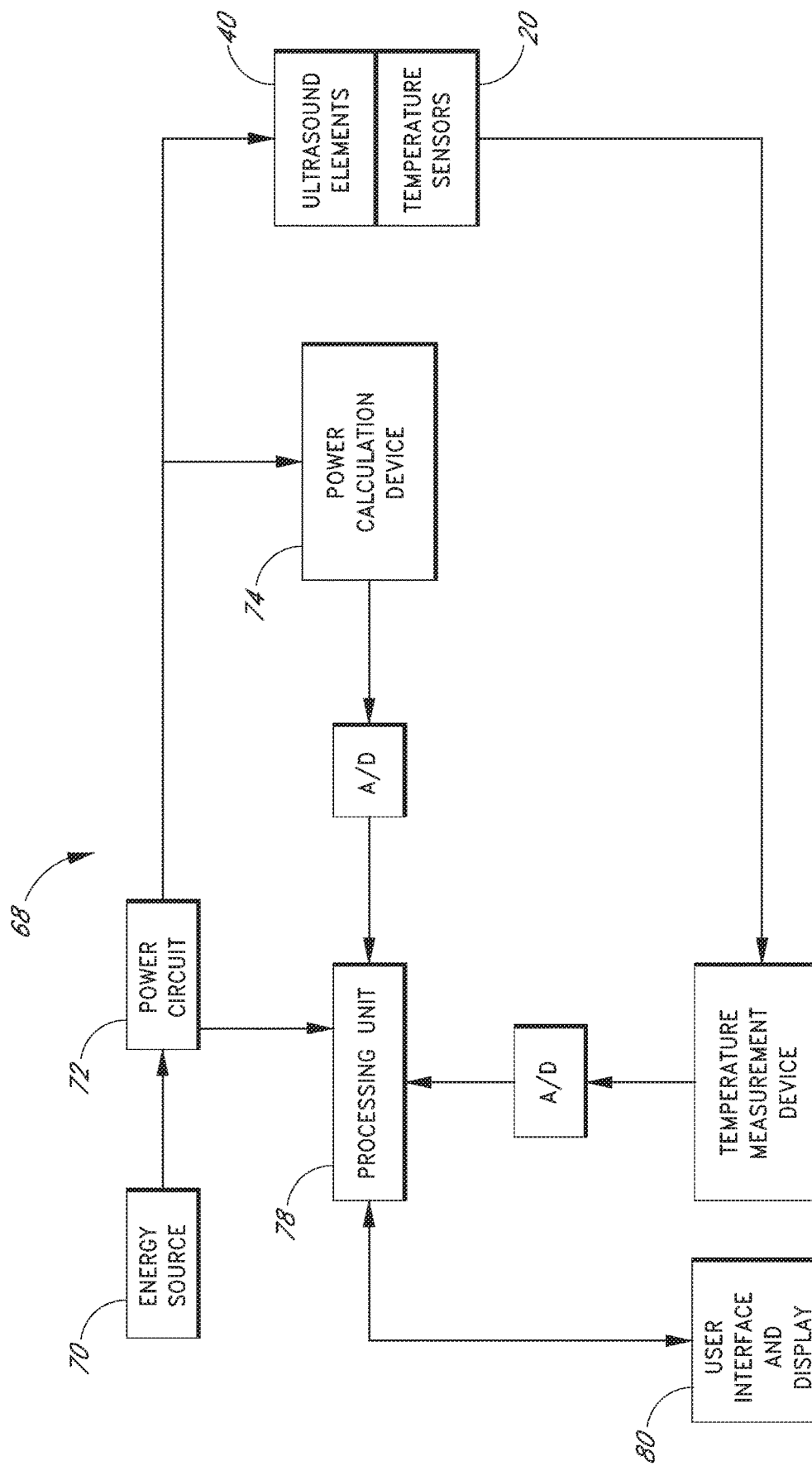
FIG. 10 is a block diagram of a feedback control system for use with an ultrasonic catheter.

FIG. 10 illustrates one embodiment of a feedback control system 68 that can be used with the catheter 10. The feedback control system 68 can be integrated into a control system that is connected to the inner core 34 via cable and/or the temperature sensor 20 via connector 100 (as illustrated in FIG. 1B). The feedback control system 68 allows the temperature at each temperature sensor 20 to be monitored and allows the output power of the energy source to be adjusted accordingly. A physician can, if desired, override the closed or open loop system.

The feedback control system 68 can include an energy source 70, power circuits 72 and a power calculation device 74 that is coupled to the ultrasound radiating members 40. A temperature measurement device 76 can coupled to the temperature sensor 20 in the exterior tubular body 12. A processing unit 78 can be coupled to the power calculation device 74, the power circuits 72 and a user interface and display 80.

In operation, the temperature at each temperature sensor 20 can be determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal can be proportional to the difference between the measured temperature and a desired temperature. The desired temperature can be determined by the user (at set at the user interface and display 80) or can be preset within the processing unit 78.

The temperature control signal can be received by the power circuits 72. In some embodiments, the power circuits 72 can be configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 can be reduced in response to that temperature control signal. Similarly, when the temperature control signal is below a particular level, the power supplied to a particular group of ultrasound radiating members 40 can be increased in response to that temperature control signal. After each power adjustment, the processing unit 78 can be configured to monitor the temperature sensor 20 and produces another temperature control signal which is received by the power circuits 72.

The processing unit 78 can further include safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensor 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 can also receive a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it can be generally desirable to prevent tissue at a treatment site from increasing more than 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. In some embodiments, the bus can be coupled to a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members can be operated in a pulsed mode. For example, in one embodiment, the time average electrical power supplied to the ultrasound radiating members can be between about 0.1 watts and 2 watts and can be between about 0.5 watts and 1.5 watts. In other embodiments, the time average electrical power supplied to the ultrasound radiating members is between about 0.001 watts and about 5 watts and can be between about 0.05 watts and about 3 watts. In some embodiments, the time average electrical power can be approximately 0.6 watts or 1.2 watts to a pair of ultrasound radiating members. In other embodiments, the time average electrical power over treatment time can be approximately 0.45 watts or 1.2 watts to a pair of ultrasound radiating members.

The duty cycle can be between about 1% and 50%. In some embodiments, the duty cycle can be between about 5% and 25%. In certain embodiments, the duty ratio can be approximately 7.5% or 15%. In other embodiments, the duty cycle can be between about 0.01% and about 90% and can be between about 0.1% and about 50%. In certain embodiments, the duty ratio can be approximately 7.5%, 15% or a variation between 1% and 30%. In some embodiments, the pulse averaged power to a pair of ultrasound radiating members can be between about 0.1 watts and 20 watts and can further be between approximately 5 watts and 20 watts. In certain embodiments, the pulse averaged power to a pair of ultrasound radiating members can be approximately 8 watts and 16 watts. In some embodiments, the pulse averaged electrical power to a pair of ultrasound radiating members can be between about 0.01 watts and about 20 watts and can be between approximately 0.1 watts and 20 watts. In other embodiments, the pulse averaged electrical power to a pair of ultrasound radiating members is approximately 4 watts, 8 watts, 16 watts, or a variation of 1 to 8 watts. The amplitude during each pulse can be constant or varied.

As described above, the amplitude, pulse width, pulse repetition frequency, average acoustic pressure or any combination of these parameters can be constant or varied during each pulse or over a set of portions. In a non-linear application of acoustic parameters the above ranges can change significantly. Accordingly, the overall time average electrical power over treatment time may stay the same but not real-time average power.

In some embodiments, the pulse repetition rate can be between about 5 Hz and 150 Hz and can further be between about 10 Hz and 50 Hz. In some embodiments, the pulse repetition rate is approximately 30 Hz. In other embodiments, the pulse repetition can be between about 1 Hz and about 2 kHz and more can be between about 1 Hz and about 50 Hz. In certain embodiments, the pulse repetition rate can be approximately 30 Hz, or a variation of about 10 to about 40 Hz. The pulse duration can be between about 1 millisecond and 50 milliseconds and can be between about 1 millisecond and 25 milliseconds. In certain embodiments, the pulse duration can be approximately 2.5 milliseconds or 5 milliseconds. In other embodiments, the pulse duration or width can be between about 0.5 millisecond and about 50 milliseconds and can be between about 0.1 millisecond and about 25 milliseconds. In certain embodiments, the pulse duration can be approximately 2.5 milliseconds, 5 or a variation of 1 to 8 milliseconds. In certain embodiments, the average acoustic pressure can be between about 0.1 to about 20 MPa or in another embodiment between about 0.5 or about 0.74 to about 1.7 MPa. In one particular embodiment, the transducers can be operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds. In one particular embodiment, the transducers can be operated at an average power of approximately 0.45 watts, a duty cycle of approximately 7.5%, a pulse repetition rate of 30 Hz, a pulse average electrical power of approximately 6 watts and a pulse duration of approximately 2.5 milliseconds. The ultrasound radiating member used with the electrical parameters described herein can have an acoustic efficiency greater than 50%. In some embodiments, the acoustic efficiency can be greater than 75%. The ultrasound radiating member can be formed a variety of shapes, such as, cylindrical (solid or hollow), flat, bar, triangular, and the like. The length of the ultrasound radiating member can be between about 0.1 cm and about 0.5 cm. The thickness or diameter of the ultrasound radiating members can be between about 0.02 cm and about 0.2 cm.

Figure 11A:
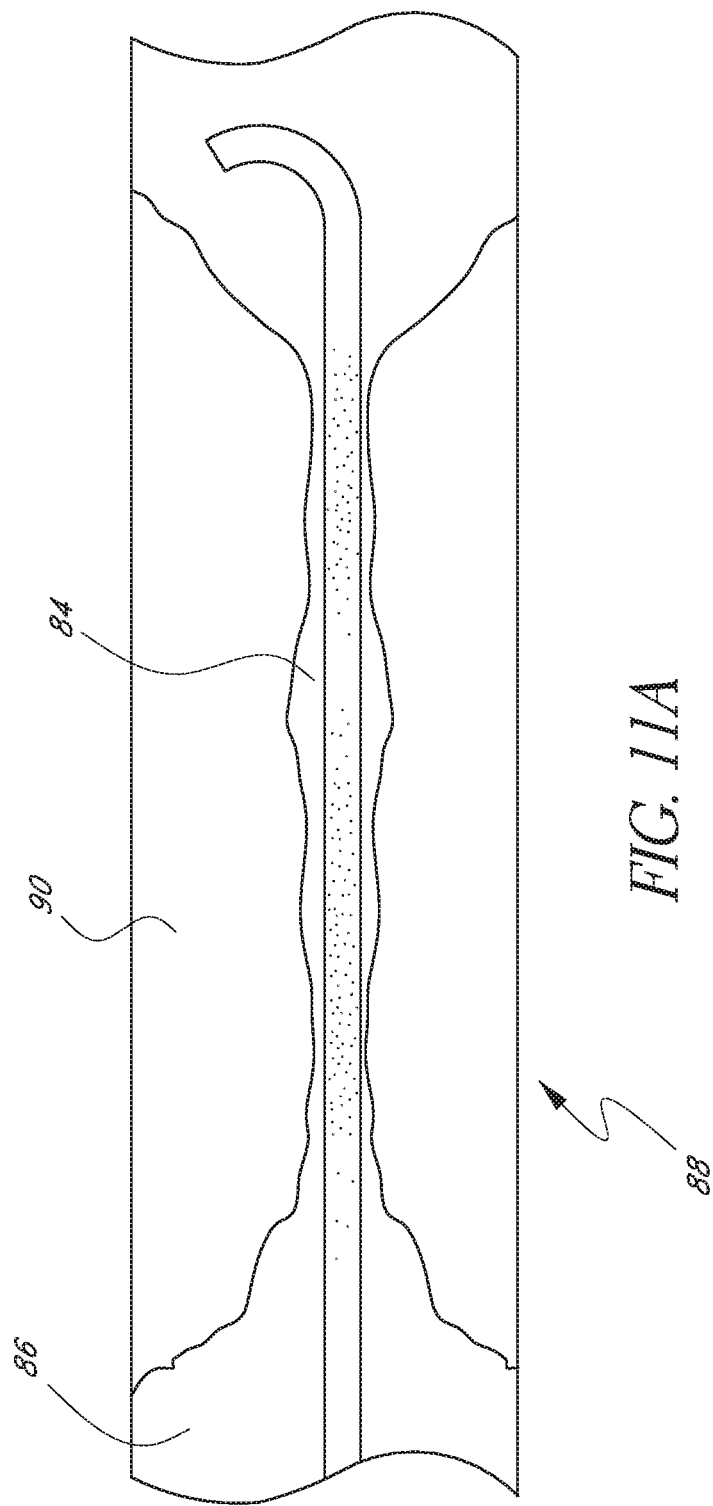
FIG. 11A is a side view of a treatment site.

FIGS. 11A through 11D illustrate a method for using the ultrasonic catheter 10. As illustrated in FIG. 11A, a guidewire 84 similar to a guidewire used in typical angioplasty procedures can be directed through a patient's vessels 86 to a treatment site 88 which includes a clot 90. The guidewire 84 can be directed through the clot 90. Suitable vessels 86 can include, but are not limited to, the large periphery blood vessels of the body. Additionally, as mentioned above, the ultrasonic catheter 10 also has utility in various imaging applications or in applications for treating and/or diagnosing other diseases in other body parts.

Figure 11B:
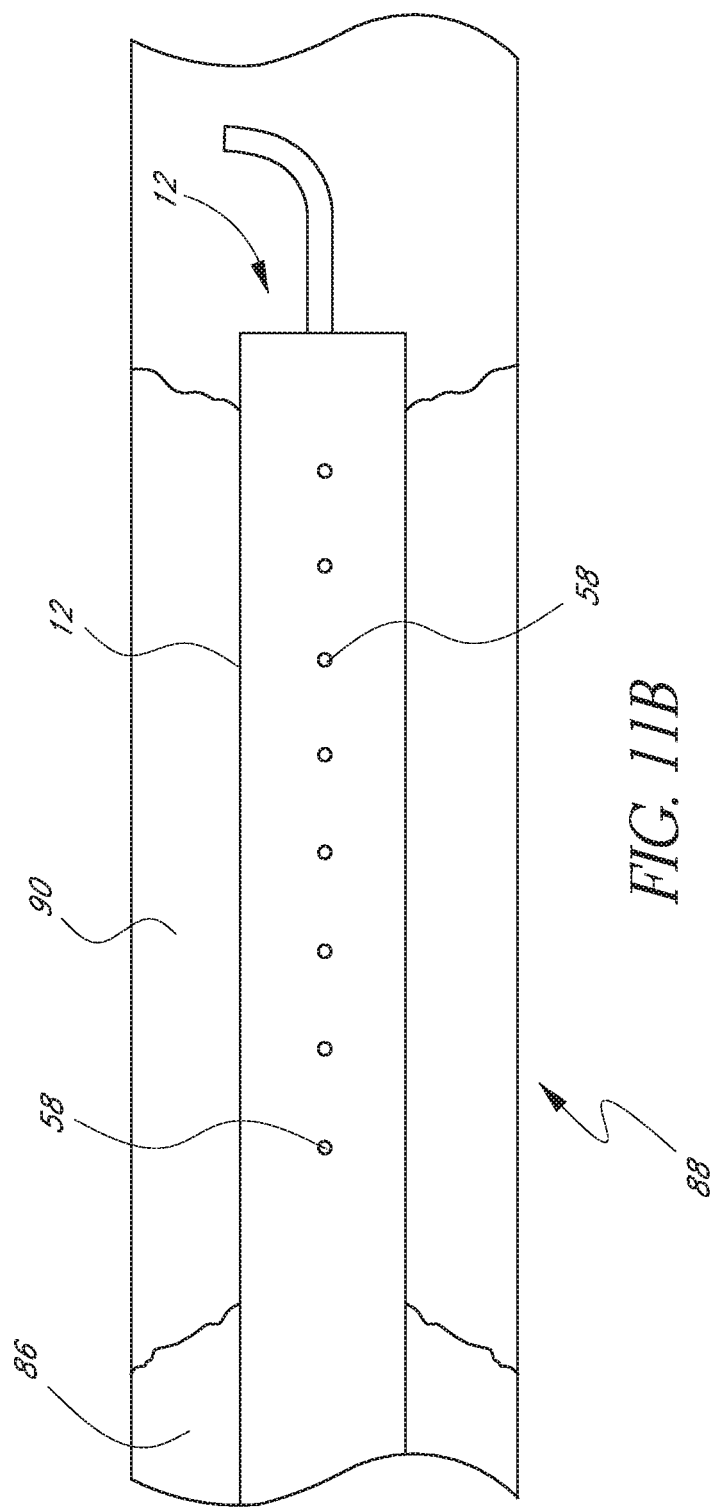
FIG. 11B is a side view of the distal end of an ultrasonic catheter positioned at the treatment site of FIG. 11A.

As illustrated in FIG. 11B, the catheter 10 can be slid over and advanced along the guidewire 84 using conventional over-the-guidewire techniques with the guidewire extending through the interior tubular body 13. The catheter 10 can be advanced until the energy delivery section 18 of the exterior tubular body 12 is positioned at the clot 90. In certain embodiments, radiopaque markers (not shown) are positioned along the energy delivery section 18 of the exterior tubular body 12 to aid in the positioning of the exterior tubular body 12 of the catheter 10 within the treatment site 88.

Figure 11C:
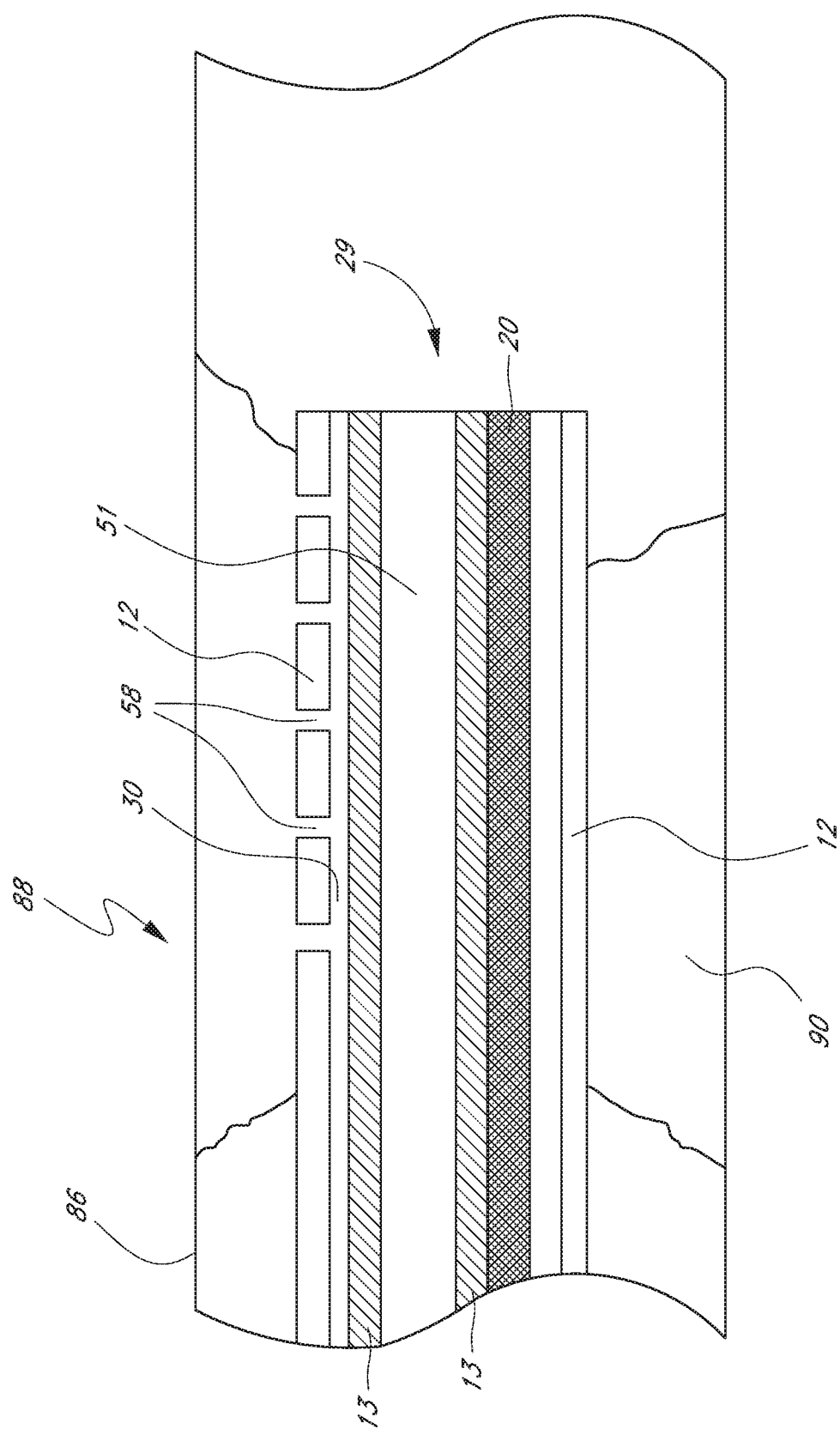
FIG. 11C is a cross-sectional schematic view of the distal end of the ultrasonic catheter of FIG. 11B positioned at the treatment site before a treatment.

As illustrated in FIG. 11C, the guidewire 84 can then be withdrawn from the catheter 10 by pulling the guidewire 84 from the proximal region 14 of the catheter 10 while holding the catheter stationary. This leaves catheter 10 (exterior body 12 shown in FIG. 11C) positioned at the treatment site 88.

Figure 11D:
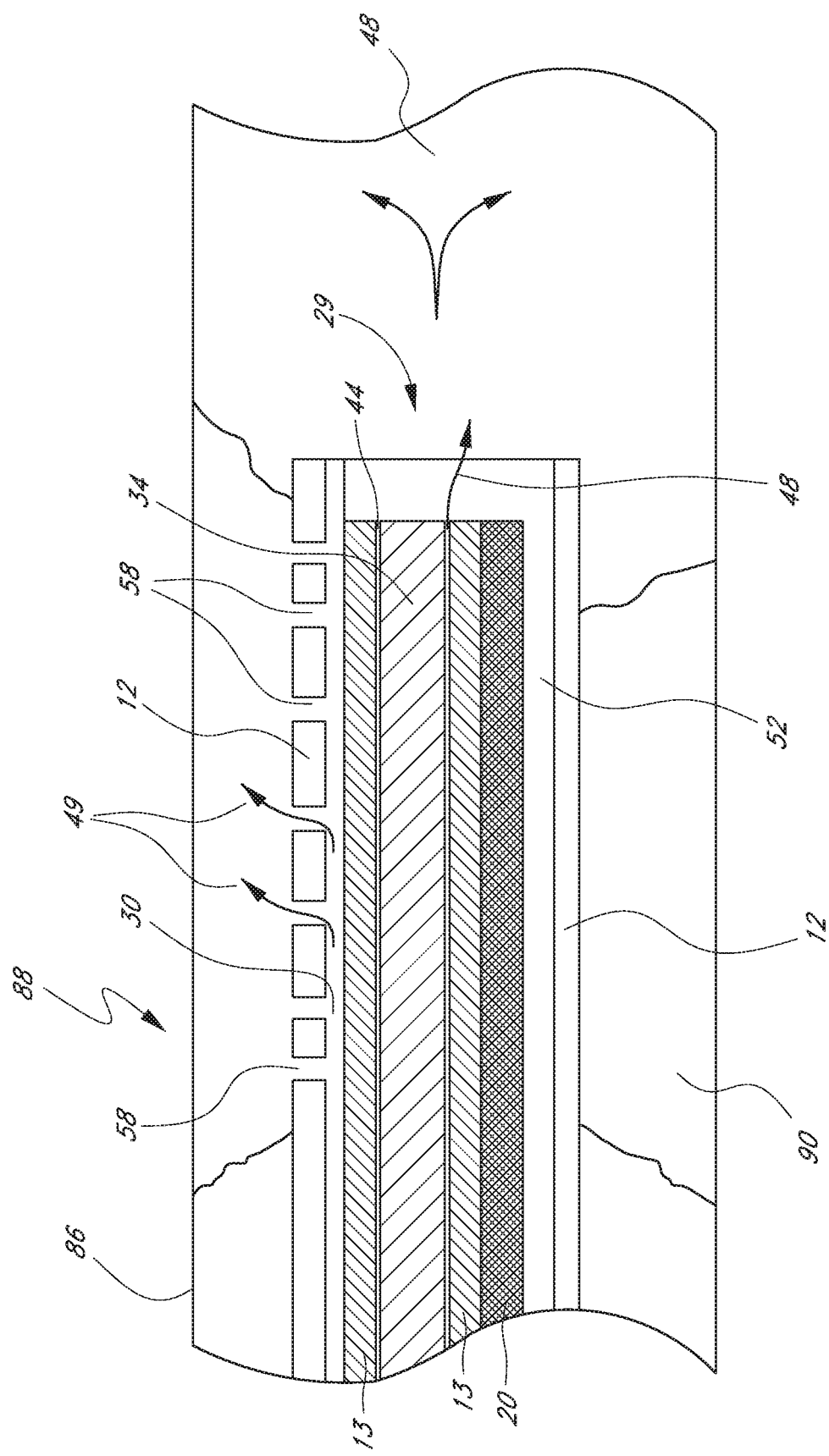
FIG. 11D is a cross-sectional schematic view of the distal end of the ultrasonic catheter of FIG. 11C, wherein an inner core has been inserted into the tubular body to perform a treatment.

As illustrated in FIG. 11D, the inner core 34 can then be inserted into interior tubular body 13 until the ultrasound assembly 42 is positioned at least partially within the energy delivery section 18 of the exterior tubular body 12. Once the inner core 34 is properly positioned, the ultrasound assembly 42 can be activated to deliver ultrasonic energy through the energy delivery section 18 to the clot 90. As described above, suitable ultrasonic energy is delivered with a frequency between about 20 kHz and about 20 MHz.

In a certain embodiment, the ultrasound assembly 42 comprises sixty ultrasound radiating members 40 spaced over a length of approximately 30 to 50 cm. In such embodiments, the catheter 10 can be used to treat an elongate clot 90 without requiring movement of or repositioning of the catheter 10 during the treatment. However, in some embodiments, the inner core 34 can be moved or rotated within the catheter 10 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicated that a therapeutic compound flows through gap 52 in the fluid delivery lumen 30 and out the fluid delivery ports 58 to the treatment site 88. In the schematic illustrations of FIGS. 11A and 11D, the fluid delivery ports 58 are shown in a different location than illustrated in FIG. 8.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than that described above. The therapeutic compound and ultrasonic energy can be applied until the clot 90 is partially or entirely dissolved. Once the clot 90 has been dissolved to the desired degree, the exterior tubular body 12 and the inner core 34 are withdrawn from the treatment site 88.

Pulmonary Embolism Treatment

In some embodiments, the ultrasonic catheter 10 can be configured to be introduced into the major blood vessels leading from the heart to the lungs (e.g., the pulmonary artery). In one embodiment of use, femoral venous access may be used to place the ultrasonic catheter 10 into such vessels. In such embodiments, the ultrasonic catheter 10 can be advanced through femoral access site, through the heart and into the pulmonary artery. The dimensions of the ultrasonic catheter 10 are adjusted based on the particular application for which the ultrasonic catheter 10 is to be used.

As noted above, the ultrasound catheter 10 can also be used for treating PE. The ultrasound catheter 10 can be introduced into a patient's pulmonary artery over a guidewire. The distal region 15 of the ultrasound catheter 10 is then advanced to the treatment site within the pulmonary artery. The ultrasound energy delivery section 18 of the ultrasound catheter can be positioned across the treatment site using fluoroscopic guidance via radiopaque marker located near the proximal end and the distal end of the ultrasound energy delivery section 18. Once the ultrasound catheter 10 is successfully placed, the guidewire may be removed from the ultrasound catheter 10. In the embodiments depicted in FIGS. 1-11, the elongate inner core 34 comprising at least one ultrasound radiating member 40 can then be inserted into the central lumen 51 of the ultrasound catheter 10. The at least one ultrasound radiating member 40 can be positioned along the energy delivery section 18 of the ultrasound catheter 10. In some embodiments, at least one cooling lumen 44 is formed between an outer surface 39 of the inner core 34 and an inner surface of the interior tubular body 13. The coolant infusion pump is attached to the cooling fluid inlet port 46, which is in communication with the at least one cooling fluid lumen 44. The drug infusion pump can then be connected to the fluid inlet port 32, which is in communication with the asymmetric gap 52 in the at least one fluid delivery lumen 30.

The thrombolytic drug can then be delivered to the treatment site through at least one fluid delivery lumen 30.

In some embodiments, a plurality of fluid delivery ports 58 is in fluid communication with the fluid delivery lumen 30 can be located on the ultrasound catheter at the ultrasound energy delivery section 18. The drug can be infused through the fluid delivery ports 58 to the treatment site.

The ultrasound energy may be delivered to the treatment site simultaneously or intermittently with the infusion of the thrombolytic drug. In some embodiments, the ultrasound energy is emitted to the treatment site prior to the thrombolytic drug being delivered. In some embodiments, the thrombolytic drug is delivered to the treatment site prior to the ultrasound energy being emitted. The ultrasound energy may be emitted according to the manner described above. In some embodiment, the power parameter and the physiological parameter of at least one ultrasound radiating member 40 may be varied as described above.

In some embodiments, the elongate inner core 34 may comprise five or less (i.e., one, two, three, four, or five) ultrasound radiating members 40. In some variants, by limiting the number of the ultrasound radiating members 40, it is can be possible to drive the ultrasound radiating members at a higher power for PE treatments.

High intensity ultrasound catheter may also be especially effective in treating pulmonary embolism. In some embodiments, the size of one or more ultrasound radiating members 40 positioned in the elongate inner core 34 can be increased to generate high intensity ultrasound. In other words, larger ultrasound radiating members can be used for this purpose. In some embodiments, positioning the ultrasound radiating members less than 1 cm apart can result in higher intensity ultrasound output.

Without being bound to the theory, the ultrasound can prepare the clot by unwinding the fibrin strands and increasing the permeability of the clot. Acoustic pressure waves and micro-streaming force the delivered drug into the clot, quickly permeating the clot with drug. As the drug is absorbed into the clot it binds with exposed plasminogen receptor sites. Once bound in the clot, the drug is no longer in free circulation, does not pass through the liver and is not metabolized.

In some embodiments, recombinant tissue plasminogen activator (rt-PA or Actilyse®) can be used with the ultrasound catheter 10 for the treatment of pulmonary embolism. The effective infusion dosage may range from about 0.12 mg/hr to about 2 mg/hr, from about 0.2 mg/hr to about 1.5 mg/hr, from about 0.5 mg/hr to about 1.5 mg/hr, or from about 1 mg/hr to about 2 mg/hr. The rt-PA maximum total infusion dose may be from about 10 mg to about 30 mg, from about 10 mg to about 20 mg, or about 25 mg. In some embodiment, as rt-PA is infused at a rate of about 1 mg/hr to about 2 mg/hr for about 3 to about 5 hours, then the infusion rate is decreased to about 0.5 mg/hr for 10 hours. In some embodiments, rt-PA is infused at a rate of about 1 mg/hr to about 2 mg/hr for about 5 hours, and then the infusion rate is decreased to about 0.5 mg/hr for 10 hours.

Other potential drugs that may be used with the ultrasound catheter for treating pulmonary embolism may include fibrinolytic compounds such as urokinase (Abbokinase®, Abbott laboratories, USA), streptokinase (Streptase®, Behringwerke AG), and reteplase (Retavase™, Centocor, Inc.). The enzymatic activity and stability of these fibrinolytics (including rt-PA) are not changed after exposure to therapeutic ultrasound.

In general, digital angiographic equipment is used to aid the performance of the ultrasound catheter treatment procedure. Continuous invasive pressure monitoring and ECG-monitoring can be used for obtaining baseline hemodynamic parameters, including heart rate, right atrial, right ventricular, and pulmonary artery pressures, as well as the mixed-venous oxygen saturation from the pulmonary artery. A systemic arterial blood pressure and a systemic oxygen saturation can also be measured if an arterial line is in place. Otherwise, the systemic cuff blood pressure is measured and the oxygen saturation is obtained by pulse oximetry. In one embodiment, a blood pressure sensor is integrated into the ultrasound catheter.

In some embodiments, a feedback control loop configured to monitor the baseline hemodynamic parameters and/or mixed-venous oxygen saturation can be integrated into the control system 100. The output power of the energy source can then be adjusted according to the readings. A physician can override the closed or open loop system if so desired.

In some embodiments, an unilateral filling defect in one main or proximal lower lobe pulmonary artery by contrast-enhanced chest CT indicates that only one ultrasound catheter is to be placed into the pulmonary artery. In case of bilateral filling defect is detected in both main or proximal lower lobe pulmonary arteries by contrast-enhancing chest CT, two ultrasound catheters may be placed.

As noted above, in some embodiments, femoral venous access may be used for placing the ultrasound catheter in the pulmonary arteries. For example, a 6F introducer sheath is inserted in the common femoral vein. An exchange-length 0.035-inch (0.089-cm) angled guidewire, for example the Terumo soft wire, may be used for probing the embolic occlusion under fluoroscopy. A 5F standard angiographic catheter, such as a multipurpose catheter or pigtail catheter or any other pulmonary angiographic catheter may be used with small manual contrast injections for localizing the embolic occlusion and for positioning the catheter such that the energy delivery section 18 of the ultrasound catheter spans the thrombus. If the distal extent of the embolus is not visible angiographically or if it is difficult to probe the embolic occlusion, a 4F Terumo glide catheter may be used for obtaining very small selective contrast injections beyond the presumed thrombotic occlusion after transiently removing the 0.035 wire. After the wire is successfully placed beyond the thrombotic occlusion in a lower lobe segmental branch, the angiographic catheter is exchanged for the ultrasound catheter.

Finally, in embodiments wherein the ultrasound catheter including elongate inner core with ultrasound catheter (as shown in FIGS. 1-11) is used, the 0.035-inch (0.089-cm) guidewire can be removed and the elongate inner core with ultrasound radiating member(s) 40 is inserted into the ultrasound catheter. The therapeutic compound can be introduced through the at least one fluid delivery lumen 30 and out of the fluid delivery port(s) 58 to the treatment site.

After about 12 to about 15 hours of drug infusion, the rt-PA infusion can be replaced with heparinized saline infusion (about 1 μg/ml) at an infusion rate of 5 ml/hr. Sometime between about 16 and about 24 hours after the start of the rt-PA infusion, follow-up hemodynamic measurements (heart rate, systemic arterial pressure, right atrial, right ventricular and pulmonary artery pressures, mixed venous and pulse oximetric oxygen saturations, cardiac output, pulmonary vascular resistance) and controlled removal of the ultrasound catheter can be performed. The decision on the exact duration of the ultrasound-assisted thrombolysis infusion is at the discretion of the physician, but in one embodiment it is recommended to continue the treatment for 15 hours (or until 20 mg of rt-PA has been delivered) if well tolerated by the patient.

In certain embodiments, it can be beneficial to keep the catheter centered in the pulmonary artery during the treatment process. For example, centering the ultrasound radiating member 40 in the pulmonary artery may improve the uniform exposure at the treatment site. In some embodiments, the ultrasound catheter 10 also includes a centering mechanism for keeping the catheter centered during the treatment. In some embodiments, the centering mechanism of the catheter 10 can be provided with one or more balloons disposed around the catheter 10 toward the distal region 15.

As described above, in some embodiments, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, and G5 of ultrasound radiating members 40 that are electrically connected to each other. The five groups are also electrically connected to the control system 100. In some embodiments, two, three, or four or more than five groups of ultrasound radiating member 40 may be electrically connected to each other and the control system 100. Each group (G1-GS) may comprise one or more individual ultrasound elements. For example, in one embodiment, each group comprises five or less (i.e., one, two, three, four, or five) ultrasound radiating members 40. In other embodiments, more than 5 ultrasound elements can be provided in each group. Modified embodiments may also include different numbers of elements within each group.

In the embodiment of FIG. 6, each group G1-G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

The wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

Figure 13:
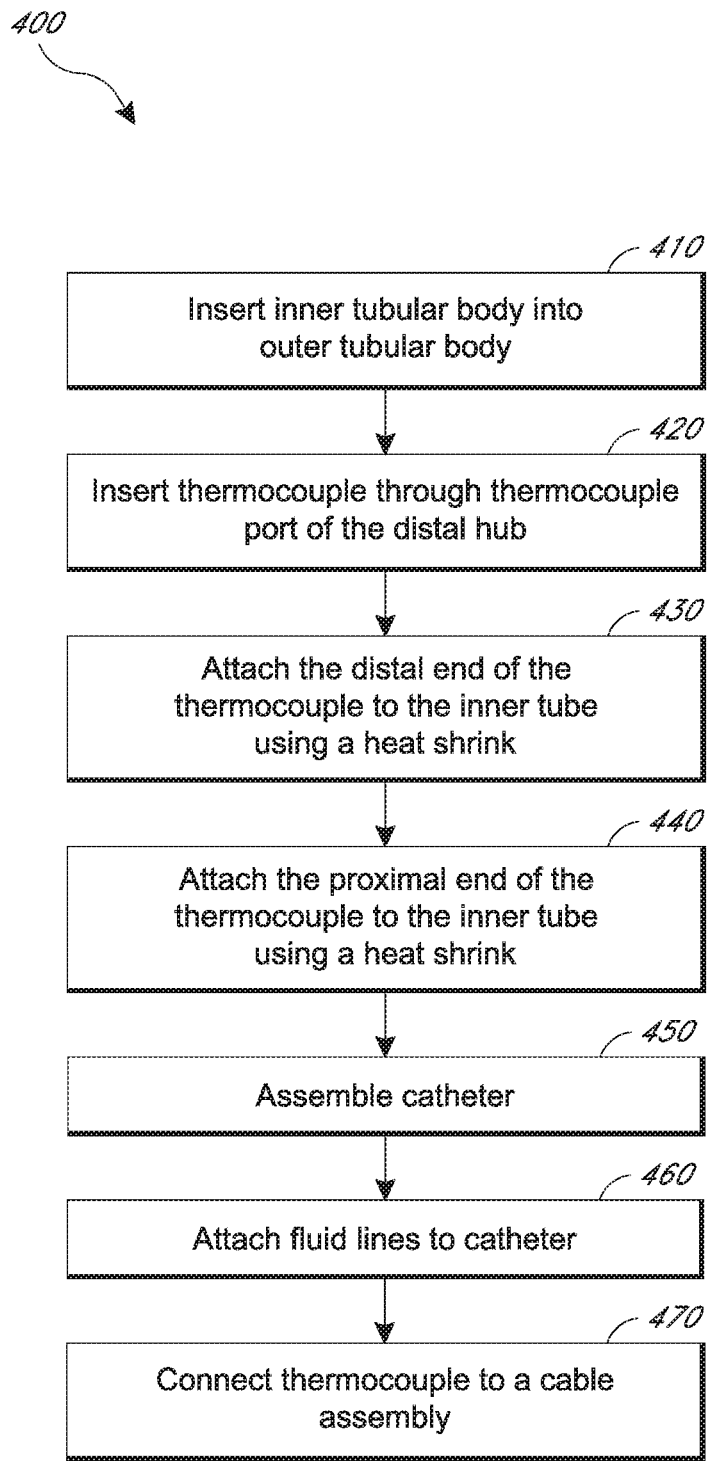
FIG. 13 illustrates a schematic of a method of manufacturing a catheter comprising a flexcircuit.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group can be interdigitated with respect to ultrasound radiating members of a different group.
Method for Assembling a Catheter with a Temperature Sensor As discussed above, the configuration of the temperature sensor 20 in the exterior tubular body 12 can provide for ease of assembly and manufacturability. In one aspect, the disclosure resides in a method of manufacturing a catheter comprising a flexible circuit and/or a ribbon thermocouple according to any of the embodiments described herein. In a particular embodiment of the disclosure, the flexible circuit is configured to form a thermocouple. In a particular embodiment of the disclosure, the thermocouple ribbon is configured to form a thermocouple. FIG. 13 illustrates a flow-chart of an example method for assembling a catheter with a flex circuit thermocouple and/or thermocouple ribbon.

The method for assembling a catheter with flex circuit thermocouple and/or thermocouple ribbon can first include block 410 which describes first inserting the interior tubular body 13 into the exterior tubular body 12. In some embodiments, the interior tubular body 13 can be inserted into the exterior tubular body 12 such that the outside surface of the interior tubular body 13 contacts the inside surface of the exterior tubular body 12. This can form an asymmetrical space within the exterior tubular body 12 to accommodate a temperature sensor 20.

Next, the method can include block 420 which describes inserting the flexcircuit temperature sensor 20 or and/or thermocouple ribbon 500, 600 through the first barb inlet 69 of the distal hub 65. As described above, the temperature sensor 20 can be the flexcircuit 220 of FIGS. 2A and 2B or flexcircuit 320 of FIGS. 12A-12B or ribbon thermocouple 500, 660 of FIGS. 2D-2I.

Once inserted, the temperature sensor 20 can be attached to the proximal and distal ends of the interior tubular body 13 as discussed in block 430 and block 440. The attachment of the temperature sensor 20 to the interior tubular body 13 can be done using an adhesive or a heat shrink.

At block 450, the remaining components of the catheter 10 are assembled. For example, in the catheter 10 described above, FIG. 1E illustrates an exploded view of the various components of the catheter 10 and the connections between each of the components.

Once the catheter 10 has been assembled, the method can include block 460 which describes attaching the fluid lines (e.g. fluid line 91 and cooling fluid line 92) to the catheter. As shown above, the fluid line 91 can be attached to the second barb inlet 75 while the cooling fluid line 92 is attached to the barb inlet 63.

To attach the temperature sensor 20 to an electrical source, block 470 describes connecting the temperature sensor 20 to a cable assembly. As illustrated in FIG. 1E, the cable 45 can attach to the temperature sensor 20 through first barb inlet 69. The distal end of the cable 45 can then attach to a control system 100. The various methods and techniques described above provide a number of ways to carry out the disclosure. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

The disclosure includes the following additional embodiments:

Embodiment 1. An ultrasound catheter comprising:

a first tubular body having a first longitudinal axis extending centrally through the tubular body, the first tubular body including at least one delivery port extending through a wall of the first tubular body;

a second tubular body having a second longitudinal axis extending centrally through the second tubular body, the first and second longitudinal axes being displaced from each other such that an asymmetrical longitudinally extending gap is formed between an outer surface of the second tubular body and an interior surface of the first tubular body;

a flexible circuit forming a thermocouple extending longitudinally within the gap between the first tubular body and the second tubular body; and an inner core positioned within the second tubular body, the inner core comprising at least one ultrasound element.

Embodiment 2: The ultrasound catheter of Embodiment 1, wherein the flexible circuit positioned in the widest portion of the asymmetrical gap.

Embodiment 3: The ultrasound catheter of any one of Embodiments 1-2, wherein the flexible circuit extends along the length of the first tubular body.

Embodiment 4: The ultrasound catheter of any one of Embodiments 1-3, wherein the flexible circuit is adjacent to an outer surface of the second tubular body.

Embodiment 5: The ultrasound catheter of any one of Embodiments 1-4, wherein the ultrasound catheter comprises a first fluid injection port in fluid communication with the gap.

Embodiment 6: The ultrasound catheter of any one of Embodiments 1-5, wherein the apparatus further comprises a second fluid injection port in fluid communication with an interior of the second tubular body.

Embodiment 7: The ultrasound catheter of any one of Embodiments 1-6, wherein the flexible circuit is configured to measure temperature at different points along the length of ultrasound catheter.

Embodiment 8: The ultrasound catheter of any one of Embodiments 1-7, wherein the inner core comprises a plurality of ultrasound radiating members extending along a length of the ultrasound catheter.

Embodiment 9: The ultrasound catheter of Embodiment 8, wherein the flexible circuit comprises a plurality of joints between traces of dissimilar materials.

Embodiment 10: The ultrasound catheter of Embodiment 9, wherein the plurality of joints between traces of dissimilar materials extend along the length of the ultrasound catheter in which the plurality of ultrasound radiating members is positioned.

Embodiment 11: The ultrasound catheter of Embodiment 10, wherein the joints between traces of dissimilar materials are formed by a plurality traces of a first material connected to a single trace of second dissimilar material.

Embodiment 12: The ultrasound catheter of Embodiment 1, wherein the flexible circuit comprises a plurality of traces formed on the flexible circuit separated by insulating material, the plurality of traces comprising at least two traces of a first material connected to a single trace of second dissimilar material at different points along a length of the flexible circuit.

Embodiment 13: A method of manufacturing a catheter comprising:

inserting an inner tubular body into an outer tubular body; and placing a flexible circuit between the outer and inner tubular body, wherein the temperature sensor is adjacent to an outer surface of the inner tubular body such that the inner tubular body does not extend along the same longitudinal axis a the outer tubular body.

Embodiment 14: The method of manufacturing of Embodiment 13, wherein the flexible circuit is configured to form a thermocouple.

Embodiment 15: The method of manufacturing of Embodiment 13, further comprising: forming an inner core, wherein the inner core is configured to be insertable into the inner tubular body.

Embodiment 16: The method of manufacturing of Embodiment 13, wherein inserting the elongate fluid delivery body and inserting the temperature sensor forms an asymmetrical cross-section in the catheter.

Embodiment 17: An ultrasound catheter comprising:

an elongate inner tubular body;

an elongate outer tubular;

wherein the elongate inner tubular body is positioned within the elongate outer tubular body to form an asymmetrical gap between an outer surface of the inner tubular body and an interior surface of the elongate outer tubular body to form a fluid delivery lumen, and a temperature sensor extending along the outer surface of the inner tubular body within the gap; and an inner core positioned within the inner tubular body and comprising at least one ultrasound element.

Embodiment 18: The ultrasound catheter of Embodiment 17, wherein the temperature sensor is formed by a flexible circuit.

Embodiment 19: An ultrasound catheter of Embodiment 18, wherein the temperature sensor is located in the widest portion of the asymmetrical gap.

Embodiment 20: A flexible circuit for a catheter, the flex circuit comprising a plurality of traces formed on the flexible circuit separated by insulating material, the plurality of traces comprising at least two traces of a first material connected to a single trace of second dissimilar material at different points along a length of the flexible circuit.

Embodiment 22: The flexible circuit of Embodiment 20, wherein the second dissimilar material is Constantan and the first material is copper.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of embodiments herein.

What is claimed is:

1. A method of manufacturing a catheter comprising:
   inserting an inner tubular body into an outer tubular body;
   placing a temperature sensor between the outer and inner tubular body, wherein the temperature sensor is adjacent to an outer surface of the inner tubular body such that the inner tubular body does not extend along the same longitudinal axis as the outer tubular body; and
   wherein the inner tubular body is asymmetrical and includes a plurality of indentations along the interior surface of the inner tubular body.

2. The method of manufacturing of claim 1, wherein the temperature sensor is configured to form a thermocouple.

3. The method of manufacturing of claim 1, further comprising:
    forming an inner core, wherein the inner core is configured to be insertable into the inner tubular body.

4. The method of manufacturing of claim 3, wherein the inner core comprises at least one ultrasound element.

5. The method of manufacturing of claim 1, wherein inserting an inner tubular body into an outer tubular body and placing a temperature sensor between the outer and inner tubular body forms an asymmetrical cross-section in the catheter.

6. The method of manufacturing of claim 1, wherein the temperature sensor comprises a flexcircuit.

7. The method of manufacturing of claim 1, wherein an asymmetrical longitudinally extending gap is formed between an outer surface of the inner tubular body and an interior surface of the outer tubular body.

8. The method of manufacturing of claim 7, wherein the temperature sensor is positioned in a widest portion of the asymmetrical gap.

9. The method of manufacturing of claim 1, wherein the temperature sensor extends along a length of the outer tubular body.

10. The method of manufacturing of claim 1, wherein the temperature sensor comprises a flexible circuit that comprises a plurality of joints between traces of dissimilar materials.

11. A method of manufacturing a catheter comprising:
    inserting an inner tubular body into an outer tubular body; and
    placing a temperature sensor between the outer and inner tubular body, wherein the temperature sensor is adjacent to an outer surface of the inner tubular body such that the inner tubular body does not extend along the same longitudinal axis as the outer tubular body;
    wherein the temperature sensor comprises a plurality of filament pairs wherein each of the filaments is insulated; and
    a plurality of thermocouples wherein each of the plurality of thermocouples are formed between each of the plurality of filament pairs.

12. A method of manufacturing a catheter comprising:
    inserting an inner tubular body into an outer tubular body;
    placing a temperature sensor between the outer and inner tubular body, wherein the temperature sensor is adjacent to an outer surface of the inner tubular body such that the inner tubular body does not extend along the same longitudinal axis as the outer tubular body; and
    wherein the inner tubular body is asymmetrical and includes a plurality of protrusions along the interior surface of the inner tubular body.

* * * * *